US009422235B2

(12) United States Patent
Yacovan et al.

(10) Patent No.: US 9,422,235 B2
(45) Date of Patent: Aug. 23, 2016

(54) SULFONAMIDE DERIVATIVES WITH THERAPEUTIC INDICATIONS

(75) Inventors: Avihai Yacovan, Gedera (IL); Iris Alroy, Ness Ziona (IL); Alexander Aizikovich, Rehovot (IL); Sima Mirilashvili, Lod (IL); Flavio Grynszpan, Mazkeret Batia (IL)

(73) Assignee: Pharmos Corporation, Iselin, NJ (US)

( * ) Notice: Subject to any disclaimer, the term of this patent is extended or adjusted under 35 U.S.C. 154(b) by 360 days.

(21) Appl. No.: 12/520,061

(22) PCT Filed: Dec. 19, 2007

(86) PCT No.: PCT/IL2007/001569
§ 371 (c)(1),
(2), (4) Date: Nov. 16, 2009

(87) PCT Pub. No.: WO2008/075353
PCT Pub. Date: Jun. 26, 2008

(65) Prior Publication Data
US 2010/0056528 A1    Mar. 4, 2010

Related U.S. Application Data

(60) Provisional application No. 60/875,536, filed on Dec. 19, 2006.

(51) Int. Cl.
| C07C 311/39 | (2006.01) |
| C07C 311/48 | (2006.01) |
| C07C 311/51 | (2006.01) |
| C07C 311/40 | (2006.01) |
| C07D 405/12 | (2006.01) |
| C07D 471/08 | (2006.01) |
| C07D 209/08 | (2006.01) |
| C07D 209/48 | (2006.01) |
| C07D 213/38 | (2006.01) |
| C07D 213/42 | (2006.01) |
| C07D 217/04 | (2006.01) |
| C07D 319/18 | (2006.01) |
| C07D 231/38 | (2006.01) |
| C07D 295/12 | (2006.01) |
| C07D 295/13 | (2006.01) |
| C07D 295/22 | (2006.01) |
| C07D 307/14 | (2006.01) |
| C07D 307/52 | (2006.01) |
| C07D 317/58 | (2006.01) |

(52) U.S. Cl.
CPC ............ *C07C 311/39* (2013.01); *C07C 311/40* (2013.01); *C07C 311/48* (2013.01); *C07C 311/51* (2013.01); *C07D 209/08* (2013.01); *C07D 209/48* (2013.01); *C07D 213/38* (2013.01); *C07D 213/42* (2013.01); *C07D 217/04* (2013.01); *C07D 231/38* (2013.01); *C07D 295/12* (2013.01); *C07D 295/13* (2013.01); *C07D 295/22* (2013.01); *C07D 307/14* (2013.01); *C07D 307/52* (2013.01); *C07D 317/58* (2013.01); *C07D 319/18* (2013.01); *C07D 405/12* (2013.01); *C07D 471/08* (2013.01); *C07C 2101/02* (2013.01); *C07C 2101/14* (2013.01); *C07C 2101/18* (2013.01); *C07C 2102/42* (2013.01); *C07C 2103/74* (2013.01)

(58) Field of Classification Search
CPC .. C07C 311/39; C07C 311/48; C07C 311/51; C07C 311/40; C07D 405/12; C07D 471/08; C07D 209/08; C07D 209/48; C07D 213/38; C07D 213/42; C07D 217/04; C07D 319/18; C07D 23/38; C07D 295/12; C07D 295/13; C07D 295/22; C07D 307/14; C07D 307/52
See application file for complete search history.

(56) References Cited

U.S. PATENT DOCUMENTS

| 2,373,335 A | 4/1945 | Paul ............................. 260/800 |
| 3,860,582 A | 1/1975 | Schoenberg et al. ...... 260/239.6 |
| 3,948,990 A | 4/1976 | Barlow et al. ................. 260/576 |

FOREIGN PATENT DOCUMENTS

| BE | 629369 | 9/1963 |
| GB | 1 031 082 | 5/1966 |
| GB | 1 383 306 | 2/1975 |
| GB | 1 386 091 | 3/1975 |
| JP | 59-135255 | 8/1984 |
| WO | WO 01/14375 | 3/2001 |
| WO | WO 02/057240 | 7/2002 |
| WO | WO 03/076406 | 9/2003 |
| WO | 2004018433 | 3/2004 |
| WO | WO 2004/029027 | 4/2004 |
| WO | WO 2006/048330 | 5/2006 |

OTHER PUBLICATIONS

Chawla et al., CRIPS vol. 5, No. 1, Jan.-Mar. 2004, p. 9-12.*
Newman et al., DDT vol. 8, Oct. 2003, p. 898-905.*
Zweidler et al., caplus an 1957:77160, 1957.*
Wojahn, caplus 1944:33247.*
Johnson et al., caplus an 1924:414, 1924.*
Krishnamurthy, caplus an 1983:53274, 1983.*
Jones et al., 1996, caplus an 1996:73234.*
Cao et al., 2007, caplus an 2007:538389.*
Moore et al., 2008, caplus an 2008:609351.*
Fulp et al., 2009, caplus an 2009:92562.*

(Continued)

*Primary Examiner* — Sun Jae Yoo
(74) *Attorney, Agent, or Firm* — Winston & Strawn LLP

(57) ABSTRACT

The invention provides sulfonamide compounds of formula (I) as defined herein, pharmaceutical compositions containing the same and methods of treatment using such compounds and pharmaceutical compositions. These compounds have a common wide range of beneficial therapeutic indications, in particular as analgesic and anti-inflammatory agents.

23 Claims, 24 Drawing Sheets

(56) References Cited

OTHER PUBLICATIONS

Adams and Cairns (1939) Attempts to prepare optically active ethylenimine derivatives containing an asymmetric nitrogen atom. Journal of the American Chemical Society 61: 2464-7.

Adams et al., (1939) Sulfanilamide derivatives. II. Journal of the American Chemical Society 61: 2346-9.

Badetti et al., (2005) Nucleophilic aromatic substitution on 4-fluorophenylsulfonamides: nitrogen, oxygen, and sulfur nucleophiles. Synlett 2005(3): 449-452.

Desai and Desai (1992) 2-[N4-{N1-(n-butyl)sulfanilamido}]-4-(4'-chloroanilino)-6-(arylthioureido)-s-triazine derivatives. Journal of the Institution of Chemists (India) 64(4): 143-4.

Gadukevich et al., (1990) Reactivity of derivatives of phenylanthanilic acid. IX. Acid-base pproperties of sufamoyl derivatives of phenylanthranilic acid in dioxane-water. Organic Reactivity (Tartu) 27(3-4): 152-8.

Lin et al., (2005) 1-Acyl-1H-[1,2,4]triazole-3,5-diamine Analogues as Novel and Potent Anticancer Cyclin-Dependent Kinase Inhibitors: Synthesis and Evaluation of Biological Activities. Journal of Medicinal Chemistry 48(13): 4208-4211.

Mohamed et al., (1986) Synthesis of different types of chlorinated sulfonamides with expected insecticidal and antimicrobial activities. Acta Pharmaceutica Jugoslavica 36(3): 301-10.

Saha et al., (2000) Novel antifungals based on 4-substituted imidazole: solid-phase synthesis of substituted aryl sulfonamides towards optimization of in vitro activity. Bioorg Med Chem Lett 10(24): 2735-2739.

Shani et al., (1983) Structure activity correlation for diuretic furosemide congeners. Pharmacology 26(3): 172-80.

International Search Report, PCT/IL2007/001569, dated May 27, 2008.

Jones, Terrence R. et al., "Structure-Based Design of lipophilic Quinazoline Inhibitors of Thymidylate Synthase", Journal of Medicinal Chemistry, vol. 39, pp. 904-917, 1996.

Krishnamurthy S., "A Highly Efficient and General N-Monomethylation of Functionalised Primary Amines Via Formylation-Borane Methyl Sulphide Reduction", Tetrahedron Letters, vol. 23, No. 33, pp. 3315-3318, 1982.

Romines K.R. et al., "Structure-Activity Relationship Studies of Novel Benzophenones Leading to the Discovery of Potent, Next Generation HIV Nonnucleoside Reverse Transcriptase Inhibitor", Journal of Medicinal Chemistry, vol. 49, pp. 727-739, 2006.

Williamson, Douglas S. et al., "Structure-Guided Design of Pyrazolo[1,5-a]pyramidines as Inhibitors of Human Cyclin-Dependent Kinase 2", Bioorganic & Medicinal Chemistry Letters, vol. 15, pp. 863-867, 2005.

Wojahn H.: Zur kenntnis der Brom-Sulfonamid-Verbindungen. 2:Mitteilung uber Sulfonamide. Archiv Der Pharmazie, vol. 281, 1943: 193-201.

\* cited by examiner

Figure 1

| Cpd # | Structure | % Binding hCB1 Affinity (IC50 nM) | Ki (nM) | % Binding hCB2 Affinity (IC50 nM) | Ki (nM) | hCB1/ hCB2 |
|---|---|---|---|---|---|---|
| 1 | 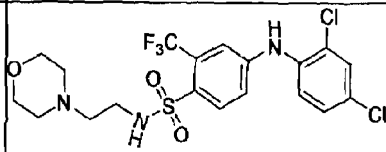 | 34090 | 21020 | 1837 | 933 | |
| 2 | 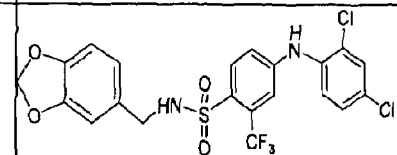 | NB | NB | NB | NB | |
| 3 | | 313 | 180 | 30 | 17 | 10.59 |
| 3* | | 6000 | 3000 | | | |
| 4 | | 720 | 400 | 37 | 19 | 21.05 |
| 4* | | 2000 | 1156 | 56 | 29 | 39.86 |
| 4* | | 3058 | 1556 | 68 | 37 | 42.05 |
| 4* | | 580 | 260 | 76 | 34 | 7.65 |

Fig. 1 (cont. 1)
| # | Structure | | | | | |
|---|---|---|---|---|---|---|
| 4* | 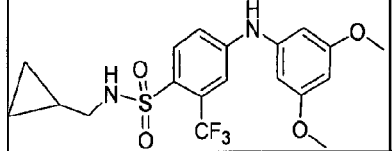 | | | 58.1 | 29.2 | |
| 4* | 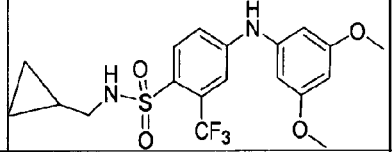 | NB | NB | | | |
| 5 | 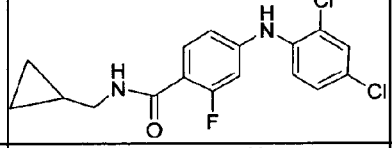 | NB | NB | 2150 | 826 | - |
| 6 | 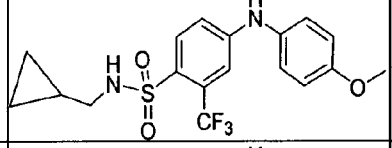 | 712 | 350 | 179 | 84 | 4.17 |
| 6* | 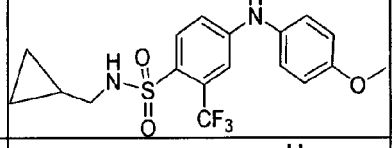 | 6000 | 3000 | | | |
| 7 | 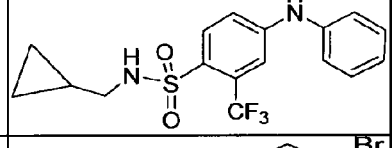 | 2000 | 1156 | 198 | 90 | 12.84 |
| 8 | 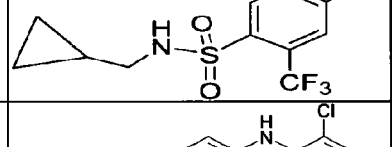 | NB | NB | NB | NB | - |
| 9 | 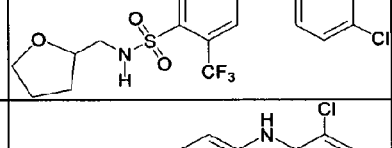 | 2288 | 1264 | 50 | 28 | 45.14 |
| 9* | 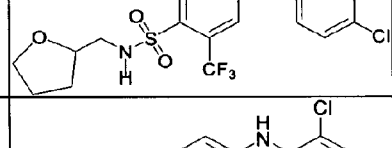 | 2301 | 1032 | 84 | 38 | 27.16 |
| 10 | 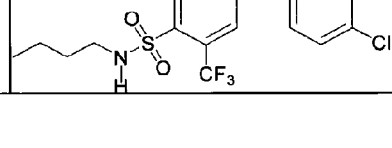 | 8571 | 4757 | 290 | 168 | 28.32 |

Fig. 1 (cont. 2)

| # | Structure | | | | | |
|---|---|---|---|---|---|---|
| 11 | (structure) | 17360 | 8837 | 59970 | 32510 | |
| 11* | (structure) | NB | NB | 72 | 37 | |
| 11* | (structure) | 11000 | 5564 | 1056 | 438 | 12.70 |
| 12 | (structure) | 11000 | 5564 | 235 | 97 | 57.36 |
| 12* | (structure) | NB | NB | 11 | 6 | |
| 12* | (structure) | 6000 | 2680 | 6000 | 2680 | |
| 12* | (structure) | 6000 | 2680 | 6000 | 2680 | |
| 12* | (structure) | 6000 | 3000 | 853 | 363 | |
| 12* | (structure) | 6000 | | 6000 | | |
| 13 | (structure) | NB | NB | NB | NB | - |

Fig. 1 (cont. 3)

| # | Structure | | | | | |
|---|---|---|---|---|---|---|
| 14 | (cyclopropylmethyl-NH-C(O)-phenyl with NO2 and NH-phenyl) | NB | NB | NB | NB | - |
| 15 | (tetrahydrofuran-CH2-NH-SO2-phenyl(CF3)-NH-phenyl(2,4-diF)) | | | 1638 | 629 | |
| 16 | (cyclopropylmethyl-NH-SO2-phenyl(CF3)-NH-pyrimidine(4,6-diOMe)) | 6000 | 2666 | 511 | 220 | 12.12 |
| 17 | (tetrahydrofuran-CH2-NH-SO2-phenyl(F)-NH-phenyl(3,5-diOMe)) | 2000 | 889 | 953 | 411 | 2.16 |
| 18 | (tetrahydrofuran-CH2-NH-SO2-phenyl(F)-NH-phenyl(3,5-diOMe)) | NB | NB | 706 | 320 | - |
| 19 | (tetrahydrofuran-CH2-NH-SO2-phenyl(2,5-diF)-NH-phenyl(3,5-diOMe)) | NB | NB | 255 | 113 | - |
| 20 | (MeO-propyl-NH-SO2-phenyl(CF3)-NH-phenyl(3,5-diOMe)) | NB | NB | 3978 | 1768 | - |
| 21 | (tetrahydrofuran-CH2-NH-SO2-phenyl(CF3)-NH-phenyl(3,5-diOMe)) | 3577 | 1590 | 725 | 322 | 4.94 |
| 21* | (tetrahydrofuran-CH2-NH-SO2-phenyl(CF3)-NH-phenyl(3,5-diOMe)) | 1639 | 735 | 180 | 81 | 9.07 |

Fig. 1 (cont. 4)
| # | Structure | | | | | |
|---|---|---|---|---|---|---|
| 22 | 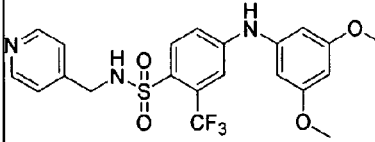 | NB | NB | 332 | 146 | - |
| 23 | 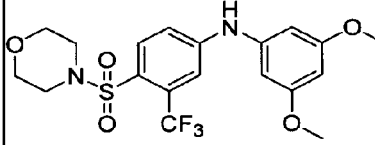 | NB | NB | 923 | 407 | - |
| 24 | 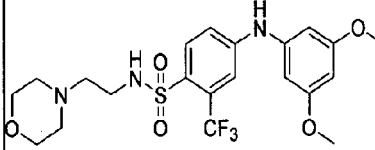 | NB | NB | 3704 | 1633 | - |
| 25 | 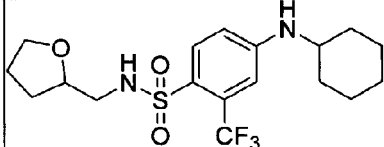 | NB | NB | 428 | 203 | - |
| 26 | 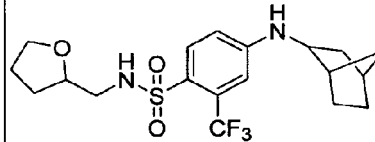 | 3808 | 1804 | 75 | 36 | 50.11 |
| 27 | 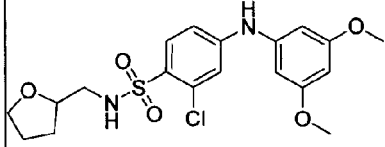 | NB | NB | 1441 | 682 | - |
| 28 | 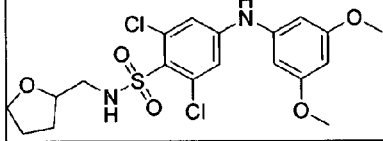 | 961 | 426 | 221 | 98 | 4.35 |
| 29 | 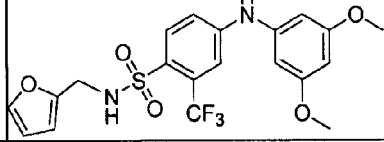 | 11380 | 5045 | 344 | 152 | 33.19 |
| 30 | 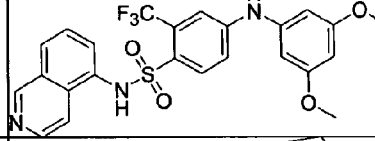 | NB | NB | 6000 | 2651 | - |
| 31 | 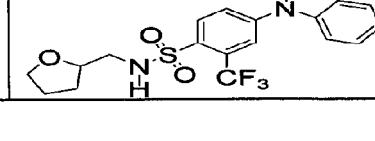 | 6000 | 2680 | 2778 | 1242 | 2.16 |

Fig. 1 (cont. 5)

| # | Structure | | | | | |
|---|---|---|---|---|---|---|
| 32 | 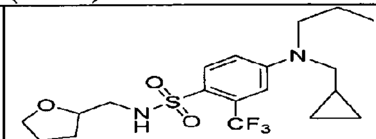 | 6000 | 2680 | 181 | 81 | 33.09 |
| 33 | 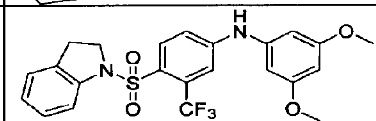 | 12000 | 6000 | 2080 | 880 | 6.82 |
| 34 | 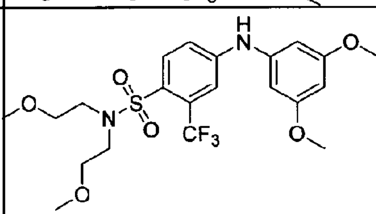 | 12000 | 6000 | 4000 | 1692 | 3.55 |
| 35 | 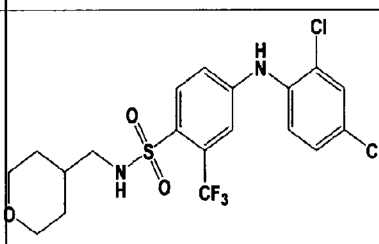 | 13810 | 5841 | 206 | 87 | 67.14 |
| 36 | | 5948 | 3266 | 106 | 53 | 61.62 |
| 36* | | 6000 | 3000 | 1933 | 822 | 3.65 |
| 36* | | | | 132 | 68 | |
| 36* | | | | 132 | 66 | |
| 36* | | | | 215 | 131 | |
| 37 | 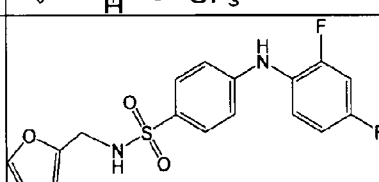 | 6000 | 3000 | NB | NB | - |

Fig. 1 (cont. 6)

| # | Structure | | | | | |
|---|---|---|---|---|---|---|
| 38 | (furan-CH2-NHSO2-Ar(CF3)-NH-Ar(2,4-diF)) | 5540 | 2337 | 1176 | 471 | 4.96 |
| 39 | (cyclopropyl-CH2-NHSO2-Ar-NH-Ar(2,4-diF)) | NB | NB | 1900 | 800 | - |
| 39* | (cyclopropyl-CH2-NHSO2-Ar-NH-Ar(2,4-diF)) | 6000 | | 6000 | | |
| 40 | (cyclopropyl-CH2-NHSO2-Ar-NH-norbornyl) | NB | NB | 1940 | 818 | |
| 40* | (cyclopropyl-CH2-NHSO2-Ar-NH-norbornyl) | NB | | NB | | |
| 41 | (tetrahydropyran-CH2-NHSO2-Ar(CF3)-NH-bicyclic) | | | 64.5 | 32.4 | |
| 41* | (tetrahydropyran-CH2-NHSO2-Ar(CF3)-NH-bicyclic) | | | 48.8 | 28 | |
| 41* | (tetrahydropyran-CH2-NHSO2-Ar(CF3)-NH-bicyclic) | 530 | 324 | 53.11 | 34.8 | |

Fig. 1 (cont. 7)
| # | Structure | | | | | |
|---|---|---|---|---|---|---|
| 41* | 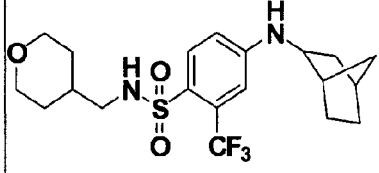 | 3076 | 1761 | | | |
| 42 | 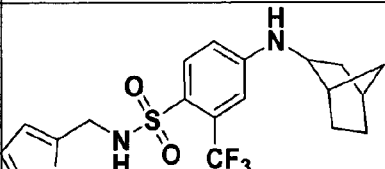 | | | 245 | 140.1 | |
| 43 | 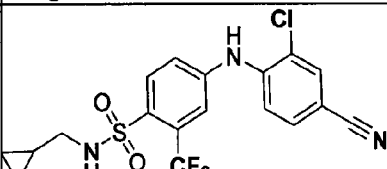 | | | 50.2 | 29 | |
| 44 | 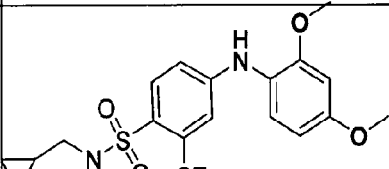 | 597 | 364 | 108.9 | 62 | |
| 44* | 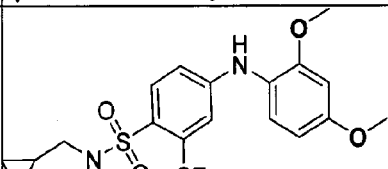 | 1420 | 813 | | | |
| 45 | 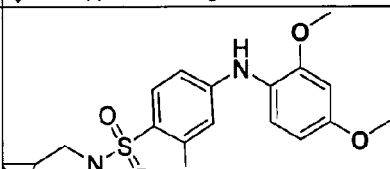 | | | 1748 | 999 | |
| 46 | 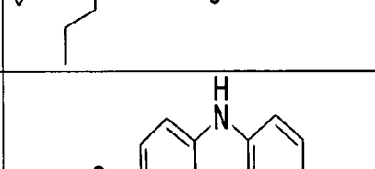 | | | 2150 | 825 | |

Fig. 1 (cont. 8)
| # | Structure | | | | | |
|---|---|---|---|---|---|---|
| 47 | 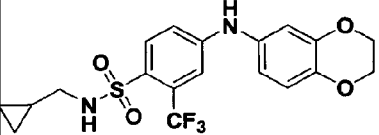 | | | 137.7 | 75.1 | |
| 47* | 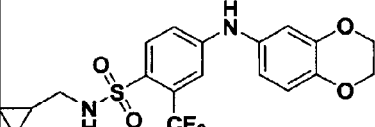 | NB | NB | | | |
| 48 | 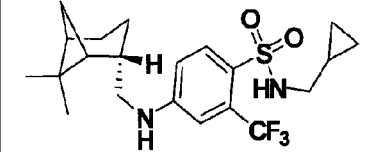 | | | 398 | 218 | |
| 49 | 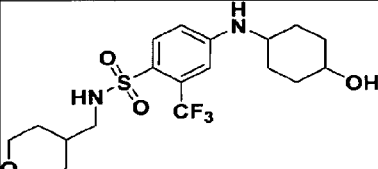 | | | NB | NB | |
| 50 | 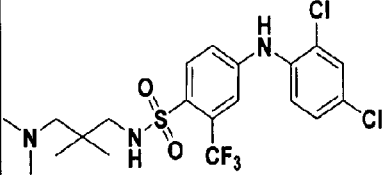 | | | 6000 | 3939 | |
| 51 | 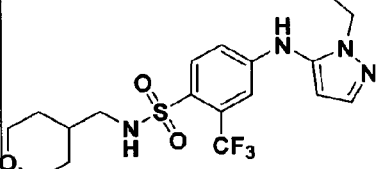 | | | 2819 | 1851 | |
| 52 | 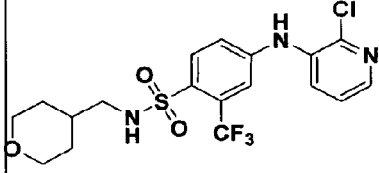 | | | NB | NB | |
| 53 | 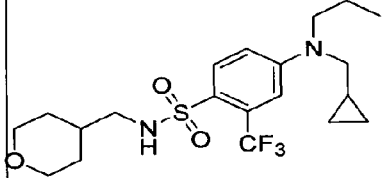 | | | 743 | 407 | |

Fig. 1 (cont. 9)
| # | Structure | | | C | D | |
|---|---|---|---|---|---|---|
| 54 | 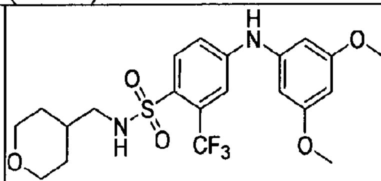 | | | 439 | 230 | |
| 55 | 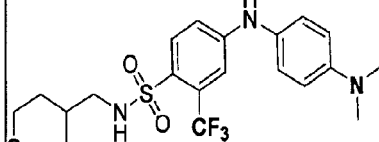 | | | 1520 | 8323 | |
| 56 | 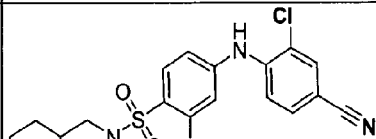 | | | 359 | 188 | |
| 57 | 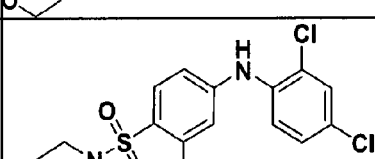 | | | 4195 | 2754 | |
| 57* | 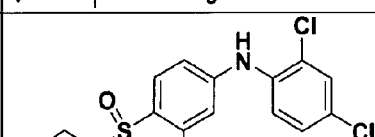 | | | 327 | 175 | |
| 58 | 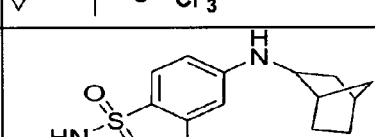 | 497 | 239 | 20 | 12.2 | |
| 58* | 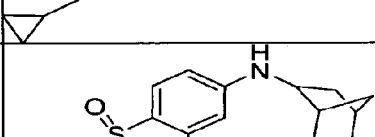 | 4751 | 2720 | | | |
| 59 | 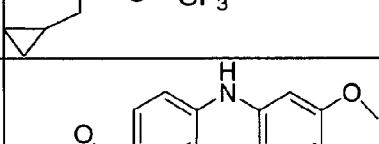 | | | 586 | 357.2 | |

Fig. 1 (cont. 10)
| | | | | | | |
|---|---|---|---|---|---|---|
| 59* | 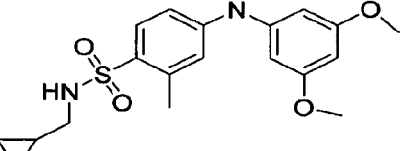 | | | 1029 | 499 | |
| 60 | 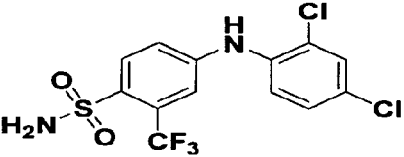 | | | NB | NB | |
| 61 | 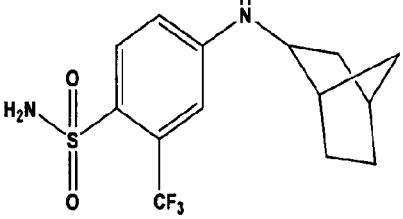 | | | 2133 | 1199 | |
| 62 | 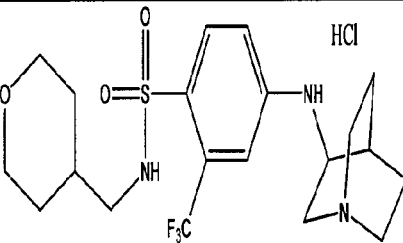 | | | NB | NB | |
| 63 | 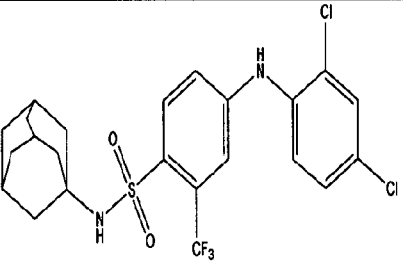 | | | NB | NB | |
| 64 | 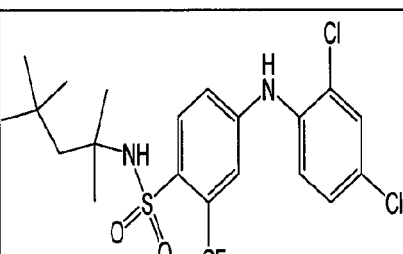 | | | 4934 | 2774 | |

Fig. 1 (cont. 11)
| # | Structure | | | IC50 | IC50 | |
|---|---|---|---|---|---|---|
| 65 | 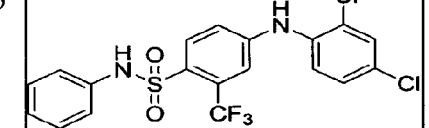 | | | 6246 | 3511 | |
| 66 | 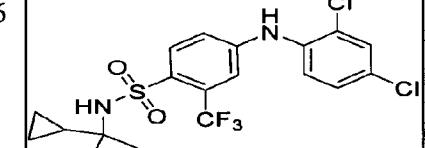 | | | 440 | 261 | |
| 67 | 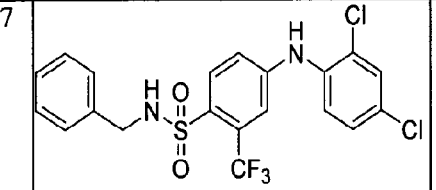 | | | 6000 | 6000 | |
| 68 | 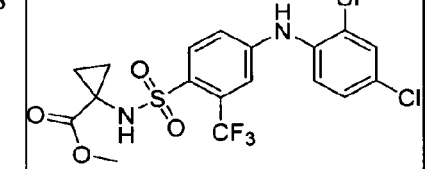 | | | 6404 | 3493 | |
| 69 | 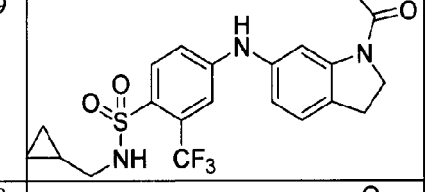 | | | 1216 | 664 | |
| 70 | 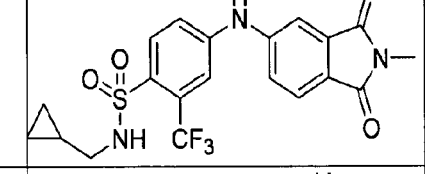 | | | 2414 | 1317 | |
| 71 | 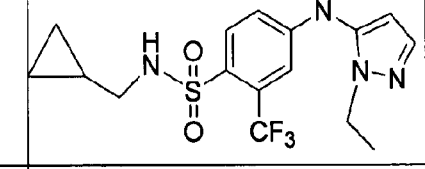 | | | 2747 | 1498 | |
| 72 | 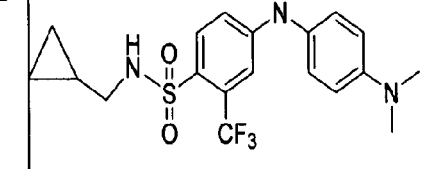 | | | 2655 | 1448 | |

Fig. 1 (cont. 12)
| # | Structure | | | | | |
|---|---|---|---|---|---|---|
| 73 | 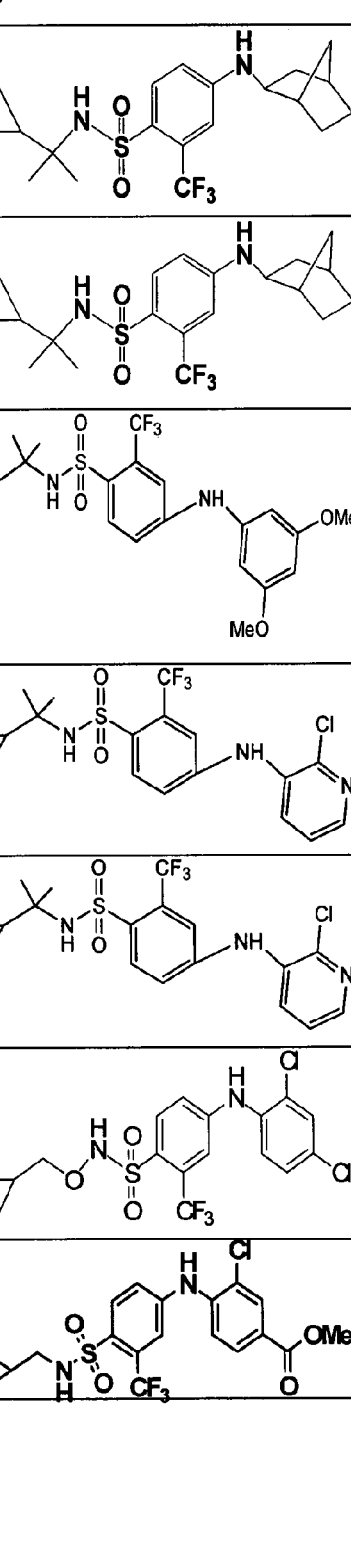 | NB | NB | 95.6 | 43.27 | |
| 74 | 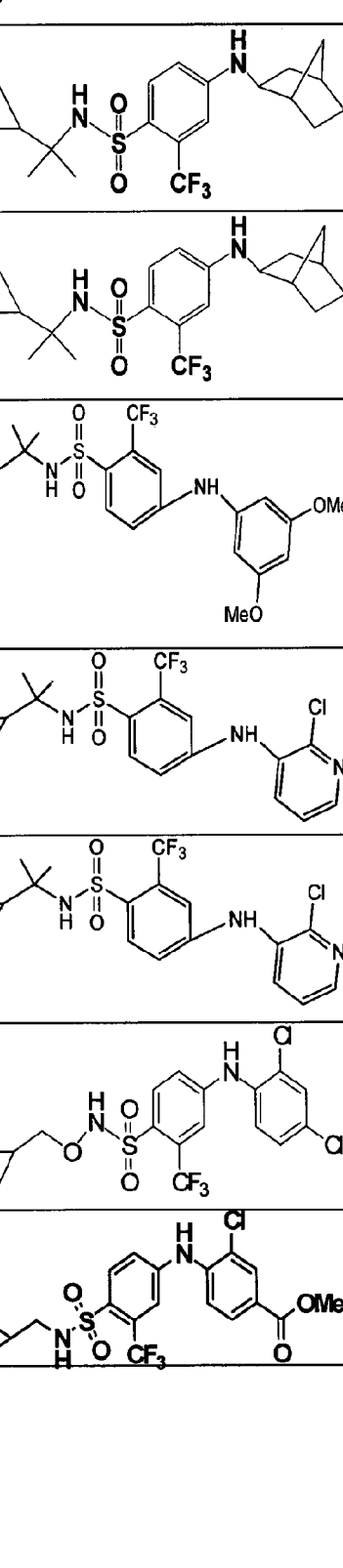 | 569 | 273 | 153 | 69.15 | |
| 74* | 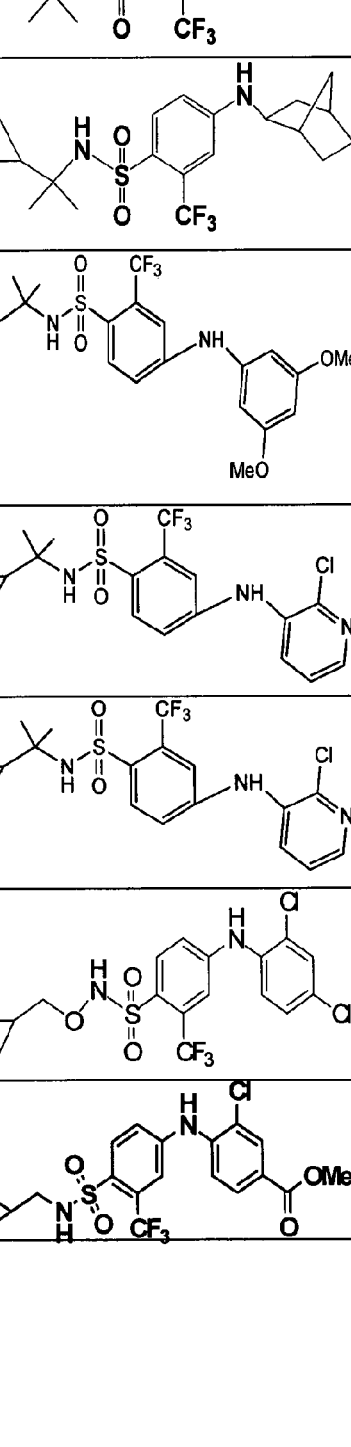 | 8813 | 4908 | | | |
| 75 | 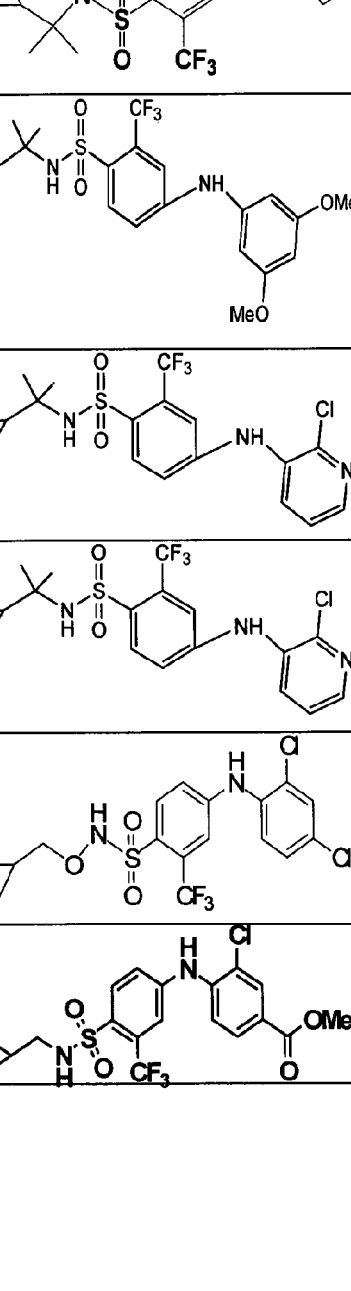 | | | 430.0 | 194.7 | |
| 76 | 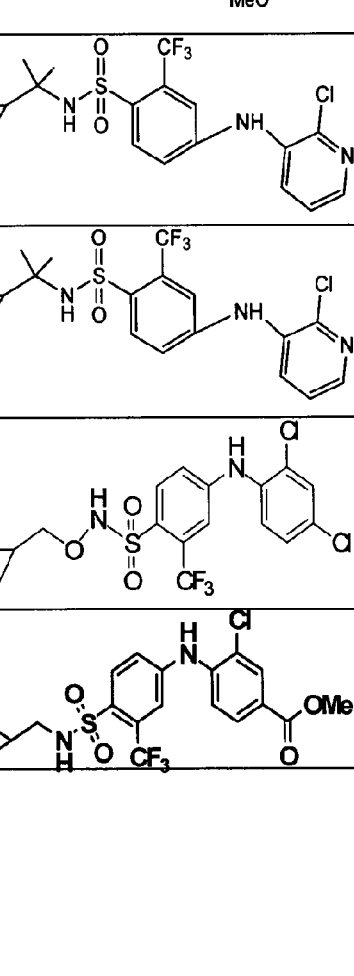 | | | 452 | 219 | |
| 76* | 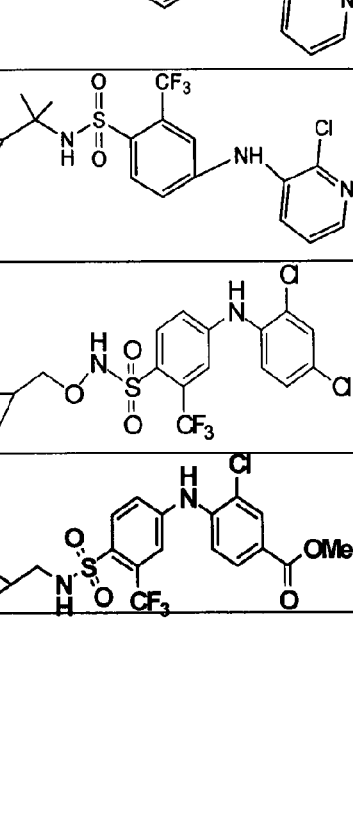 | | | 855 | 414.4 | |
| 77 | 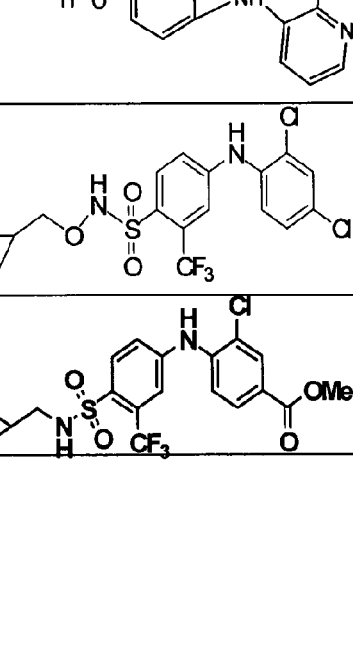 | | | 2262 | 1145 | |
| 78 | 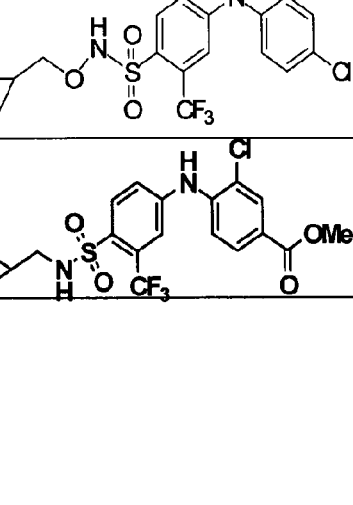 | | | 1107 | 560 | |

Fig. 1 (cont. 13)
| # | Structure | | | | |
|---|---|---|---|---|---|
| 79 | 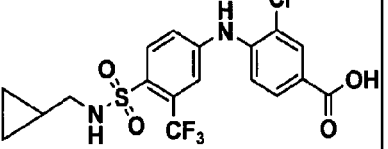 | | | 997 | 535 |
| 80 | 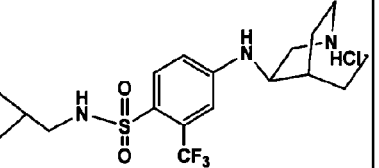 | | | 696 | 373 |
| 81 | 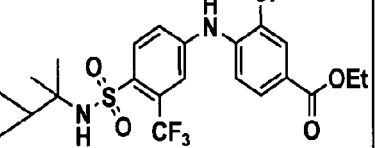 | | | | |
| 82 | 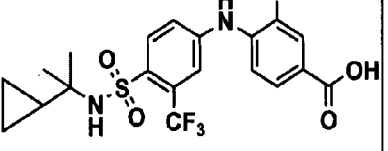 | | | 1253 | 672 |
| 83 | 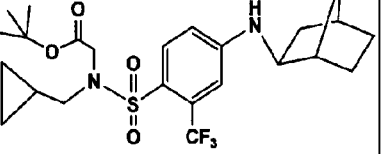 | | | 7663 | 4107 |
| 84 | 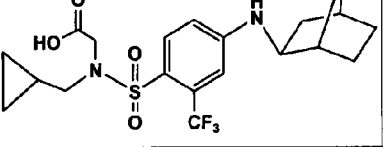 | | | NB | NB |
| 85 | 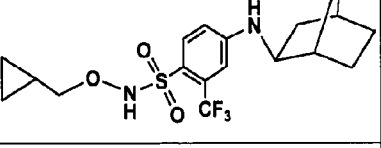 | | | 1579 | 679 |
| 85* | 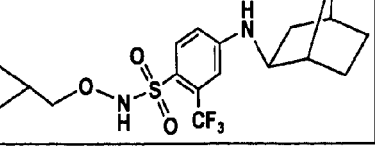 | | | 437 | 246 |

Fig. 1 (cont. 14)

| # | Structure | | | | | |
|---|---|---|---|---|---|---|
| 86 | | | | 431 | 186 | |
| 86* | | | | 467 | 264 | |
| 87 | | | | 78 | 33 | |
| 87* | | | | 37 | 23 | |
| 87* | | 6000 | 3000 | | | |
| 88 | | | | 91 | 56 | |
| 88* | | 1669 | 930 | | | |
| 89 | 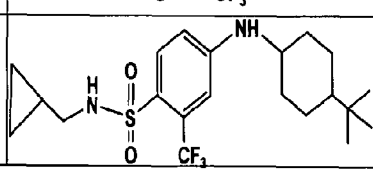 | | | 1893 | 1068 | |

Fig. 1 (cont. 15)
| # | Structure | | | | | |
|---|---|---|---|---|---|---|
| 90 | 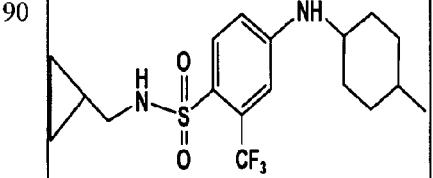 | | | 471 | 266 | |
| 90* | 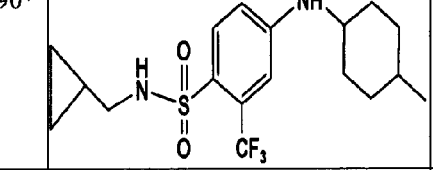 | | | 358 | 206 | |
| 91 | 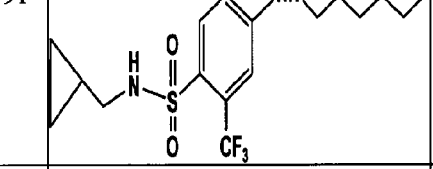 | | | 29390 | 16590 | |
| 92 | 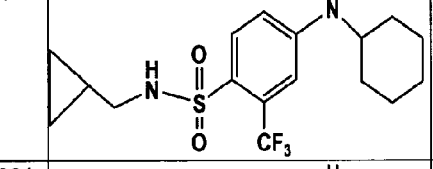 | | | 143 | 80 | |
| 92* | 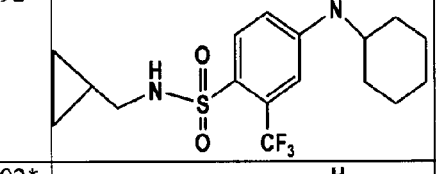 | | | 135 | 79 | |
| 92* | 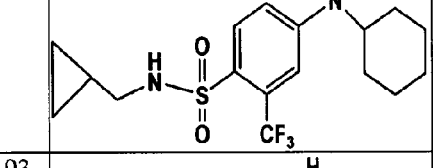 | 6000 | 3000 | | | |
| 93 | 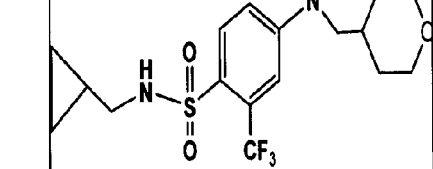 | | | 1715 | 996 | |
| 94 | 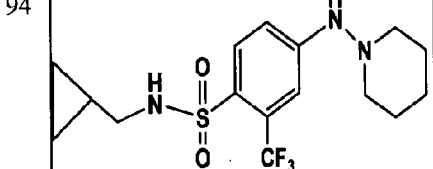 | | | 146 | 85 | |

Fig. 1 (cont. 16)

| # | Structure | | | Val1 | Val2 | |
|---|---|---|---|---|---|---|
| 94* | (structure) | 6000 | 3000 | | | |
| 95 | (structure) | | | NB | NB | |
| 96 | (structure) | | | 547 | 318 | |
| 97 | (structure) | | | 151400 | 86980 | |
| 98 | (structure) | | | 404 | 235 | |
| 99 | (structure) | | | 1599 | 919 | |
| 100 | (structure) | | | 1373 | 789 | |
| 101 | (structure) | | | 0 | NB | |

Fig. 1 (cont. 17)
| # | Structure | | | IC50 a | IC50 b | |
|---|---|---|---|---|---|---|
| 102 | 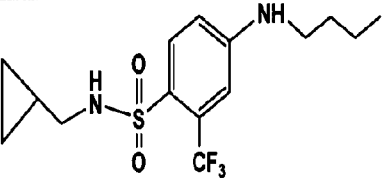 | | | 2253 | 1294 | |
| 103 | 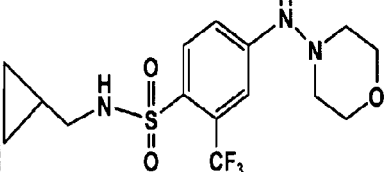 | | | 663 | 393 | |
| 104 | 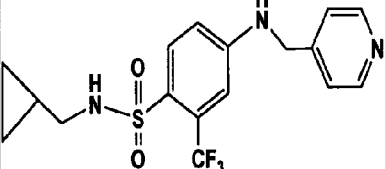 | | | 3167 | 1877 | |
| 105 | 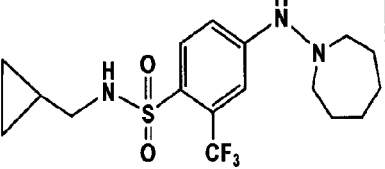 | | | 83.4 | 49 | |
| 105* | 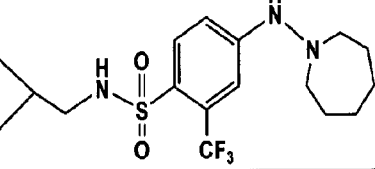 | 459 | 325 | | | |
| 106 | 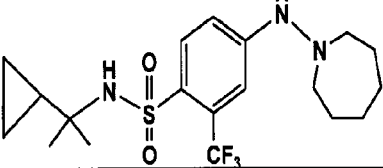 | | | 264 | 156 | |
| 107 | 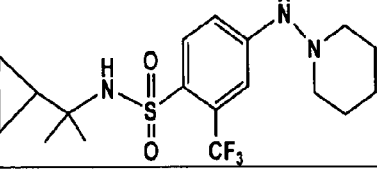 | | | 187 | 114 | |
| 108 | 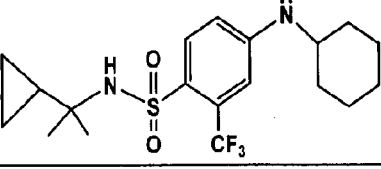 | | | 95 | 58 | |

Fig. 1 (cont. 18)

| # | Structure | | | | |
|---|---|---|---|---|---|
| 108* | [structure] | 6000 | 6000 | | |
| 109 | [structure] | | | 431 | 218 |
| 110 | [structure] | | | 37.2 | 18.8 |

\* - Multiple measurements individually presented.
NB – Non-binding.

SULFONAMIDE DERIVATIVES WITH THERAPEUTIC INDICATIONS

This application is a 371 filing of International Patent Application PCT/IL2007/001569 filed Dec. 19, 2007, which claims the benefit of application No. 60/875,536 filed Dec. 19, 2006.

FIELD OF THE INVENTION

The present invention relates to novel sulfonamide derivatives, to pharmaceutical compositions comprising the same, and to uses thereof. Compounds of the invention have a common wide range of beneficial therapeutic indications. In particular, compounds of the invention are useful analgesic and anti-inflammatory agents.

BACKGROUND OF THE INVENTION

Sulfonamide derivatives are generally formed by the reaction of an electrophilic sulfonyl derivative such as a sulfonyl halide with a nucleophilic amine. Certain benzenesulfonamide derivatives were reported to have biological effects and are used as herbicides, others have therapeutic use, for instance as analgesics, tranquilizers, anti-depressants, anxiolytics, anti-anginals, anti-bacterials, anti-virals, fungicides, anti-histaminics and anti-hypertensives.

PCT International Application No. WO 2006/048330 discloses N-benzyl sulfonamides and related derivatives as 11β-HSD1 inhibitors. The compounds are described as being useful for treating or preventing the onset of non-insulin dependent diabetes mellitus, hyperglycemia, low glucose tolerance, insulin resistance, obesity, lipid disorders, dyslipidemia, hyperlipidemia, hypertriglyceridemia, hypercholesterolemia, low HDL levels, high LDL levels, atherosclerosis and its sequelae, vascular restenosis, pancreatitis, abdominal obesity, neurodegenerative disease, retinopathy, nephropathy, neuropathy, Syndrome X, Alzheimer's disease, osteoporosis, cancer, epilepsy, depression, HAART-associated lipodystrophy and other conditions and disorders where insulin resistance is a component or that may be treated by inhibition of the 11 β-HSD 1 enzyme.

PCT International Application No. WO 03/076406 discloses sulfonamide compounds which as intermediates for the preparation of nitroso derivatives of diphenylamines.

PCT International Application No. WO 02/057240 discloses 1,2,4-triazole-3,5-diamine derivatives as kinase inhibitors.

U.S. Pat. No. 3,948,990 discloses tetrafluorophenylaminophenylsulfonyl derivatives.

U.S. Pat. No. 3,860,582 discloses and claims 4-Chloro-5-sulfamoylanthranilic acid derivatives. The compounds are described as being useful as diuretics and saluretic agents.

U.S. Pat. No. 2,373,335 describes benzene sulfonyl derivatives and their use as antioxidants.

Great Britain Patent Application No. 1,031,082 discloses and claims several tetrafluorobenzene derivatives that are described as having anticonvulsant properties.

Japanese Patent Application No. 59135255 discloses 2-(4-(disubstituted sulfamoyl)phenylamino)-6-(disubstd. amino) fluorans as color formers.

BE 629369 discloses dimethylsulfamoyl-2-anilinobenzoic acids.

Adams et al. (*Journal of the American Chemical Society* (1939), 61 2346-9) discloses several sulfanilamide derivatives and their preparation. Adams et al. (*Journal of the American Chemical Society* (1939), 61, 2464-7) discloses the preparation of optically active ethyleneimine derivatives containing an asymmetric nitrogen atom. Badetti et al. (*Synlett* (2005), (3), 449-452) describes the preparation of sulfonamides by nucleophilic aromatic substitution on 4-fluorophenylsulfonamides: nitrogen, oxygen, and sulfur nucleophiles.

Desai et al. (Journal of the Institution of Chemists (India) (1992), 64(4), 143-4) discloses 2-[N4-{N1-(n-butyl)sulfanilamido}]-4-(4'-chloroanilino)-6-(arylthioureido)-s-triazine derivatives.

Gaidukevich et al. (*Organic Reactivity* (Tartu) (1990), 27(3-4), 152-8), discusses the acid-base properties of sulfamoyl derivatives of phenylanthranilic acid in dioxane-water.

Shani et al. (Pharmacology (1983), 26(3), 172-80) discloses Structure activity correlation for diuretic furosamide congeners. Mohamed et al. (*Acta Pharmaceutica Jugoslavica* (1986), 36(3), 301-10) discloses the synthesis of chlorinated sulfonamides with expected insecticidal and antimicrobial activities.

Lin et al. (*J. Med. Chem.* (2005), 48(13), 4208-421) discloses 1-Acyl-1H-[1,2,4]triazole-3,5-diamine analogues as anticancer cyclin-dependent kinase inhibitors.

The medicinal activities exemplified above suggest that the benzenesulfonamide ring scaffold might be used as a basis for the design and preparation of novel compounds which might have therapeutic advantages.

SUMMARY OF THE INVENTION

The present invention provides new compounds, pharmaceutical compositions comprising the same and use thereof. Specifically, the new compounds of the invention are sulfonamide derivatives.

According to a first aspect, the present invention provides a compound of formula (I):

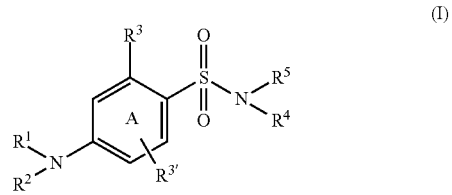

wherein:
$R^1$ is selected from the group consisting of a linear or branched, saturated or unsaturated $C_1$-$C_6$ alkyl, a saturated or unsaturated $C_3$-$C_8$ cycloalkyl, a saturated or unsaturated heterocycloalkyl, an aryl and a heteroaryl, wherein said alkyl, cycloalkyl, heterocycloalkyl, aryl or heteroaryl is unsubstituted or substituted with one or more R', wherein R' is independently at each occurrence selected from the group consisting of:
  a) a linear or branched, saturated or unsaturated $C_1$-$C_6$ alkyl,
  b) a linear or branched, saturated or unsaturated $C_1$-$C_6$ haloalkyl,
  c) a linear or branched, saturated or unsaturated $C_1$-$C_6$ alkoxy or aryloxy,
  d) a linear or branched, saturated or unsaturated $C_1$-$C_6$ haloalkoxy,
  e) a linear or branched, saturated or unsaturated $C_1$-$C_6$ alkylsulfonyl,
  f) a linear or branched, saturated or unsaturated $C_1$-$C_6$ thioalkyl or thioaryl;
  g) a saturated or unsaturated $C_3$-$C_8$ cycloalkyl, h) an aryl;
i) a heteroaryl;
j) a heterocyclyl;
k) hydroxy,
l) cyano,
m) nitro
n) halogen,
o) COR$^6$,
p) COOR$^6$,
q) CONR$^7$R$^8$, and
r) NHCOR$^9$, R$^2$ and R$^4$ are each independently selected from the group consisting of hydrogen and a linear or branched, saturated or unsaturated C$_1$-C$_6$ alkyl, wherein said alkyl is unsubstituted or substituted with one or more R", wherein R" is selected from the group consisting of:
  a) a linear or branched, saturated or unsaturated C$_1$-C$_6$ alkoxy or aryloxy,
  b) hydroxy, and
  c) a saturated or unsaturated C$_3$-C$_8$ cycloalkyl, a saturated or unsaturated heterocycloalkyl, an aryl or a heteroaryl, wherein said cycloalkyl, heterocloalkyl, aryl or heteroaryl is unsubstituted or substituted with one or more R', wherein R' is as defined above;

each of R$^3$ and R$^3'$ is independently of the other selected from the group consisting of:
  a) hydrogen;
  b) a linear or branched, saturated or unsaturated C$_1$-C$_6$ haloalkyl,
  c) a linear or branched, saturated or unsaturated C$_1$-C$_6$ haloalkoxy, and
  d) a halogen;

R$^5$ is selected from the group consisting of:
  a) a saturated or unsaturated C$_3$-C$_8$ cycloalkyl, a saturated or unsaturated heterocycloalkyl, an aryl or a heteroaryl, wherein said cycloalkyl, heterocloalkyl, aryl or heteroaryl is unsubstituted or substituted with one or more R', wherein R' is as defined above;
  b) a saturated or unsaturated, linear or branched C$_1$-C$_6$ alkyl or heteroalkyl, wherein said alkyl or heteroalkyl is unsubstituted or substituted with one or more R", wherein R" is as defined above; and
  c) a saturated or unsaturated, linear or branched C$_1$-C$_6$ alkyl as defined in b), wherein said alkyl is substituted by —COOR$_6$ or —COR$_6$;

or one or more of R$^1$ and R$^2$, or R$^4$ and R$^5$ together with the nitrogen to which they are attached form a heterocyclic or heteroaromatic ring, wherein said heterocyclic or heteroaromatic ring is unsubstituted or substituted with one or more R' wherein R' is as defined above; and R$^6$, R$^7$, R$^8$ and R$^9$ are each independently selected from the group consisting of hydrogen and a linear or branched, saturated or unsaturated C$_1$-C$_6$ alkyl; or a stereoisomer, pharmaceutically acceptable salt, ester, polymorph or solvate thereof, or a stereoisomer, pharmaceutically acceptable salt, ester, polymorph or solvate thereof.

According to one embodiment, the present invention provides a compound of formula (I) with the proviso that at least one of R3 and R3' is other than hydrogen. According to another embodiment, formula (I) excludes the compound 4-cyano-2',5'-dichloro-4(4-morpholinosulphonyl)-2,3,5,6-tetrafluorophenylamine.

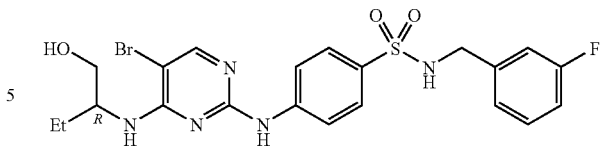

According to certain embodiments, the present invention provides a compound of formula (I) wherein R$^1$ is selected from the group consisting of a linear or branched, saturated or unsaturated C$_1$-C$_6$ alkyl, phenyl, cyclohexyl, norbornanyl, and pyrimidinyl, wherein said alkyl, phenyl, cyclohexyl, norbornanyl, and pyrimidinyl are each independently unsubstituted or substituted by one or more R', wherein R' is as defined above. According to exemplary embodiments, each R' is independently selected from the group consisting of a linear or branched, saturated or unsaturated C$_{1-6}$ alkoxy, a saturated or unsaturated C$_3$-C$_8$ cycloalkyl, a heterocyclyl, cyano and a halogen According to other exemplary embodiments, the present invention provides a compound of formula (I) wherein R$^1$ is selected from the group consisting of 2,4-dichlorophenyl, 3,5-dimethoxyphenyl, 2,4-dimethoxyphenyl, 4-morpholin-4-ylphenyl, 2,3-dihydro-benzo[1.4]dioxin-6-yl, 4-methoxyphenyl, phenyl, 2,4-difluorophenyl, 4,6-dimethoxy pyrimidinyl, cyclohexyl, norbornanyl, propyl, Cyclopropylmethyl and 2-chloro-4-cyanophenyl.

According to certain embodiments, the present invention provides a compound of formula (I) wherein R$^2$ is hydrogen. According to other embodiments, the present invention provides a compound of formula (I) R$^2$ is selected from the group consisting of a linear or branched, saturated or unsaturated C$_1$-C$_6$ alkyl, wherein said alkyl is unsubstituted or substituted by one or more R', wherein R' is as defined above. According to exemplary embodiments, R$^2$ is selected from the group consisting of hydrogen, propyl and Cyclopropylmethyl.

According to certain embodiments, the present invention provides a compound of formula (I) wherein each of R$^3$ and R$^3'$ is independently of the other selected from the group consisting of hydrogen, a linear or branched, saturated or unsaturated C$_1$-C$_6$ haloalkyl, a linear or branched, saturated or unsaturated C$_1$-C$_6$ haloalkoxy, and a halogen. In one embodiment, R$^3$ and R$^3'$ are in the 2 and 5 positions of the benzene ring, respectively (i.e., each ortho to the sulphonyl group). In another embodiment, the present invention provides compounds of formula (I) wherein one of R$^3$ and R$^3'$ is hydrogen and the other is selected from the group consisting of a linear or branched, saturated or unsaturated C$_1$-C$_6$ haloalkyl, a linear or branched, saturated or In a currently preferred embodiment, R$^3$ is selected from the group consisting of a linear or branched, saturated or unsaturated C$_1$-C$_6$ haloalkyl, a linear or branched, saturated or unsaturated C$_1$-C$_6$ haloalkoxy, and a halogen. In another currently preferred embodiment, R$^{3'}$ is selected from the group consisting of a linear or branched, saturated or unsaturated C$_1$-C$_6$ haloalkyl, a linear or branched, saturated or unsaturated C$_1$-C$_6$ haloalkoxy, and a halogen. In another currently preferred embodiment, R$^3$ is selected from the group consisting of a linear or branched, saturated or unsaturated C$_1$-C$_6$ haloalkyl, a linear or branched, saturated or unsaturated C$_1$-C$_6$ haloalkoxy, and a halogen, and R$^{3'}$ is hydrogen. In another currently preferred embodiment, R$^{3'}$ is selected from the group consisting of a linear or branched, saturated or unsaturated C$_1$-C$_6$ haloalkyl, a linear or branched, saturated or unsaturated C$_1$-C$_6$ haloalkoxy, and a halogen, and R$^3$ is hydrogen. For purpose of illustration and not for limitation, the present invention provides compounds of formula (I) wherein each of $R^3$ and $R^{3'}$ is independently of the other selected from the group consisting of $CF_3$, $OCF_3$, F and Cl. In a currently preferred embodiment, the present invention provides compounds of formula (I) wherein $R^3$ is selected from the group consisting of $CF_3$, $OCF_3$, F and Cl and $R^{3'}$ is hydrogen. In a currently preferred embodiment, the present invention provides compounds of formula (I) wherein $R^{3'}$ is selected from the group consisting of $CF_3$, $OCF_3$, F and Cl and $R^3$ is hydrogen. In another currently preferred embodiment, the present invention provides compounds of formula (I) wherein $R^3$ is a $CF_3$ and $R^{3'}$ is hydrogen.

According to certain embodiments, the present invention provides a compound of formula (I) wherein $R^4$ is hydrogen. According to other embodiments, the present invention provides a compound of formula (I) wherein $R^4$ is selected from the group consisting of a linear or branched, saturated or unsaturated $C_1$-$C_6$ alkyl, wherein said alkyl is unsubstituted or substituted by one or more R', wherein R' is as defined above. According to exemplary embodiments, $R^4$ is selected from the group consisting of hydrogen, n-propyl and $CH_2CH_2OCH_3$.

According to certain embodiments, the present invention provides a compound of formula (I) wherein $R^5$ is selected from the group consisting of a saturated or unsaturated, linear or branched $C_1$-$C_6$ alkyl or heteroalkyl, wherein said alkyl or heteroalkyl is unsubstituted or substituted with one or more R", wherein R" is as defined above. According to exemplary embodiments, the present invention provides a compound of formula (I) wherein $R^5$ is selected from the group consisting of $CH_2CH_2$-morpholinyl, $CH_2$-benzo[1,3]dioxolanyl, Cyclopropylmethyl, $CH_2$-tetrahydrofuranyl, $CH_2$-furanyl. $CH_2$-tetrahydropyranyl, n-butyl, $CH_2CH_2$—$OCH_3$, $CH_2CH_2CH_2$—$OCH_3$, $CH_2$-pyridyl and $CH_2$-morphlinyl.

According to certain embodiments, the present invention provides a compound of formula (I) wherein $R^1$ and $R^2$ together with the nitrogen to which they are attached form a heterocyclic or heteroaromatic ring, for example a selected from the group consisting of a morpholinyl, dihydroindolyl, quinolinyl, isoquinolinyl, pyrazolyl, imidazolyl, isoxazolyl, thiazolyl, pyrrolyl, aziridinyl, azetidinyl, pyrrolidinyl, morpholinyl, piperazinyl, piperidinyl, tetrahydropyridinyl, azepinyl, oxapinyl, azacyclooctanyl, azaoxacyclooctanyl and azathiacyclooctanyl ring. According to other embodiments, the present invention provides a compound of formula (I) wherein $R^4$ and $R^5$ together with the nitrogen to which they are attached form a heterocyclic or heteroaromatic ring, for example a selected from the group consisting of a morpholinyl, dihydroindolyl, quinolinyl, isoquinolinyl, pyrazolyl, imidazolyl, isoxazolyl, thiazolyl, pyrrolyl, aziridinyl, azetidinyl, pyrrolidinyl, morpholinyl, piperazinyl, piperidinyl, tetrahydropyridinyl, azepinyl, oxapinyl, azacyclooctanyl, azaoxacyclooctanyl and azathiacyclooctanyl.

In another embodiment, the present invention provides compounds selected from the group consisting of:
a. 4-(2,4-dichloro-phenylamino)-N-(2-morpholin-4-yl-ethyl)-2-trifluoromethyl-benzenesulfonamide
b. N-Benzo[1,3]dioxol-5-ylmethyl-4-(2,4-dichloro-phenylamino)-2-trifluoromethyl-benzenesulfonamide;
c. N-Cyclopropylmethyl-4-(2,4-dichloro-phenylamino)-2-trifluoromethyl-benzenesulfonamide;
d. N-Cyclopropylmethyl-4-(3,5-dimethoxy-phenylamino)-2-trifluoromethyl-benzenesulfonamide;
e. N-cyclopropylmethyl-4-(4-methoxy-phenylamino)-2-trifluoromethyl-benzenesulfonamide;
f. N-Cyclopropylmethyl-4-phenylamino-2-trifluoromethyl-benzenesulfonamide;
g. 4-(2,4-Dichloro-phenylamino)-N-(tetrahydro-furan-2-ylmethyl)-2-trifluoromethyl-benzenesulfonamide;
h. N-Butyl-4-(2,4-dichloro-phenylamino)-2-trifluoromethyl-benzenesulfonamide;
i. N-Cyclopropylmethyl-4-(3,5-dimethoxy-phenylamino)-2-trifluoromethoxy-benzenesulfonamide;
j. N-Cyclopropylmethyl-4-(3,5-dimethoxy-phenylamino)-benzenesulfonamide;
k. 4-(2,4-Difluoro-phenylamino)-N-(tetrahydro-furan-2-ylmethyl)-2-trifluoromethyl-benzenesulfonamide;
l. N-Cyclopropylmethyl-4-(4,6-dimethoxy-pyrimidin-2-ylamino)-2-trifluoromethyl-benzenesulfonamide;
m. 4-(3,5-Dimethoxy-phenylamino)-2-fluoro-N-(tetrahydro-furan-2-ylmethyl)-benzenesulfonamide;
n. 4-(3,5-Dimethoxy-phenylamino)-3-fluoro-N-(tetrahydro-furan-2-ylmethyl)-benzenesulfonamide;
o. 4-(3,5-Dimethoxy-phenylamino)-2,5-difluoro-N-(tetrahydro-furan-2-ylmethyl)-benzenesulfonamide;
p. 4-(3,5-Dimethoxy-phenylamino)-N-(3-methoxy-propyl)-2-trifluoromethyl-benzenesulfonamide;
q. 4-(3,5-Dimethoxy-phenylamino)-N-(tetrahydro-furan-2-ylmethyl)-2-trifluoromethyl-benzenesulfonamide;
r. 4-(3,5-Dimethoxy-phenylamino)-N-pyridin-4-ylmethyl-2-trifluoromethyl-benzenesulfonamide;
s. (3,5-Dimethoxy-phenyl)-[4-(morpholine-4-sulfonyl)-3-trifluoromethyl-phenyl]-amine;
t. 4-(3,5-Dimethoxy-phenylamino)-N-(2-morpholin-4-yl-ethyl)-2-trifluoromethyl-benzenesulfonamide;
u. 4-Cyclohexylamino-N-(tetrahydro-furan-2-ylmethyl)-2-trifluoromethyl-benzenesulfonamide;
v. 4-(Bicyclo[2.2.1]hept-2-ylamino)-N-(tetrahydro-furan-2-ylmethyl)-2-trifluoromethyl-benzenesulfonamide;
w. 2-Chloro-4-(3,5-dimethoxy-phenylamino)-N-(tetrahydro-furan-2-ylmethyl)-benzenesulfonamide;
x. 2,6-Dichloro-4-(3,5-dimethoxy-phenylamino)-N-(tetrahydro-furan-2-ylmethyl)-benzenesulfonamide;
y. 4-(3,5-Dimethoxy-phenylamino)-N-furan-2-ylmethyl-2-trifluoromethyl-benzenesulfonamide;
z. 4-(3,5-Dimethoxy-phenylamino)-N-isoquinolin-5-yl-2-trifluoromethyl-benzenesulfonamide;
aa. 4-(2,3-Dihydro-indol-1-yl)-N-(tetrahydro-furan-2-ylmethyl)-2-trifluoromethyl-benzenesulfonamide;
bb. 4-(Cyclopropylmethyl-propyl-amino)-N-(tetrahydro-furan-2-ylmethyl)-2-trifluoromethyl-benzenesulfonamide;
cc. [4-(2,3-Dihydro-indole-1-sulfonyl)-3-trifluoromethyl-phenyl]-(3,5-dimethoxy-phenyl)-amine;
dd. 4-(3,5-Dimethoxy-phenylamino)-N,N-bis-(2-methoxy-ethyl)-2-trifluoromethyl-benzenesulfonamide;
ee. 4-(2,4-Dichloro-phenylamino)-N-(tetrahydro-pyran-4-ylmethyl)-2-trifluoromethyl-benzenesulfonamide;
ff. N-Cyclopropylmethyl-4-(2,4-difluoro-phenylamino)-2-trifluoromethyl-benzenesulfonamide;
gg. 4-(2,4-Difluoro-phenylamino)-N-furan-2-ylmethyl-benzenesulfonamide;
hh. 4-(2,4-Difluoro-phenylamino)-N-furan-2-ylmethyl-2-trifluoromethyl-benzenesulfonamide;
ii. N-Cyclopropylmethyl-4-(2,4-difluoro-phenylamino)-benzenesulfonamide;
jj. 4-(Bicyclo[2.2.1]hept-2-ylamino)-N-cyclopropylmethyl-benzenesulfonamide;
kk. 4-(Bicyclo[2.2.1]hept-2-ylamino)-N-(tetrahydro-pyran-4-ylmethyl)-2-trifluoromethyl-benzenesulfonamide;
ll. 4-(Bicyclo[2.2.1]hept-2-ylamino)-N-furan-2-ylmethyl-2-trifluoromethyl-benzenesulfonamide;

mm. 4-(2-Chloro-4-cyano-phenylamino)-N-cyclopropyl-methyl-2-trifluoromethyl-benzenesulfonamide;
nn. N-cyclopropylmethyl-4-(2,4-dimethoxy-phenylamino)-2-trifluoromethyl-benzenesulfonamide;
oo. N-cyclopropylmethyl-4-(2,4-dimethoxy-phenylamino)-N-propyl-2-trifluoromethyl-benzenesulfonamide;
pp. N-cyclopropylmethyl-4-(4-morpholin-4-yl-phenylamino)-2-trifluoromethyl-benzenesulfonamide; and
qq. N-cyclopropylmethyl-4-(2,3-dihydro-benzo[1.4]dioxin-6-ylamino)-2-trifluoromethyl-benzenesulfonamide.

The compounds of the invention can possess one or more chiral centers, and can therefore be produced as individual stereoisomers such as enantiomers and diastereomers or as mixtures, e.g. racemic mixtures, enantiomerically enriched mixtures, diastereomerically enriched mixtures, or mixture containing equal amounts of diastereomers, depending on synthetic conditions and appropriate separation and isolation. All of these individual stereoisomers or mixtures thereof are intended to be included within the scope of the present invention.

The compounds of the invention can be used for the preparation of a medicament either as the sole active ingredient, as is or in the form of their pharmaceutically acceptable salts, esters, polymorphs, solvates and derivatives, or in appropriate combination with one or more other compounds of the present invention or with one or more other active ingredients.

According to a further aspect, the present invention provides a pharmaceutical composition comprising a prophylactically and/or therapeutically effective amount of a compound of formula (I):

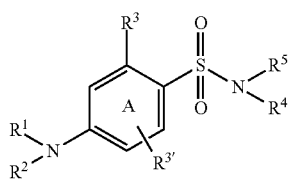

wherein:
$R^1$ is selected from the group consisting of a linear or branched, saturated or unsaturated $C_1$-$C_6$ alkyl, a saturated or unsaturated $C_3$-$C_8$ cycloalkyl, a saturated or unsaturated heterocycloalkyl, an aryl and a heteroaryl, wherein said alkyl, cycloalkyl, heterocycloalkyl, aryl or heteroaryl is unsubstituted or substituted with one or more R', wherein R' is independently at each occurrence selected from the group consisting of:
  a) a linear or branched, saturated or unsaturated $C_1$-$C_6$ alkyl,
  b) a linear or branched, saturated or unsaturated $C_1$-$C_6$ haloalkyl,
  c) a linear or branched, saturated or unsaturated $C_1$-$C_6$ alkoxy or aryloxy,
  d) a linear or branched, saturated or unsaturated $C_1$-$C_6$ haloalkoxy,
  e) a linear or branched, saturated or unsaturated $C_1$-$C_6$ alkylsulfonyl,
  f) a linear or branched, saturated or unsaturated $C_1$-$C_6$ thioalkyl or thioaryl;
  g) a saturated or unsaturated $C_3$-$C_8$ cycloalkyl,
  h) an aryl;
  i) a heteroaryl;
  j) a heterocyclyl;
  k) hydroxy,
  l) cyano,
  m) nitro
  n) halogen,
  o) $COR^6$,
  p) $COOR^6$,
  q) $CONR^7R^8$, and
  r) $NHCOR^9$,
$R^2$ and $R^4$ are each independently selected from the group consisting of hydrogen and a linear or branched, saturated or unsaturated $C_1$-$C_6$ alkyl, wherein said alkyl is unsubstituted or substituted with one or more R", wherein R" is selected from the group consisting of:
  a) a linear or branched, saturated or unsaturated $C_1$-$C_6$ alkoxy or aryloxy,
  b) hydroxy, and
  c) a saturated or unsaturated $C_3$-$C_8$ cycloalkyl, a saturated or unsaturated heterocycloalkyl, an aryl or a heteroaryl, wherein said cycloalkyl, heterocycloalkyl, aryl or heteroaryl is unsubstituted or substituted with one or more R', wherein R' is as defined above;
each of $R^3$ and $R^{3'}$ is independently of the other selected from the group consisting of:
  a) hydrogen;
  b) a linear or branched, saturated or unsaturated $C_1$-$C_6$ haloalkyl,
  c) a linear or branched, saturated or unsaturated $C_1$-$C_6$ haloalkoxy, and
  d) a halogen;
$R^5$ is selected from the group consisting of:
  a) a saturated or unsaturated $C_3$-$C_8$ cycloalkyl, a saturated or unsaturated heterocycloalkyl, an aryl or a heteroaryl, wherein said cycloalkyl, heterocycloalkyl, aryl or heteroaryl is unsubstituted or substituted with one or more R', wherein R' is as defined above;
  b) a saturated or unsaturated, linear or branched $C_1$-$C_6$ alkyl or heteroalkyl, wherein said alkyl or heteroalkyl is unsubstituted or substituted with one or more R", wherein R" is as defined above; and
  c) a saturated or unsaturated, linear or branched $C_1$-$C_6$ alkyl as defined in b), wherein said alkyl is substituted by —$COOR_6$ or —$COR_6$;
or one or more of $R^1$ and $R^2$, or $R^4$ and $R^5$ together with the nitrogen to which they are attached form a heterocyclic or heteroaromatic ring, wherein said heterocyclic or heteroaromatic ring is unsubstituted or substituted with one or more R' wherein R' is as defined above; and
$R^6$, $R^7$, $R^8$ and $R^9$ are each independently selected from the group consisting of hydrogen and a linear or branched, saturated or unsaturated $C_1$-$C_6$ alkyl;
or a stereoisomer, pharmaceutically acceptable salt, ester, polymorph or solvate thereof.

According to one embodiment, the present invention provides a pharmaceutical composition comprising a compound of formula (I) with the proviso that at least one of $R^3$ and $R^{3'}$ is other than hydrogen. According to another embodiment, formula (I) excludes the compound 4-cyano-2',5'-dichloro-4(4-morpholinosulphonyl)-2,3,5,6-tetrafluorophenyl amine.

In certain embodiments, the present invention provides a pharmaceutical composition comprising, as an active ingredient, at least one compound selected from the group consisting of compounds a, b, c, d, e, f, g, h, i, j, k, l, m, n, o, p, q, r, s, t, u, v, w, x, y, z, aa, bb, cc, dd, ee, ff, gg, hh, ii, jj, kk, ll, mm, nn, oo, pp and qq as set forth above.

Pharmaceutical compositions of the present invention can include in addition to the aforesaid compounds, pharmaceutically inert ingredients such as thickeners, carriers, buffers, diluents, surface active agents, preservatives and the like, all as well known in the art, necessary to produce physiologically acceptable and stable formulations.

The choice of the pharmaceutical additives, carriers, diluents, excipients and the like, will be determined in part by the particular active ingredient, as well as by the particular route of administration of the composition. The pharmaceutical compositions can be administered in a unit dosage form. The routes of administration include but are not limited to oral, aerosol, parenteral, topical, ocular, transdermal, subcutaneous, intravenous, intramuscular, intraperitoneal, intratechal, rectal and vaginal.

The pharmaceutical compositions can be in a liquid, aerosol or solid dosage form, and can be formulated into any suitable formulation including, but not limited to, solutions, suspensions, micelles, emulsions, microemulsions, aerosols, powders, granules, sachets, soft gels, capsules, tablets, pills, caplets, suppositories, creams, gels, pastes, foams and the like, as will be required by the particular route of administration.

According to specific embodiments, the pharmaceutical compositions of the present invention comprise as a carrier an aqueous solution comprising a pharmaceutically acceptable cosolvent, a micellar solution or emulsion prepared with natural or synthetic ionic or non-ionic surfactants, or a combination of such cosolvent and micellar or emulsion solutions. In some embodiments, the pharmaceutical compositions comprise as a carrier a solution of ethanol, a surfactant and water. In other embodiments, the pharmaceutical compositions comprise as a carrier an emulsion comprising triglycerides, lecithin, glycerol, an emulsifier, and water.

In addition, the present invention provides a method of treatment which comprises acutely or chronically administering to a subject in need thereof a pharmaceutical composition comprising a prophylactically and/or therapeutically effective amount of a compound of formula (I) or any of compounds a, b, c, d, e, f, g, h, i, j, k, l, m, n, o, p, q, r, s, t, u, v, w, x, y, z, aa, bb, cc, dd, ee, ff, gg, hh, ii, jj, kk, ll, mm, nn, oo, pp and qq as defined above, either alone or in combination with one or more active ingredients.

The present invention provides pharmaceutical compositions comprising compounds of the general formula (I) or any of compounds a, b, c, d, e, f, g, h, i, j, k, l, m, n, o, p, q, r, s, t, u, v, w, x, y, z, aa, bb, cc, dd, ee, ff, gg, hh, ii, jj, kk, ll, mm, nn, oo, pp and qq as defined above for preventing, alleviating or treating inflammation, autoimmune diseases, pain, neurological disorders, neurodegenerative diseases, ocular disorders, cardiovascular disorders, appetite disorders, nausea, vomiting and certain types of cancer. In addition, the compounds prevent the progression of osteoporosis and have anabolic properties.

Examples of inflammation and autoimmune diseases include but are not limited to rheumatoid arthritis, juvenile arthritis, osteoarthritis, atherosclerosis, allergies and allergic reactions, multiple sclerosis, systemic lupus erythematosus, myasthenia gravis, diabetes mellitus type I, hepatitis, psoriasis, inflammatory bowel disease, Crohn's disease, ulcerative colitis, tissue rejection in organ transplants, malabsorption syndromes such as celiac disease, pulmonary disease such as asthma, chronic bronchitis and Sjögren's syndrome. Examples of neurological disorders include but are not limited to stroke, migraine, cluster headache, Parkinson's disease, Alzheimer's disease, amyotrophic lateral sclerosis, Huntington's chorea, prion-associated diseases, poisoning of the central nervous system, muscle spasm and tremor. Examples of pain include but are not limited to acute, chronic, peripheral, visceral, neuropathic, inflammatory and referred pain. Examples of cardiovascular disorders include but are not limited to arrhythmia, hypertension and myocardial ischemic damage. Examples of ocular disorders include but are not limited to glaucoma.

These and additional benefits and features of the invention could be better understood by those skilled in the art with reference to the following detailed description taken in conjunction with the figures and non-limiting examples.

BRIEF DESCRIPTION OF THE FIGURES

The accompanying drawings, which are incorporated in and form a part of the specification, illustrate certain embodiments of the present invention, and together with the description serve to explain the principles of the invention. In the drawings:

FIG. 1: shows in tabulated form the chemical structures of certain exemplary compounds of the invention, together with some physicochemical and biological information.

DETAILED DESCRIPTION OF THE INVENTION

Figure 2:
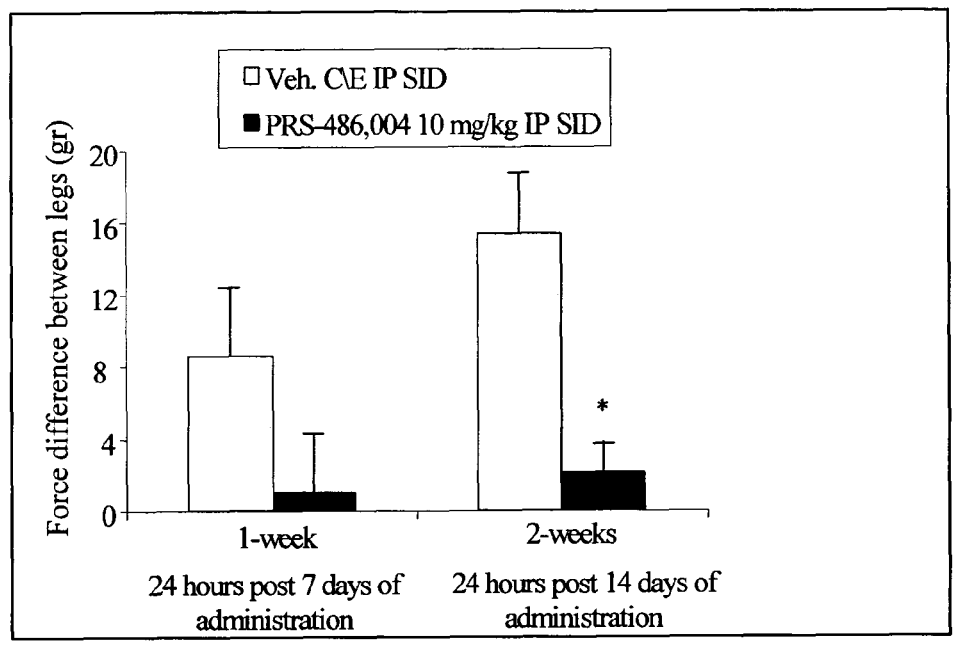
FIG. 2: shows the effect of an exemplary compound of the invention (Compound 4 administered at 10 mg/kg, s.i.d for 7 and 14 days) on CCI induced hyperalgesia.

The present invention provides new compounds, in particular sulfonamide derivatives, pharmaceutical compositions comprising the same and use thereof.

According to a first aspect, the present invention provides a compound of formula (I):

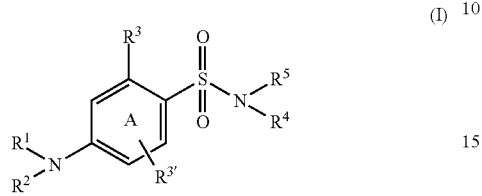

wherein:
$R^1$ is selected from the group consisting of a linear or branched, saturated or unsaturated $C_1$-$C_6$ alkyl, a saturated or unsaturated C3-C8 cycloalkyl, a saturated or unsaturated heterocycloalkyl, an aryl and a heteroaryl, wherein said alkyl, cycloalkyl, heterocycloalkyl, aryl or heteroaryl is unsubstituted or substituted with one or more R', wherein R' is independently at each occurrence selected from the group consisting of:
  a) a linear or branched, saturated or unsaturated $C_1$-$C_6$ alkyl,
  b) a linear or branched, saturated or unsaturated $C_1$-$C_6$ haloalkyl,
  c) a linear or branched, saturated or unsaturated $C_1$-$C_6$ alkoxy or aryloxy,
  d) a linear or branched, saturated or unsaturated $C_1$-$C_6$ haloalkoxy,
  e) a linear or branched, saturated or unsaturated $C_1$-$C_6$ alkylsulfonyl,
  f) a linear or branched, saturated or unsaturated $C_1$-$C_6$ thioalkyl or thioaryl;
  g) a saturated or unsaturated $C_3$-$C_8$ cycloalkyl,
  h) an aryl;
  i) a heteroaryl;
  j) a heterocyclyl;
  k) hydroxy,
  l) cyano,
  m) nitro
  n) halogen,
  o) $COR^6$,
  p) $COOR^6$,
  q) $CONR^7R^8$, and
  r) $NHCOR^9$, $R^2$ and $R^4$ are each independently selected from the group consisting of hydrogen and a linear or branched, saturated or unsaturated $C_1$-$C_6$ alkyl, wherein said alkyl is unsubstituted or substituted with one or more R", wherein R" is selected from the group consisting of:
  a) a linear or branched, saturated or unsaturated $C_1$-$C_6$ alkoxy or aryloxy,
  b) hydroxy, and
  c) a saturated or unsaturated $C_3$-$C_8$ cycloalkyl, a saturated or unsaturated heterocycloalkyl, an aryl or a heteroaryl, wherein said cycloalkyl, heterocycloalkyl, aryl or heteroaryl is unsubstituted or substituted with one or more R', wherein R' is as defined above;

each of $R^3$ and $R^{3'}$ is independently of the other selected from the group consisting of:
  a) hydrogen;
  b) a linear or branched, saturated or unsaturated $C_1$-$C_6$ haloalkyl,
  c) a linear or branched, saturated or unsaturated $C_1$-$C_6$ haloalkoxy, and
  d) a halogen;

$R^5$ is selected from the group consisting of:
  a) a saturated or unsaturated $C_3$-$C_8$ cycloalkyl, a saturated or unsaturated heterocycloalkyl, an aryl or a heteroaryl, wherein said cycloalkyl, heterocycloalkyl, aryl or heteroaryl is unsubstituted or substituted with one or more R', wherein R' is as defined above;
  b) a saturated or unsaturated, linear or branched $C_1$-$C_6$ alkyl or heteroalkyl, wherein said alkyl or heteroalkyl is unsubstituted or substituted with one or more R", wherein R" is as defined above; and
  c) a saturated or unsaturated, linear or branched $C_1$-$C_6$ alkyl as defined in b), wherein said alkyl is substituted by —$COOR_6$ or —$COR_6$;

or one or more of $R^1$ and $R^2$, or $R^4$ and $R^5$ together with the nitrogen to which they are attached form a heterocyclic or heteroaromatic ring, wherein said heterocyclic or heteroaromatic ring is unsubstituted or substituted with one or more R' wherein R' is as defined above; and $R^6$, $R^7$, $R^8$ and $R^9$ are each independently selected from the group consisting of hydrogen and a linear or branched, saturated or unsaturated $C_1$-$C_6$ alkyl;

or a stereoisomer, pharmaceutically acceptable salt, ester, polymorph or solvate thereof.

According to one embodiment, the present invention provides a compound of formula (I) with the proviso that at least one of $R^3$ and $R^{3'}$ is other than hydrogen. According to another embodiment, formula (I) excludes the compound 4-cyano-2', 5'-dichloro-4(4-morpholinosulphonyl)-2,3,5,6-tetrafluorophenylamine.

According to certain embodiments, the present invention provides a compound of formula (I) wherein $R^1$ is selected from the group consisting of a linear or branched, saturated or unsaturated $C_1$-$C_6$ alkyl, phenyl, cyclohexyl, norbornanyl, and pyrimidinyl, wherein said alkyl, phenyl, cyclohexyl, norbornanyl, and pyrimidinyl are each independently unsubstituted or substituted by one or more R', wherein R' is as defined above. According to exemplary embodiments, each R' is independently selected from the group consisting of a linear or branched, saturated or unsaturated $C_{1-6}$ alkoxy (e.g., methoxy, or when there is more than one R', each R' can be an alkoxy, e.g., methoxy, or the two alkoxy groups can further be linked to form a second cyclic structure, e.g., dihydro-benzo[1.4]dioxin-6-yl), a saturated or unsaturated $C_3$-$C_8$ cycloalkyl (e.g., cyclopropyl), heterocyclyl (e.g., morpholinyl), cyano and a halogen.

According to other exemplary embodiments, the present invention provides a compound of formula (I) wherein $R^1$ is selected from the group consisting of 2,4-dichlorophenyl, 3,5-dimethoxyphenyl, 2,4-dimethoxyphenyl, 4-morpholin-4-ylphenyl, 2,3-dihydro-benzo[1.4]dioxin-6-yl, 4-methoxyphenyl, phenyl, 2,4-difluorophenyl, 4,6-dimethoxy pyrimidinyl, cyclohexyl, norbornanyl, propyl, Cyclopropylmethyl and 2-chloro-4-cyanophenyl.

According to certain embodiments, the present invention provides a compound of formula (I) wherein $R^2$ is hydrogen. According to other embodiments, the present invention provides a compound of formula (I) $R^2$ is selected from the group consisting of a linear or branched, saturated or unsaturated $C_1$-$C_6$ alkyl, wherein said alkyl is unsubstituted or substituted by one or more R', wherein R$^1$ is as defined above. According to exemplary embodiments, R$^2$ is selected from the group consisting of hydrogen, propyl and Cyclopropylmethyl.

According to certain embodiments, the present invention provides a compound of formula (I) wherein each of R$^3$ and R$^{3'}$ is independently of the other selected from the group consisting of hydrogen, a linear or branched, saturated or unsaturated C$_1$-C$_6$ haloalkyl, a linear or branched, saturated or unsaturated C$_1$-C$_6$ haloalkoxy, and a halogen. In one embodiment, R$^3$ and R$^{3'}$ are in the 2 and 5 positions of the benzene ring, respectively (i.e., each is ortho to the sulphonyl group). In another embodiment, the present invention provides compounds of formula (I) wherein one of R$^3$ and R$^{3'}$ is hydrogen and the other is selected from the group consisting of a linear or branched, saturated or unsaturated C$_1$-C$_6$ haloalkyl, a linear or branched, saturated or In a currently preferred embodiment, R$^3$ is selected from the group consisting of a linear or branched, saturated or unsaturated C$_1$-C$_6$ haloalkyl, a linear or branched, saturated or unsaturated C$_1$-C$_6$ haloalkoxy, and a halogen. In another currently preferred embodiment, R$^{3'}$ is selected from the group consisting of a linear or branched, saturated or unsaturated C$_1$-C$_6$ haloalkyl, a linear or branched, saturated or unsaturated C$_1$-C$_6$ haloalkoxy, and a halogen. In another currently preferred embodiment, R$^3$ is selected from the group consisting of a linear or branched, saturated or unsaturated C$_1$-C$_6$ haloalkyl, a linear or branched, saturated or unsaturated C$_1$-C$_6$ haloalkoxy, and a halogen, and R$^{3'}$ is hydrogen. In another currently preferred embodiment, R$^{3'}$ is selected from the group consisting of a linear or branched, saturated or unsaturated C$_1$-C$_6$ haloalkyl, a linear or branched, saturated or unsaturated C$_1$-C$_6$ haloalkoxy, and a halogen, and R$^3$ is hydrogen. For purpose of illustration and not for limitation, the present invention provides compounds of formula (I) wherein each of R$^3$ and R$^{3'}$ is independently of the other selected from the group consisting of CF$_3$, OCF$_3$, F and Cl. In a currently preferred embodiment, the present invention provides compounds of formula (I) wherein R$^3$ is selected from the group consisting of CF$_3$, OCF$_3$, F and Cl and R$^{3'}$ is hydrogen. In a currently preferred embodiment, the present invention provides compounds of formula (I) wherein R$^{3'}$ is selected from the group consisting of CF$_3$, OCF$_3$, F and Cl and R$^3$ is hydrogen. In another currently preferred embodiment, the present invention provides compounds of formula (I) wherein R$^3$ is a CF$_3$ and R$^{3'}$ is hydrogen.

According to certain embodiments, the present invention provides a compound of formula (I) wherein R$^4$ is hydrogen. According to other embodiments, the present invention provides a compound of formula (I) wherein R$^4$ is selected from the group consisting of a linear or branched, saturated or unsaturated C$_1$-C$_6$ alkyl, wherein said alkyl is unsubstituted or substituted by one or more R', wherein R' is as defined above. According to exemplary embodiments, R$^4$ is selected from the group consisting of hydrogen, n-propyl and CH$_2$CH$_2$OCH$_3$.

According to certain embodiments, the present invention provides a compound of formula (I) wherein R$^5$ is selected from the group consisting of a saturated or unsaturated, linear or branched C$_1$-C$_6$ alkyl or heteroalkyl, wherein said alkyl or heteroalkyl is unsubstituted or substituted with one or more R", wherein R" is as defined above. According to exemplary embodiments, the present invention provides a compound of formula (I) wherein R$^5$ is selected from the group consisting of CH$_2$CH$_2$-morpholinyl, CH$_2$-benzo[1,3]dioxolanyl, Cyclopropylmethyl, CH$_2$-tetrahydrofuranyl, CH$_2$-furanyl. CH$_2$-tetrahydropyranyl, n-butyl, CH$_2$CH$_2$—OCH$_3$, CH$_2$CH$_2$CH$_2$—OCH$_3$, CH$_2$-pyridyl and CH$_2$-morphlinyl. In other exemplary embodiments, R$^5$ is selected from the group consisting of methylene (CH$_2$) bonded to a cyclic moiety selected from the group consisting of: aziridinyl, 2- or 3-azetidinyl, oxetanyl, thioxetanyl, thioxetanyl-s-oxide, thioxetanyl-s,s-dioxide, dioxalanyl, pyrrolidinyl, tetrahydrofuranyl, tetrahydrothiophenyl, morpholinyl, piperidinyl piperizinyl, piperidinyl, tetrahydropyranyl, tetrahydrothiopyranyl, thiomorpholinyl, thiomorpholinyl-s,s-dioxide, tetrahydropyridinyl, azapine, oxapine, azacyclooctanyl, azaoxacyclooctanyl, azathiacyclooctanyl, oxacyclooctanyl, thiacyclooctanyl, a C$_3$-C$_8$ cycloalkyl group, a straight or branched C$_{1-10}$ alkyl, a C$_{5-7}$ cycloalkenyl, any of which can be unsubstituted or substituted by one, two or three substituents selected from C$_{1-6}$ alkyl, C$_{1-6}$ alkoxy, a hydroxy group, a cyano group, halo, sulfonyl group, methylsulfonyl, NR$^7$R$^8$, NHCOCH$_3$, (=O), and —CONHCH$_3$.

According to certain embodiments, the present invention provides a compound of formula (I) wherein R$^1$ and R$^2$ together with the nitrogen to which they are attached form a heterocyclic or heteroaromatic ring, for example a selected from the group consisting of a morpholinyl, dihydroindolyl, quinolinyl, isoquinolinyl, pyrazolyl, imidazolyl, isoxazolyl, thiazolyl, pyrrolyl, aziridinyl, azetidinyl, pyrrolidinyl, morpholinyl, piperazinyl, piperidinyl, tetrahydropyridinyl, azepinyl, oxapinyl, azacyclooctanyl, azaoxacyclooctanyl and azathiacyclooctanyl ring. According to other embodiments, the present invention provides a compound of formula (I) wherein R$^4$ and R$^5$ together with the nitrogen to which they are attached form a heterocyclic or heteroaromatic ring, for example a selected from the group consisting of a morpholinyl, dihydroindolyl, quinolinyl, isoquinolinyl, pyrazolyl, imidazolyl, isoxazolyl, thiazolyl, pyrrolyl, aziridinyl, azetidinyl, pyrrolidinyl, morpholinyl, piperazinyl, piperidinyl, tetrahydropyridinyl, azepinyl, oxapinyl, azacyclooctanyl, azaoxacyclooctanyl and azathiacyclooctanyl. Any of the above heterocyclic or heteroaromatic rings can be unsubstituted, or substituted with at least one group selected from the group consisting of C$_{1-6}$ alkyl, C$_{1-6}$ alkoxy, a hydroxyl group, a cyano group, halo, sulfonyl group, methylsulfonyl, NR$^7$R$^8$, NHCOCH$_3$, (=O), and —CONHCH$_3$.

According to certain embodiments, the present invention provides a compound selected from the group consisting of:
a. 4-(2,4-dichloro-phenylamino)-N-(2-morpholin-4-yl-ethyl)-2-trifluoromethyl-benzenesulfonamide;
b. N-Benzo[1,3]dioxol-5-ylmethyl-4-(2,4-dichloro-phenylamino)-2-trifluoromethyl-benzenesulfonamide;
c. N-Cyclopropylmethyl-4-(2,4-dichloro-phenylamino)-2-trifluoromethyl-benzenesulfonamide;
d. N-Cyclopropylmethyl-4-(3,5-dimethoxy-phenylamino)-2-trifluoromethyl-benzenesulfonamide;
e. N-cyclopropylmethyl-4-(4-methoxy-phenylamino)-2-trifluoromethyl-benzenesulfonamide;
f. N-Cyclopropylmethyl-4-phenylamino-2-trifluoromethyl-benzenesulfonamide;
g. 4-(2,4-Dichloro-phenylamino)-N-(tetrahydro-furan-2-ylmethyl)-2-trifluoromethyl-benzenesulfonamide;
h. N-Butyl-4-(2,4-dichloro-phenylamino)-2-trifluoromethyl-benzenesulfonamide;
i. N-Cyclopropylmethyl-4-(3,5-dimethoxy-phenylamino)-2-trifluoromethoxy-benzenesulfonamide;
j. N-Cyclopropylmethyl-4-(3,5-dimethoxy-phenylamino)-benzenesulfonamide;
k. 4-(2,4-Difluoro-phenylamino)-N-(tetrahydro-furan-2-ylmethyl)-2-trifluoromethyl-benzenesulfonamide;
l. N-Cyclopropylmethyl-4-(4,6-dimethoxy-pyrimidin-2-ylamino)-2-trifluoromethyl-benzenesulfonamide;

m. 4-(3,5-Dimethoxy-phenylamino)-2-fluoro-N-(tetrahydro-furan-2-ylmethyl)-benzenesulfonamide;
n. 4-(3,5-Dimethoxy-phenylamino)-3-fluoro-N-(tetrahydro-furan-2-ylmethyl)-benzenesulfonamide;
o. 4-(3,5-Dimethoxy-phenylamino)-2,5-difluoro-N-(tetrahydro-furan-2-ylmethyl)-benzenesulfonamide;
p. 4-(3,5-Dimethoxy-phenylamino)-N-(3-methoxy-propyl)-2-trifluoromethyl-benzenesulfonamide;
q. 4-(3,5-Dimethoxy-phenylamino)-N-(tetrahydro-furan-2-ylmethyl)-2-trifluoromethyl-benzenesulfonamide;
r. 4-(3,5-Dimethoxy-phenylamino)-N-pyridin-4-ylmethyl-2-trifluoromethyl-benzenesulfonamide;
s. (3,5-Dimethoxy-phenyl)-[4-(morpholine-4-sulfonyl)-3-trifluoromethyl-phenyl]-amine;
t. 4-(3,5-Dimethoxy-phenylamino)-N-(2-morpholin-4-yl-ethyl)-2-trifluoromethyl-benzenesulfonamide;
u. 4-Cyclohexylamino-N-(tetrahydro-furan-2-ylmethyl)-2-trifluoromethyl-benzenesulfonamide;
v. 4-(Bicyclo[2.2.1]hept-2-ylamino)-N-(tetrahydro-furan-2-ylmethyl)-2-trifluoromethyl-benzenesulfonamide;
w. 2-Chloro-4-(3,5-dimethoxy-phenylamino)-N-(tetrahydro-furan-2-ylmethyl)-benzenesulfonamide;
x. 2,6-Dichloro-4-(3,5-dimethoxy-phenylamino)-N-(tetrahydro-furan-2-ylmethyl)-benzenesulfonamide;
y. 4-(3,5-Dimethoxy-phenylamino)-N-furan-2-ylmethyl-2-trifluoromethyl-benzenesulfonamide;
z. 4-(3,5-Dimethoxy-phenylamino)-N-isoquinolin-5-yl-2-trifluoromethyl-benzenesulfonamide;
aa. 4-(2,3-Dihydro-indol-1-yl)-N-(tetrahydro-furan-2-ylmethyl)-2-trifluoromethyl-benzenesulfonamide;
bb. 4-(Cyclopropylmethyl-propyl-amino)-N-(tetrahydro-furan-2-ylmethyl)-2-trifluoromethyl-benzenesulfonamide;
cc. [4-(2,3-Dihydro-indole-1-sulfonyl)-3-trifluoromethyl-phenyl]-(3,5-dimethoxy-phenyl)-amine;
dd. 4-(3,5-Dimethoxy-phenylamino)-N,N-bis-(2-methoxy-ethyl)-2-trifluoromethyl-benzenesulfonamide;
ee. 4-(2,4-Dichloro-phenylamino)-N-(tetrahydro-pyran-4-ylmethyl)-2-trifluoromethyl-benzenesulfonamide;
ff. N-Cyclopropylmethyl-4-(2,4-difluoro-phenylamino)-2-trifluoromethyl-benzenesulfonamide;
gg. 4-(2,4-Difluoro-phenylamino)-N-furan-2-ylmethyl-benzenesulfonamide;
hh. 4-(2,4-Difluoro-phenylamino)-N-furan-2-ylmethyl-2-trifluoromethyl-benzenesulfonamide;
ii. N-Cyclopropylmethyl-4-(2,4-difluoro-phenylamino)-benzenesulfonamide;
jj. 4-(Bicyclo[2.2.1]hept-2-ylamino)-N-cyclopropylmethyl-benzenesulfonamide;
kk. 4-(Bicyclo[2.2.1]hept-2-ylamino)-N-(tetrahydro-pyran-4-ylmethyl)-2-trifluoromethyl-benzenesulfonamide;
ll. 4-(Bicyclo[2.2.1]hept-2-ylamino)-N-furan-2-ylmethyl-2-trifluoromethyl-benzenesulfonamide;
mm. 4-(2-Chloro-4-cyano-phenylamino)-N-cyclopropylmethyl-2-trifluoromethyl-benzenesulfonamide;
nn. N-cyclopropylmethyl-4-(2,4-dimethoxy-phenylamino)-2-trifluoromethyl-benzenesulfonamide;
oo. N-cyclopropylmethyl-4-(2,4-dimethoxy-phenylamino)-N-propyl-2-trifluoromethyl-benzenesulfonamide;
pp. N-cyclopropylmethyl-4-(4-morpholin-4-yl-phenylamino)-2-trifluoromethyl-benzenesulfonamide; and
qq. N-cyclopropylmethyl-4-(2,3-dihydro-benzo[1.4]dioxin-6-ylamino)-2-trifluoromethyl-benzenesulfonamide.

DEFINITIONS

To facilitate an understanding of the present invention, a number of terms and phrases are defined below.

As used herein, the term "central nervous system" (CNS) refers to all structures within the dura mater. Such structures include, but are not limited to, the brain and spinal cord.

As used herein, the term "CB" refers to cannabinoid receptors. $CB_1$ receptors are predominantly found in the CNS, whereas $CB_2$ receptors are predominantly found in the periphery on immune cells. Aside from these two receptors, evidence exists supporting the presence of yet uncloned cannabinoid receptors.

As used herein, the term "cannabinoid" or "cannabinoids" refers to natural, plant derived or endogenous, or synthetic compounds, metabolites and analogues thereof, whose effects are generally mediated by cannabinoid receptors, but can also act through cannabinoid receptor independent mechanisms.

In the present invention, binding affinity is represented as indicated either by the $IC_{50}$ value, namely the concentration of a test compound that will displace 50% of a radiolabeled agonist from the CB receptors, or by the dissociation constant $K_i$, which represents the concentration of the unlabelled drug that will bind to half the binding sites at equilibrium in the absence of radioligand. The $K_i$ value is calculated based on the $IC_{50}$ value of the test compound and the radioligand concentration and its dissociation constant $K_d$. Compounds specific for a given receptor display $K_i$ value for binding of said receptor of 50 nM or lower, preferably of 30 nM or lower, more preferably of 10 nM or lower and most preferably of 1 nM or lower. Compounds selective for a given receptor display a ratio of binding affinity between the receptors under consideration of at least 5, preferably 10, more preferably 20 and most preferably 50 or greater. Preferably these ratios will be obtained for human $CB_1$ and $CB_2$ receptors. Compounds of the present invention may or may not exhibit binding affinity toward each cannabinoid receptor, as well as may or may not display selectivity toward one of the receptors.

An agonist is a substance that mimics a specific ligand, for example a hormone, a neurotransmitter, or in the present case a cannabinoid, able to attach to that ligand's receptor and thereby produce the same action that the natural ligand produces. Though most agonists act through direct binding to the relevant receptor and subsequent activation, some agonists act by promoting the binding of the ligand or increasing its time of residence on the receptor, increasing the probability and effect of each coupling. Compounds that have the opposite effect, and instead of promoting the action of a ligand, block it, are receptor antagonists. The novel sulfonamide derivatives described herein that interact with at least one cannabinoid receptor can initiate either an agonistic or an antagonistic response from said receptor, and both mechanisms of action are encompassed in the present inventions.

Though the most probable mechanism of action of the compounds of the invention is through their binding to the known cannabinoid receptors and functional coupling to or blocking of specific signal transduction pathways, alternative mechanisms cannot be ruled out, for instance either through binding to additional yet unidentified cannabinoid receptors or through non-cannabinoid receptor or non-receptor mediated means, or a combination of such mechanisms. The applicants of the present invention do not wish to be bound by any particular theory or mechanism of action through which the compounds of the present invention exert their therapeutic effect.

Though the most probable mechanism of action of the compounds of the invention is through their modulation of inflammatory/immune mechanisms, the applicants of the present invention do not wish to be bound by any particular theory or mechanism of action through which the compounds of the present invention exert their therapeutic effect.

In the present specification and claims which follow "inhibiting, reducing, or decreasing effect" means the ability to reduce the activity under discussion by at least 20%, preferably 40%, more preferably 60% and most preferably 80% or greater. In case of activities wherein the maximal possible effect is not 100%, the previous figures relate to percent of maximal possible effect.

In the present specification and claims which follow "enhancing or increasing effect" means the ability to increase the activity under discussion by at least about 1.5 fold, preferably about 3 folds, more preferably about 4 folds and most preferably above 5 folds or more.

CHEMICAL DEFINITIONS

Some of the compounds according to the invention can exist in stereoisomeric forms which either are related as image and mirror image (enantiomers) or are not related as image and mirror image (diastereomers). The invention relates to the individual enantiomers or diastereomers or respective mixtures thereof, racemic mixtures, enantiomerically enriched mixtures, diastereomerically enriched mixtures, or mixture containing equal amounts of diastereomers. These mixtures of enantiomers and diastereomers can be separated into stereoisomerically uniform components in a known manner or synthesized a priori as separate enantiomers or diastereomers. All of these individual stereoisomers or mixtures thereof are intended to be included within the scope of the present invention.

The alkyl substituents can be saturated or unsaturated (e.g, alkenyl, alkynyl), linear or branched. When unsaturated, the hydrocarbon radicals can have one double bond or more and form alkenyls, or one triple bond or more and form alkynyls. Regardless of the degree of unsaturation, all of the alkyl substituents can be linear or branched. The alkyl substituents can contain between 1 and 12 carbon atoms in the main alkyl chain (designated herein $C_1$-$C_{12}$). For example the alkyl can contain one carbon atom ($C_1$), four carbon atoms ($C_4$), six carbon atoms ($C_6$) and the like. Representative alkyl groups include, but are not limited to, methyl, ethyl, propyl, isopropyl, butyl, sec-butyl, tert-butyl, pentyl, isopentyl, neopentyl, hexyl, isohexyl, and neohexyl. The term "$C_1$-$C_6$ alkyl" refers to a straight or branched chain alkane (hydrocarbon) radical containing from 1 to 6 carbon atoms, such as methyl, ethyl, propyl, isopropyl, n-butyl, t-butyl, isobutyl, 1-pentyl, isopentyl, hexyl, and the like.

The term "alkenyl" as used herein refers to a linear or branched hydrocarbon having from 2 to 12 carbon atoms and having at least one carbon-carbon double bond. In one embodiment, the alkenyl has one or two double bonds. The alkenyl moiety may exist in the E or Z conformation and the compounds of the present invention include both conformations.

The term "alkynyl" as used herein refers to a linear or branched hydrocarbon having from 2 to 12 carbon atoms and having at least one carbon-carbon triple bond.

The term "aryl" refers to an aromatic cyclic hydrocarbon group of from 6 to 20 carbon atoms having a single ring (e.g., phenyl) or multiple condensed (fused) rings (e.g., naphthyl or anthryl). The term aryl includes both "unsubstituted aryls" and "substituted aryls", the latter of which refers to aryl moieties having substituents replacing a hydrogen on one or more carbons of the ring.

The term "cyclic group" as used herein includes a cycloalkyl group and a heterocyclic group.

The term "cycloalkyl group" as used herein refers to a three- to eight-membered ($C_3$-$C_8$) saturated or partially unsaturated carbon ring. Any suitable ring position of the cycloalkyl group may be covalently linked to the defined chemical structure. Exemplary cycloalkyl groups include, but are not limited to, cyclopropyl, cyclobutyl, cyclopentyl, cyclohexyl, and cycloheptyl.

The term "heterocyclic group" or "heterocyclic" or "heterocyclyl" or "heterocyclo" as used herein interchangeably, refers to fully saturated, or partially or fully unsaturated, including aromatic (i.e., "heteroaryl") cyclic groups (for example, 4 to 7 membered monocyclic, 7 to 11 membered bicyclic, or 10 to 16 membered tricyclic ring systems) which have at least one heteroatom selected from nitrogen atoms, oxygen atoms and/or sulfur atoms in the ring. Each ring of the heterocyclic group containing a heteroatom may have 1, 2, 3, or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group can be attached to the remainder of the molecule at any heteroatom or carbon atom of the ring or ring system. An exemplary embodiment includes a six-membered heteroaromatic ring, which is a monocyclic aromatic system having six ring members of which 1, 2, 3, or 4 atoms are heteroatom, for examples N, O, S, or any combination thereof. The heterocyclic system can be attached, unless otherwise stated, at any heteroatom or carbon atom which affords a stable structure. Exemplary heterocyclic groups include, but are not limited to, azepanyl, azetidinyl, aziridinyl, dioxolanyl, furanyl, furazanyl, homo piperazinyl, imidazolidinyl, imidazolinyl, isothiazolyl, isoxazolyl, morpholinyl, oxadiazolyl (e.g., 1,2,3-oxadiazolyl, 1,2,4-oxadiazolyl and 1,3,4-oxadiazolyl), oxazolidinyl, oxazolyl, oxazolidinyl, pyrimidinyl, phenanthridinyl, phenanthrolinyl, piperazinyl, piperidinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyrimidinyl, pyrrolidinyl, pyrrolinyl, quinuclidinyl, succinimidinyl, tetrahydrofuranyl, thiazolyl, thiadiazinyl, thiadiazolyl, thiadiazolyl (e.g., 1,2,3-thiadiazolyl, 1,2,4-thiadiazolyl and 1,3,4-thiadiazolyl), thienyl, thienothiazolyl, thienooxazolyl, thienoimidazolyl, thiomorpholinyl, thiophenyl, triazinyl, and triazolyl (e.g., 1,2,3-triazolyl, 1,2,4-triazolyl and 1,3,4-triazolyl). Exemplary bicyclic heterocyclic groups include indolyl, isoindolyl, benzothiazolyl, benzoxazolyl, benzoxadiazolyl, benzothienyl, quinuclidinyl, quinolinyl, tetrahydroisoquinolinyl, isoquinolinyl, benzimidazolyl, benzopyranyl, indolizinyl, benzofuryl, benzofurazanyl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl or furo[2,3-b]pyridinyl), dihydroisoindolyl, dihydroquinazolinyl (such as 3,4-dihydro-4-oxo-quinazolinyl), triazinylazepinyl, tetrahydroquinolinyl and the like. Exemplary tricyclic heterocyclic groups include carbazolyl, benzidolyl, phenanthrolinyl, acridinyl, phenanthridinyl, xanthenyl and the like.

The aforementioned terms "alkyl," "alkenyl," "alkynyl," "aryl," "phenyl," "cyclic group," "cycloalkyl," "heterocyclyl," "heterocyclo," "heterocycle" or (heteroaryls) can each, independently of the other, be unsubstituted or can further be optionally substituted with one or more substituents. Exemplary substituents include, but are not limited to, one or more of the following groups: a linear or branched, saturated or unsaturated $C_1$-$C_6$ alkyl, a linear or branched, saturated or unsaturated $C_1$-$C_6$ haloalkyl (e.g., $CF_3$), a linear or branched, saturated or unsaturated $C_1$-$C_6$ alkoxy (e.g., $OCH_3$), a linear or branched, saturated or unsaturated $C_1$-$C_6$ haloalkoxy (e.g., $OCF_3$), a linear or branched, saturated or unsaturated $C_1$-$C_6$ alkylsulfonyl, a linear or branched, saturated or unsaturated $C_1$-$C_6$ thioalkyl; a saturated or unsaturated $C_3$-$C_8$ cycloalkyl, hydroxy, cyano, nitro, halogen, $N_3$, oxo, $COR^6$, $COOR^6$, $CONR^7R^8$, $NHCOR^9$ and $NR^7NR^8$, wherein each of $R^6$, $R^7$, $R^8$ and $R^9$ are, independently of the other hydrogen and a linear or branched, saturated or unsaturated $C_1$-$C_6$ alkyl; a saturated or unsaturated C3-C8 cycloalkyl, a saturated or unsaturated heterocycloalkyl, an aryl or a heteroaryl, wherein said cycloalkyl, heterocycloalkyl, aryl or heteroaryl is unsubstituted or substituted with one or more of the substituents listed above; $OR_a$, $SR_a$, $SOR_e$, $SO_2R_e$, $PO_2R_e$, $SO_2OR_a$, $PO_2OR_a$, $NR_bSO_2R_e$, $NR_bPO_2R_e$, $SO_2NR_bR_c$, $PO_2NR_bR_c$, $OCOR_a$, $OCONR_bR_c$, $NR_bCOOR_a$, $NR_cCONR_bR_c$, $NR_dSO_2NR_bR_c$, $NR_dPO_2NR_bR_c$, $NR_bCOR_a$, or $NR_bPO_2R_e$, wherein $R_a$ is hydrogen, alkyl, cycloalkyl, alkenyl, alkynyl, alkylaryl, heteroaryl, heterocycle, or aryl; $R_b$, $R_c$ and $R_d$ are independently hydrogen, alkyl, cycloalkyl, alkylaryl, heteroaryl, heterocycle, aryl, or said $R_b$ and $R_c$ together with the N to which they are bonded optionally form a heterocycle; and $R_e$ is alkyl, cycloalkyl, alkenyl, cycloalkenyl, alkynyl, alkylaryl, heteroaryl, heterocycle, or aryl. In the aforementioned exemplary substitutents, groups such as alkyl, cycloalkyl, alkenyl, alkynyl, cycloalkenyl, alkylaryl, heteroaryl, heterocycle and aryl can themselves be optionally substituted.

"OR" represents hydroxyl or ethers, OC(O)R and C(O)OR represent esters, C(O)R represents ketones, $OC(O)NR_2$ represents carbamates, $NR_2$ represents amines, SR represents thiols or sulfides, S(O)R represents sulfoxides, S(O)(O)R represents sulfones, $P(O)(OR)_2$ represents phosphates, $OP(O)(OR)_2$ represents phosphates wherein R is hydrogen, or phosphate esters when R is an alkyl chain.

"Halogen" or "halo" means fluorine (—F), chlorine (—Cl), bromine (—Br) or iodine (—I) and if the compound contains more than one halogen (e.g., two or more variable groups can be a halogen), each halogen is independently selected from the aforementioned halogen atoms. The term "haloalkyl" refers to a halogen atom as defined herein bonded to an alkyl group as defined herein. The term "haloalkoxy" refers to an alkoxy group as defined above wherein one or more of the alkyl hydrogens has been replaced by a halogen (e.g., $OCF_3$).

The term "thio" as used herein alone or as part of another group refers to an SH group. The terms "thioalkyl", "thioaryl" (which includes "heterothioaryl") as used herein alone or as part of another group refer to any of the above alkyl, aryl or heteroaryls groups linked to a sulfur atom. The term "hydroxy" refers to an OH group. The terms "alkoxy", "aryloxy" (which includes "heteroaryloxy") as used herein alone or as part of another group includes any of the above alkyl, aryl or heteroaryl groups linked to an oxygen atom. Nonlimiting examples of an alkoxy group is methoxy, ethoxy, n-propoxy, isopropoxy, n-butoxy, t-butoxy and like groups. An example of an aryloxy group is phenyloxy (phenoxy). The alkoxy, aryloxy or heteroaryloxy groups can be unsubstituted or substituted with any one or more of the substituents defined above for alkyl.

The term "sulfonyl" as used herein alone or as part of another group refers to —S(O)$_2$. The term "alkylsulfonyl" as used herein alone or as part of another group refers to a sulfonyl group as defined herein bonded to an alkyl group as defined herein. The term "sulfonylamino" as used herein alone or as part of another group refers to —S(O)$_2$—NH. The term "sulfinyl" refers to —S(O)—. The term "sulfinylamino" as used herein alone or as part of another group refers to —S(O)—NH. The term "oxo" as used herein alone or as part of another group refers to —O—. The term "cyano" as used herein alone or as part of another group refers to a CN group. The term "nitro" as used herein alone or as part of another group refers to an $NO_2$ group.

It is to be understood that the present invention covers all combinations of particular and preferred groups mentioned hereinabove.

The term "substituted" or "optionally substituted" means that one or more hydrogens on the designated atom is replaced or optionally replaced with a selection from the indicated group, provided that the designated atom's normal valency under the existing circumstances is not exceeded. Combination of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The present invention also includes within its scope solvates of compounds of formula (I) or any of compounds a, b, c, d, e, f, g, h, i, j, k, l, m, n, o, p, q, r, s, t, u, v, w, x, y, z, aa, bb, cc, dd, ee, ff, gg, hh, ii, jj, kk, ll, mm, nn, oo, pp and qq as defined above, and salts thereof. "Solvate" means a physical association of a compound of the invention with one or more solvent molecules. This physical association involves varying degrees of ionic and covalent bonding, including hydrogen bonding. In certain instances the solvate will be capable of isolation. "Solvate" encompasses both solution-phase and isolatable solvates. Non-limiting examples of suitable solvates include ethanolates, methanolates and the like. "Hydrate" is a solvate wherein the solvent molecule is water.

The term "polymorph" refers to a particular crystalline state of a substance, which can be characterized by particular physical properties such as X-ray diffraction, IR spectra, melting point, and the like.

In the present specification the term "prodrug" represents compounds which are rapidly transformed in vivo to parent compound of formula (I) or a compound of formula compounds a, b, c, d, e, f, g, h, i, j, k, l, m, n, o, p, q, r, s, t, u, v, w, x, y, z, aa, bb, cc, dd, ee, ff, gg, hh, ii, jj, kk, ll, mm, nn, oo, pp and qq as defined above, for example by hydrolysis in the blood. Prodrugs are often useful because in some instances they can be easier to administer than the parent drug. They can, for instance, be bioavailable by oral administration whereas the parent drug is not. The prodrug can also have improved solubility compared to the parent drug in pharmaceutical compositions. All of these pharmaceutical forms are intended to be included within the scope of the present invention.

Certain compounds of the invention are capable of further forming pharmaceutically acceptable salts and esters. "Pharmaceutically acceptable salts and esters" means any salt and ester that is pharmaceutically acceptable and has the desired pharmacological properties. Such salts, formed for instance by any carboxy or sulfo groups present in the molecule, include salts that can be derived from an inorganic or organic acid, or an inorganic or organic base, including amino acids, which is not toxic or otherwise unacceptable.

Pharmaceutically acceptable acid addition salts of the compounds include salts derived from inorganic acids such as hydrochloric, nitric, phosphoric, sulfuric, hydrobromic, hydriodic, phosphorous, and the like, as well as salts derived from organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate or galacturonate (Berge S. M. et al., J. of Pharmaceutical Science, 66: 1-19, 1977, the contents of which are hereby incorporated by reference in its entirety as if fully set forth herein).

The acid addition salts of said basic compounds are prepared by contacting the free base form with a sufficient amount of the desired acid to produce the salt in the conventional manner. The free base form can be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

The base addition salts of said acidic compounds are prepared by contacting the free acid form with a sufficient amount of the desired base to produce the salt in the conventional manner. The free acid form can be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

Pharmacology

In the present specification and claims which follow the compositions comprising an effective amount of a compound of formula (I) or any of compounds a, b, c, d, e, f, g, h, i, j, k, l, m, n, o, p, q, r, s, t, u, v, w, x, y, z, aa, bb, cc, dd, ee, ff, gg, hh, ii, jj, kk, ll, mm, nn, oo, pp and qq as above defined are intended to encompass both prophylactically and therapeutically effective compositions.

The term "prophylactically effective" refers to the amount of compound which will achieve the goal of prevention, reduction or eradication of the risk of occurrence of the disease or disorder, while avoiding adverse side effects. The term "therapeutically effective" refers to the amount of compound that will achieve, with no adverse effects, alleviation, diminished progression or treatment of the disorder, once the disorder cannot be further delayed and the patients are no longer asymptomatic, hence providing either a subjective relief of a symptom(s) or an objectively identifiable improvement as noted by the clinician or other qualified observer.

The "individual" or "patient" for purposes of treatment includes any human or animal affected by any of the diseases where the treatment has beneficial therapeutic impact. Usually, the animal that serves to establish the pre-clinical data and that can be treated by compounds of the invention is a vertebrate such as a primate including chimpanzees, monkeys and macaques, a rodent including mice, rats, ferrets, rabbits and hamsters, a domestic or game animal including bovine species, equine species, pigs, sheep, caprine species, feline species, canine species, avian species, and fishes As contemplated herein, the compounds of the invention are useful in preventing, alleviating or treating indications amenable to cannabinoid intervention exemplified by pain, inflammation, immune, neurological, ocular and cardiovascular disorders, appetite stimulation, emesis, nausea, glaucoma and certain types of cancer.

By virtue of their anti-inflammatory and immunomodulatory properties, it will be recognized that the compositions according to the present invention will be useful for preventing, alleviating or treating indications having an inflammatory or autoimmune mechanism involved in their etiology or pathogenesis exemplified by arthritis, including rheumatoid arthritis, juvenile arthritis, osteoarthritis, atherosclerosis, allergies and allergic reactions, multiple sclerosis, systemic lupus erythematosus (SLE), myasthenia gravis, diabetes mellitus type I, hepatitis, psoriasis, immune related disorders including but not limited to tissue rejection in organ transplants, malabsorption syndromes such as celiac, pulmonary diseases such as asthma, chronic bronchitis and Sjögren's syndrome, inflammatory bowel disease, Crohn's disease, ulcerative colitis, and rheumatic diseases. The potential of cannabinoids as anti-inflammatory therapeutics was recently reviewed by Klein (Klein T. W., Nature Reviews Immunology 5: 400-11, 2005).

By virtue of their neuroprotective properties, it will be recognized that the compositions according to the present invention will be useful in treating neurological disorders including but not limited to stroke, migraine, and cluster headaches. The composition of the present invention can also be effective in treating certain chronic degenerative diseases that are characterized by gradual selective neuronal loss. In this connection, the compositions of the present invention are contemplated as therapeutically effective in the treatment of Parkinson's disease, Alzheimer's disease, amyotrophic lateral sclerosis, Huntington's chorea, motor disorders including spasm and tremor, and prion-associated neurodegeneration. Neuroprotection could also be effective in protection and/or treatment of neurotoxic agents, such as nerve gas, as well as other insults to brain or nervous tissue by way of chemical or biological agents.

By virtue of their analgesic properties it will be recognized that the compositions according to the present invention will be useful in treating pain including peripheral, visceral, neuropathic, inflammatory and referred pain. Some of the recent findings concerning the utility of cannabinoids as analgesics, as well as anti-inflammatory agents, were recently reviewed by Mbvundula et al. (Mbvundula E. C. et al., Inflammopharmacology 12(2): 99-114, 2004).

Another feature of the present invention is the ability of the disclosed compounds to prevent or treat certain cancers, including malignant brain tumors, skin tumors, lung adenocarcinoma, uterus, breast and prostate carcinoma, lymphoma, glioma, thyroid epithelioma, and neuroblastoma, where CB ligands can trigger apoptosis of tumor cells as well as inhibiting tumor angiogenesis. The potential of cannabinoids as anti-cancer agents was recently reviewed by Guzman (Guzman M., Nature Reviews Cancer 3: 745-55, 2003). As used herein, the term "cancer" includes both solid and non-solid tumors, as well as cancer metastasis.

Hereinafter, the term "oral administration" includes, but is not limited to, administration by mouth for absorption through the gastrointestinal tract (peroral) wherein the drug is swallowed, or for trans-mucosal absorption in the oral cavity by buccal, gingival, lingual, sublingual and oro-pharyngeal administration. Compositions for oral administration include powders or granules, suspensions or solutions in water or non-aqueous media, sachets, capsules or tablets. The oral composition can optionally contain inert pharmaceutical excipients such as thickeners, diluents, flavorings, dispersing aids, emulsifiers, binders, preservatives and the like.

The term "parenteral administration" indicates any route of administration other than via oral administration and includes, but is not limited to, administration by intravenous drip or bolus injection, intraperitoneal, intratechal, intralesional, subcutaneous, or intra muscular injection, topical, ocular, transdermal, rectal, vaginal, nasal administration or by inhalation.

Formulations for parenteral administration include but are not limited to sterile aqueous solutions which can also contain buffers, diluents and other suitable additives.

The compositions described herein are also suitable for administration in immediate release formulations, and/or in controlled or sustained release formulations. The sustained release systems can be tailored for administration according to any one of the proposed administration regimes. Slow or extended-release delivery systems, including any of a number of biopolymers (biological-based systems), systems employing liposomes, and polymeric delivery systems, can be utilized with the compositions described herein to provide a continuous or long-term source of therapeutic compound(s).

It is to be understood that the phraseology or terminology used herein is for the purpose of description and not of limitation, such that the terminology or phraseology of the present specification is to be interpreted by the skilled artisan in light of the teachings and guidance presented herein, in combination with the knowledge of one of ordinary skill in the art.

The pharmaceutical compositions can contain in addition to the active ingredient conventional pharmaceutically acceptable carriers, diluents and excipients necessary to produce a physiologically acceptable and stable formulation. The terms carrier, diluent or excipient mean an ingredient that is compatible with the other ingredients of the compositions disclosed herein, especially substances which do not react with the compounds of the invention and are not overly deleterious to the patient or animal to which the formulation is to be administered. For compounds having solubility problems, and some compounds of the present invention are characteristically hydrophobic and practically insoluble in water with high lipophilicity, as expressed by their high octanol/water partition coefficient and log P values, formulation strategies to prepare acceptable dosage forms will be applied. Enabling therapeutically effective and convenient administration of the compounds of the present invention is an integral part of this invention.

The pharmaceutical compositions can be in a liquid, aerosol or solid dosage form, and can be formulated into any suitable formulation including, but not limited to, solutions, suspensions, micelles, emulsions, microemulsions, aerosols, ointments, gels, suppositories, capsules, tablets, and the like, as will be required for the appropriate route of administration.

Solid compositions for oral administration such as tablets, pills, capsules, softgels or the like can be prepared by mixing the active ingredient with conventional, pharmaceutically acceptable ingredients such as corn starch, lactose, sucrose, mannitol, sorbitol, talc, polyvinylpyrrolidone, polyethyleneglycol, cyclodextrins, dextrans, glycerol, polyglycolized glycerides, tocopheryl polyethyleneglycol succinate, sodium lauryl sulfate, polyethoxylated castor oils, non-ionic surfactants, stearic acid, magnesium stearate, dicalcium phosphate and gums as pharmaceutically acceptable diluents. The tablets or pills can be coated or otherwise compounded with pharmaceutically acceptable materials known in the art, such as microcrystalline cellulose and cellulose derivatives such as hydroxypropylmethylcellulose (HPMC), to provide a dosage form affording prolonged action or sustained release. Coating formulations can be chosen to provide controlled or sustained release of the drug, as is known in the art.

Other solid compositions can be prepared as suppositories or retention enemas, for rectal administration using conventional suppository bases such as cocoa butter or other glycerides. Liquid forms can be prepared for oral administration or for injection, the term including but not limited to subcutaneous, transdermal, intravenous, intrathecal, intralesional, adjacent to or into tumors, and other parenteral routes of administration. The liquid compositions include aqueous solutions, with or without organic cosolvents, aqueous or oil suspensions including but not limited to cyclodextrins as suspending agent, flavored emulsions with edible oils, triglycerides and phospholipids, as well as elixirs and similar pharmaceutical vehicles. In addition, the compositions of the present invention can be formed as aerosols, for intranasal and like administration. For administration by inhalation, the compounds of the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch. Topical pharmaceutical compositions of the present invention can be formulated as solution, lotion, gel, cream, ointment, emulsion or adhesive film with pharmaceutically acceptable excipients including but not limited to propylene glycol, phospholipids, monoglycerides, diglycerides, triglycerides, polysorbates, surfactants, hydrogels, petrolatum or other such excipients as are known in the art.

Pharmaceutical compositions of the present invention can be manufactured by processes well known in the art, e.g., by means of conventional mixing, dissolving, wet granulating, dry-mixing, direct compression, grinding, pulverizing, dragee-making, levigating, emulsifying, encapsulating, entrapping or lyophilizing processes.

Prior to their use as medicaments, the pharmaceutical compositions can be formulated in unit dosage forms. The active dose for humans can be determined by standard clinical techniques and is generally in the range of from 0.01 mg to about 50 mg per kg body weight, in a regimen of 1-4 times a day. The preferred range of dosage varies with the specific compound used and is generally in the range of from 0.1 mg to about 20 mg per kg body weight. However, it is evident to one skilled in the art that dosages would be determined by the attending physician, according to the disease or disorder to be treated, its severity, the desired therapeutic effect, the duration of treatment, the method and frequency of administration, the patient's age, weight, gender and medical condition, concurrent treatment, if any, i.e., co-administration and combination with additional medications, contraindications, the route of administration, and the like. The administration of the compositions of the present invention to a subject in need thereof can be continuous, for example once, twice or thrice daily, or intermittent for example once weekly, twice weekly, once monthly and the like, and can be gradual or continuous, constant or at a controlled rate.

Effective doses can be extrapolated from dose-response curves derived from in vitro or animal model test systems. For example, an estimated effective mg/kg dose for humans can be obtained based on data generated from mice or rat studies, for an initial approximation the effective mg/kg dosage in mice or rats is divided by twelve or six, respectively.

Pharmaceutical compositions of the present invention can also include one or more additional active ingredients. The administration and dosage of such second agents is according to the schedule listed in the product information sheet of the approved agents, in the Physicians Desk Reference (PDR) as well as therapeutic protocols well known in the art.

When two or more active ingredients are administered to achieve the therapeutic goals of the present invention, co-administration can be in a unique dosage form for or in separate dosage forms for combined administration. Combined administration in the context of this invention is defined to mean the administration of more than one therapeutic in the course of a coordinated treatment to achieve an improved clinical outcome. Such combined administration can occur at the same time and also be coextensive, that is, occurring during overlapping periods of time. As used herein, co-administration is explicitly meant to include combined therapies that are administered individually or as a single composition. When administered individually, the separate therapeutic agents can be administered at substantially the same time or under separate regimens.

In addition, the present invention provides a method of treatment which comprises acutely or chronically administering to a subject in need thereof a pharmaceutical composition comprising a prophylactically and/or therapeutically effective amount of aforesaid compounds, either alone or in combination with one or more active ingredients.

According to a further aspect, the present invention provides a method of preventing, alleviating or treating indications as above described, which comprises administering to an individual in need thereof a prophylactically and/or therapeutically effective amount of pharmaceutical composition comprising as an active ingredient a compound of compounds a, b, c, d, e, f, g, h, i, j, k, l, m, n, o, p, q, r, s, t, u, v, w, x, y, z, aa, bb, cc, dd, ee, ff, gg, hh, ii, jj, kk, ll, mm, nn, oo, pp and qq as above defined, with the proviso defined therein.

The principles of the present invention will be more fully understood by reference to the following examples, which illustrate preferred embodiments of the invention and are to be construed in a non-limitative manner.

EXAMPLES

The following examples are provided in order to demonstrate and further illustrate certain preferred embodiments and aspects of the present invention and are not to be construed as limiting the scope thereof.

For convenience and better understanding, the section of the Examples is divided into two subsections: the Chemical Section describing the synthesis of compounds of the invention, some of their properties and their formulation; and the Biological Section describing the biological activity of the compounds.

In the experimental disclosure which follows, the following abbreviations apply: N (normal); M (molar); mM (millimolar); µM (micromolar); mmol (millimole); kg (kilograms); g (grams); mg (milligrams); µg (micrograms); ng (nanograms); pg (picograms); ml (milliliters); µl (microliters); mm (millimeters); µm (micrometers); h (hours); min (minutes); MHz (mega Hertz); IR (infra red); NMR (nuclear magnetic resonance); MS (mass spectroscopy); HPLC (high pressure liquid chromatography); TLC (thin layer chromatography); ACN (acetonitrile); $Cs_2CO_3$ (cesium carbonate); DCM (dichloromethane); DMF (dimethyl formamide); DMAP (dimethyl amino pyridine); EtOAc (ethyl acetate); $Et_2O$ (ethyl ether); EtOH (ethanol); IPA (isopropyl alcohol); PE (petroleum ether); TBAI (tetra-n-butylammonium iodide); tBuOK (potassium tert-butoxide); THF (tetrahydrofuran); p-TSA (para-toluene sulfonic acid); eq. (equivalent); sat. (saturated); ppm (part per million); ° C. (degrees Centigrade); RH (relative humidity); RT (room temperature); anh (anhydrous); O/N (overnight); hr (hour); min (minute); i.p. (intraperitoneally); i.v. (intravenously); p.o. (per os); s.c. (subcutaneously); AUC (Area Under the Curve); SD (standard deviation); SEM (standard error of the mean); NA (not available or not tested).

Chemical Section

In the synthetic examples, unless otherwise noted, the reaction was worked-up as follows. Upon completion of the reaction, as monitored by TLC (20% EA in PE), the mixture was washed twice with a solution of saturated sodium bicarbonate and then once with brine. The organic phase was separated, dried and evaporated, and the crude product was isolated and purified by column chromatography on silica gel with 20% ethyl acetate in petroleum ether as the eluent. All compounds were characterized by mass spectroscopy (MS) and resonances were assigned by 300 or 600 MHz nuclear magnetic resonance (NMR), as appropriate. MS and NMR spectra were consistent with the assigned structure.

Compounds of the invention were prepared according to the description and accompanying schemes described below. The following examples illustrate the synthesis of several exemplary compounds of the present invention. Though the examples disclose specific sulfonamide derivatives, it is clear that a diversity of derivatives could be used in the same or in alternative synthetic procedures known to persons skilled in the art of medicinal chemistry.

Example 1

Synthesis

Synthesis of Compound 1

4-(2,4-dichloro-phenylamino)-N-(2-morpholin-4-yl-ethyl)-2-trifluoromethyl-benzenesulfonamide a) To a solution of (1-morpholine)-2-ethylamine (320 mg. 2.46 mmol) in 15 ml THF solution of 4-bromo-2-trifluoromethylbenzenesulfonyl chloride (350 mg, 1.08 mmol) was added in one portion and reaction mixture was stirred for a day. Ethyl acetate was added and mixture was washed twice with 1 N HCl, water and brine. After drying over sodium sulfate solvent was evaporated and crude oil used in the next stage. Yield 9.4%.

b) Mixture of the product of step (a) (41.6 mg, 0.083 mmol), 2,4-dichloroaniline (26 mg, 0.16 mmol), CuBr (20 mg, 0.13 mmol) and potassium carbonate (25 mg, 0.18 mmol) in 5 ml DMF was relaxed for 6 hours. DMF was evaporated in vacuum and crude oil was purified by Combiflash (PE-THF). Yield 14%

Synthesis of Compound 2

N-Benzo[1,3]dioxol-5-ylmethyl-4-(2,4-dichloro-phenylamino)-2-trifluoromethyl-benzenesulfonamide a) To a solution of C-benzodioxol-5-ylmethylamine (158 mg. 1.04 mmol) and DIEA (146 mg, 1.13 mmol) in 15 ml THF 4-bromo-2-trifluoromethylbenzenesulfonyl chloride (321 mg, 0.99 mmol) was added in one portion and reaction mixture was stirred for a day. Ethyl acetate was added and mixture was washed twice with 1 N HCl, water and brine. After drying over sodium sulfate solvent was evaporated and crude solid used in the next stage. Yield 78%.

b) Mixture of the product of step (a) (342 mg, 0.78 mmol), 2,4-dichloroaniline (332 mg, 2.04 mmol), Pd(OAc)$_2$ (19 mg, 0.08 mmol), BINAP (69 mg, 0.11 mmol) and cesium carbonate (360 mg, 1.11 mmol) in 15 ml toluene was relaxed for 6 hours. Toluene was evaporated in vacuum and crude oil was purified by Combiflash (PE-THF). Yield 16%

$^1$H NMR: (CDCl$_3$) δ: 4.08 (2H, d, CH); 4.82 (1H, t, NH); 5.93 (2H, s, CH); 6.25 (1H, s, NH); 6.68-6.71 (3H, m, CH); 7.15 (1H, dd, CH); 7.30-7.39 (3H, m, CH); 7.51 (1H, d, CH); 8.06 (1H, d, CH). Molecular ion observed [M−H]$^−$=517.2 consistent with the molecular formula C$_{21}$H$_{15}$Cl$_2$F$_3$N$_2$O$_4$S.

Synthesis of Compound 3

N-Cyclopropylmethyl-4-(2,4-dichloro-phenylamino)-2-trifluoromethyl-benzenesulfonamide a) To a solution of cyclopropylamine (210 mg. 2.95 mmol) and in 15 ml THF 4-bromo-2-trifluoromethylbenzenesulfonyl chloride (321 mg, 0.99 mmol) was added in one portion and reaction mixture was stirred for a day. Ethyl acetate was added and mixture was washed twice with 1 N HCl, water and brine. After drying over sodium sulfate solvent was evaporated and crude solid used in the next stage. Yield 97%.

b) Mixture of the product of step (a) (356 mg, 0.97 mmol), 2,4-dichloroaniline (270 mg, 1.66 mmol), Pd(OAc)$_2$ (23 mg, 0.10 mmol), BINAP (69 mg, 0.11 mmol) and cesium carbonate (334 mg, 1.04 mmol) in 15 ml toluene was relaxed for 6 hours. Toluene was evaporated in vacuum and crude oil was purified by Combiflash (PE-THF). Yield 56%

$^1$H NMR: (CDCl$_3$) δ: 0.09-0.13 (2H, m, CH); 0.45-0.51 (2H, m, CH); 0.89 (1H, m, CH); 2.81-2.85 (2H, dd, CH); 4.68 (1H, s, NH); 6.19 (1H, s, NH); 7.16-7.19 (1H, dd, CH); 7.24-7.28 (3H, m, CH); 7.32-7.39 (2H, m, CH); 7.51 (1H, d, CH); 8.09 (1H, d, CH). Molecular ion observed [M−H]$^+$=439 consistent with the molecular formula C$_{17}$H$_{15}$Cl$_2$F$_3$N$_2$O$_2$S.

Synthesis of Compound 4

N-Cyclopropylmethyl-4-(3,5-dimethoxy-phenylamino)-2-trifluoromethyl-benzenesulfonamide Mixture of 4-bromo-N-cyclopropylmethyl-2-trifluoromethylbenzenesulfonamide (295 mg, 0.82 mmol), 3,5-dimethoxyaniline (142 mg, 0.92 mmol), Pd(OAc)$_2$ (26 mg, 0.11 mmol), BINAP (70 mg, 0.11 mmol) and cesium carbonate (395 mg, 1.21 mmol) in 15 ml toluene was relaxed for 6 hours. Toluene was evaporated in vacuum and crude oil was purified by Combiflash (PE-THF). Yield 48%

$^1$H NMR: (CDCl$_3$) δ: 0.07-0.12 (2H, m, CH); 0.44-0.50 (2H, m, CH); 0.85-0.92 (1H, m, CH); 2.80-2.82 (2H, dd, CH); 3.79 (6H, s, CH); 4.64(1H, s, NH); 6.26-6.33 (3H, m, CH); 7.15-7.18 (1H, dd, CH); 7.36 (1H, d, CH); 8.25 (1H, d, CH). Molecular ion observed [M−H]$^+$=431 consistent with the molecular formula C$_{19}$H$_{21}$F$_3$N$_2$O$_4$S.

Synthesis of Compound 6

N-cyclopropylmethyl-4-(4-methoxy-phenylamino)-2-trifluoromethyl-benzensulfonamide A mixture of 4-bromo-N-cyclopropylmethyl-2-trifluoromethylbenzenesulfonamide (295 mg, 0.82 mmol), 4-methoxyaniline (142 mg, 0.92 mmol), Pd(OAc)$_2$ (26 mg, 0.11 mmol), BINAP (70 mg, 0.11 mmol) and cesium carbonate (395 mg, 1.21 mmol) in 15 ml toluene was relaxed for 6 hours. Toluene was evaporated in vacuum and crude oil was purified by Combiflash (PE-THF). Yield 45%

$^1$H NMR: (CDCl$_3$) δ: 0.06-0.10 (2H, m, CH); 0.39-0.55 (2H, m, CH); 0.81-0.94 (1H, m, CH); 2.77-2.82 (2H, dd, CH); 3.83 (3H, s, CH); 4.61(1H, s, NH); 6.02 (1H, s, NH); 6.85-6.89 (3H, m, CH); 7.03-7.15 (3H, m, CH); 7.28-7.31 (1H, d, CH); 7.98 (1H, d, CH). Molecular ion observed [M−H]$^+$=401 consistent with the molecular formula C$_{18}$H$_{19}$F$_3$N$_2$O$_3$S.

Synthesis of Compound 7

N-Cyclopropylmethyl-4-phenylamino-2-trifluoromethyl-benzenesulfonamide

A mixture of 4-bromo-N-cyclopropylmethyl-2-trifluoromethylbenzenesulfonamide (183 mg, 0.51 mmol), aniline (93 mg, 1.0 mmol), Pd(OAc)$_2$ (11 mg, 0.05 mmol), BINAP (33 mg, 0.05 mmol) and cesium carbonate (246 mg, 0.75 mmol) in 15 ml toluene was relaxed for 6 hours. Toluene was evaporated in vacuum and crude oil was purified by Combiflash (PE-THF). Yield 20%

$^1$H NMR: (CDCl$_3$) δ: 0.07-0.14 (2H, m, CH); 0.46-0.52 (2H, m, CH); 0.85-0.92 (1H, m, CH); 2.80-2.82 (2H, dd, CH); 4.60(1H, s, NH); 6.3 (1H, s, NH); 7.11-7.21 (3H, m, CH); 7.33-7.43 (4H, m, CH); 8.15 (1H, d, CH). Molecular ion observed [M−H]$^+$=471 consistent with the molecular formula C$_{17}$H$_{17}$F$_3$N$_2$O$_2$S.

Synthesis of Compound 9

4-(2,4-Dichloro-phenylamino)-N-(tetrahydro-furan-2-ylmethyl)-2-trifluoromethyl-benzenesulfonamide a) To a solution of tetrahydrofurfurylamine (127 mg. 1.25 mmol) and in 15 ml THF 4-bromo-2-trifluoromethyl-benzenesulfonyl chloride (209 mg, 0.64 mmol) was added in one portion and reaction mixture was stirred for a day. Ethyl acetate was added and mixture was washed twice with 1 N HCl, water and brine. After drying over sodium sulfate solvent was evaporated and crude solid used in the next stage. Yield 66%.

b) Mixture of the product of step (a) (151 mg, 0.42 mmol), 2,4-dichloroaniline (98 mg, 0.97 mmol), Pd(OAc)$_2$ (14 mg, 0.06 mmol), BINAP (39 mg, 0.0062 mmol) and cesium carbonate (283 mg, 0.87 mmol) in 15 ml toluene was relaxed for 6 hours. Toluene was evaporated in vacuum and crude oil was purified by Combiflash (PE-THF). Yield 33%

$^1$H NMR: (CDCl$_3$) δ: 1.60-1.67 (1H, m, CH); 1.84-2.02 (3H, m, CH); 2.91-2.97 (1H, m, CH); 3.11-3.16 (1H, m, CH); 3.70-3.84(1H, m, CH); 3.95-3.98 (1H, m, CH); 4.97 (1H, s, NH); 6.32 (1H, s, NH); 7.17(1H, dd, CH); 7.26-7.30 (1H, dd, CH); 7.36 (1H, d, CH); 7.40 (1H, d, CH); 7.49 (1H, d, CH); 8.09 (1H, d, CH). Molecular ion observed [M−H]$^+$=469 consistent with the molecular formula C$_{18}$H$_{17}$Cl$_2$F$_3$N$_2$O$_3$S.

Synthesis of Compound 10

N-Butyl-4-(2,4-dichloro-phenylamino)-2-trifluoromethyl-benzenesulfonamide a) To a solution of butylamine (205 mg. 2.8 mmol) and in 15 ml THF 4-bromo-2-trifluoromethylbenzenesulfonyl chloride (373 mg, 1.14 mmol) was added in one portion and reaction mixture was stirred for a day. Ethyl acetate was added and mixture was washed twice with 1 N HCl, water and brine. After drying over sodium sulfate solvent was evaporated and crude solid used in the next stage. Yield 83%.

b) Mixture of the product of step (a) (300 mg, 0.83 mmol), 2,4-dichloroaniline (152 mg, 0.93 mmol), Pd(OAc)$_2$ (24 mg, 0.1 mmol), BINAP (63 mg, 0.1 mmol) and cesium carbonate (223 mg, 0.99 mmol) in 15 ml toluene was relaxed for 6 hours. Toluene was evaporated in vacuum and crude oil was purified by Combiflash (PE-THF). Yield 19%

$^1$H NMR: (CDCl$_3$) δ: 088 (3H, t, CH); 1.30-1.35 (2H, m, CH); 1.45-1.50 (2H, m, CH); 2.95-2.97 (2H, q, CH); 4.52 (1H, t, NH); 6.33 (1H, s, NH); 7.18-7.22(1H, dd, CH); 7.26-7.30 (1H, dd, CH); 7.36 (1H, d, CH); 7.41 (1H, d, CH); 7.50 (1H, d, CH); 8.11 (1H, d, CH). Molecular ion observed [M−H]$^+$=441 consistent with the molecular formula C$_{18}$H$_{17}$Cl$_2$F$_3$N$_2$O$_3$S.

Synthesis of Compound 11

N-Cyclopropylmethyl-4-(3,5-dimethoxy-phenylamino)-2-trifluoromethoxy-benzenesulfonamide a) 4-Bromo-2-trifluoromethoxy-benzenesulfonyl chloride (339 mg, 1.0 mmol) was added in one portion to a stirred solution of cyclopropylmethylamine (180 mg, 2.5 mmol) in dry THF (15 mL), under N$_2$ atmosphere. After 24 h at rt, water and EtOAc were added, and the layers were separated. The organic layer was washed with 1 N HCl and saturated NaCl solutions, dried over Na$_2$SO$_4$, filtered and evaporated. The clean product was obtained as a yellow oil (260 mg, 90% Yield), transferred to the next step without further purification.

b) The product of step (a) (260 mg, 0.9 mmol) was dissolved in dry toluene (25 mL) under N$_2$ atmosphere. To the stirring solution were added Pd(OAc)$_2$ (26 mg, 0.12 mmol), BINAP (81 mg, 0.13 mmol) and cesium carbonate (480 mg, 1.48 mmol) and the reaction mixture was stirred at rt for 20 min. Dimethoxyaniline (208 mg, 1.36 mmol) was added and the mixture was stirred at rt for 10 min. Stirring was continued at 110° C. under N$_2$ atmosphere for 6 hours, cooled and allowed to proceed overnight at rt. The mixture was filtered through a small pad of silica gel on a sinter glass, eluted with additional amount of 30 mL toluene and then 50 mL petrol ether:EtOAc 1:1. 246 mg of yellowish crude oil obtained which was further purified using Combiflash (PE-THF) affording the clean desired product as a yellow oil (180 mg, 56% yield).

$^1$H NMR: (CDCl$_3$) δ 7.81 (d, 1H, CH); 6.99 (quint, 1H, CH); 6.87 (dd, 1H, CH); 6.32 (d, 2H, CH); 6.25 (t, 1H, CH); 4.63 (bt, 1H, NH); 3.78 (s, 6H, OCH$_3$); 2.82 (dd, 2H, CH$_2$N); 0.90 (m, 1H, CH); 0.48 (q, 2H, CH$_2$); 0.11 (q, 2H, CH$_2$).

MS: m/z 447.10 (MH$^+$).

Synthesis of Compound 12

N-Cyclopropylmethyl-4-(3,5-dimethoxy-phenylamino)-benzenesulfonamide a) 4-bromo benzenesulfonyl chloride (256 mg, 1.0 mmol) was added in one portion to a stirred solution of cyclopropylmethylamine (180 mg, 2.5 mmol) in dry THF (15 mL), under N$_2$ atmosphere. After 24 h at rt, water and EtOAc were added, and the layers were separated. The organic layer was washed with 1 N HCl and saturated NaCl solutions, dried over Na$_2$SO$_4$, filtered and evaporated. The clean product was obtained as a yellow oil (260 mg, 90% Yield), transferred to the next step without further purification.

b) The product of step (a) (260 mg, 0.9 mmol) was dissolved in dry toluene (20 mL) under N$_2$ atmosphere. To the stirring solution were added Pd(OAc)$_2$ (20 mg, 0.09 mmol), BINAP (62 mg, 0.1 mmol) and cesium carbonate (366 mg, 1.13 mmol) and the reaction mixture was stirred at rt for 20 min. Dimethoxyaniline (158 mg, 1.04 mmol) was added and the mixture was stirred at rt for 10 min. Stirring was continued at 110° C. under N$_2$ atmosphere for 6 hours, cooled and allowed to proceed overnight at rt. The mixture was filtered through a small pad of silica gel on a sinter glass, eluted with additional amount of 30 mL toluene and then 50 mL petrol ether: EtOAc 1:1. 246 mg of yellowish crude oil obtained which was further purified using Combiflash (PE-THF) affording the clean desired product as a yellow oil (180 mg, 56% yield).

$^1$H NMR: δ 7.70 (d, 2H, CH); 7.06 (d, 2H, CH); 6.32 (s, 2H, CH); 6.21 (s, 1H, CH); 3.78 (s, 6H, OCH$_3$); 2.82 (d, 2H, CH$_2$N); 0.90 (m, 1H, CH); 0.48 (q, 2H, CH$_2$); 0.11 (q, 2H, CH$_2$).

MS: m/z 363.00 (MH$^+$).

Synthesis of Compound 15

4-(2,4-Difluoro-phenylamino)-N-(tetrahydro-furan-2-ylmethyl)-2-trifluoromethyl-benzenesulfonamide a) 4-Bromo-2-trifluoromethyl-benzenesulfonyl chloride (250 mg, 0.77 mmol) was added in one portion to a stirred solution of tetrahydrofurylmethylamine (195 mg, 1.93 mmol) in dry THF (20 mL), under N$_2$ atmosphere. After 24 h at rt, water and EtOAc were added, and the layers were separated. The organic layer was washed with 1 N HCl and saturated NaCl solutions, dried over sodium sulfate, filtered and evaporated. The clean product was obtained as a yellow oil (301 mg, 100% Yield), transferred to the next step without further purification.

b) The product of step (a) (150 mg, 0.39 mmol) was dissolved in dry toluene (10 mL) under N$_2$ atmosphere. To the stirring solution were added Pd(OAc)$_2$ (8.7 mg, 0.039 mmol), BINAP (26.5 mg, 0.043 mmol) and cesium carbonate (157 mg, 0.48 mmol) and the reaction mixture was stirred at rt for 20 min. 2,4-Difluoro-phenylamine (57 mg, 0.44 mmol) was added and the mixture was stirred at rt for 10 min. Stirring was continued at 110° C. under N$_2$ atmosphere for 6 hours, cooled and allowed to proceed overnight at rt. The mixture was filtered through a small pad of silica gel on a sinter glass, eluted with additional amount of 30 mL toluene and then 50 mL petrol ether:EtOAc 1:1. 250 mg of yellowish crude oil obtained which was further purified using Combiflash (PE-THF) affording the clean desired product as a yellow oil (135 mg, 79% yield).

$^1$H NMR: (CDCl$_3$) δ 8.01 (d, 1H, CH); 7.33 (m, 1H, CH); 7.24 (d, 1H, CH); 6.96 (m, 3H, CH); 6.02 (bs, 1H, NH); 4.93 (t, 1H, NH); 3.95 (m, 1H, OCH); 3.75 (m, 2H, OCH$_2$); 3.12 (ddd, 1H, CH$_2$N); 2.90 (dt, 1H, CH$_2$N); 1.91 (m, 2H, CH$_2$); 1.62 (m, 2H, CH$_2$).

MS: m/z 437 (MH$^+$).

Synthesis of Compound 16

N-Cyclopropylmethyl-4-(4,6-dimethoxy-pyrimidin-2-ylamino)-2-trifluoromethyl-benzenesulfonamide Mixture of 4-bromo-N-cyclopropylmethyl-2-trifluoromethylbenzenesulfonamide (228 mg, 0.63 mmol), 2,-amino-4,6-dimethoxypyrimidine (156 mg, 1.0 mmol), Pd(OAc)$_2$ (26 mg, 0.11 mmol), BINAP (78 mg, 0.12 mmol) and cesium carbonate (362 mg, 1.11 mmol) in 15 ml toluene was relaxed for 6 hours. Toluene was evaporated in vacuum and crude oil was purified by Combiflash (PE-THF). Yield 41%

$^1$H NMR: (CDCl$_3$) δ: 0.08-0.13 (2H, m, CH); 0.43-0.51 (2H, m, CH); 0.82-0.95 (1H, m, CH); 2.83-2.88 (2H, dd, CH); 4.73(1H, t, NH); 5.73(1H, s, CH); 7.68-7.72 (1H, dd, CH); 7.72 (1H, s, NH); 8.16 (1H, d, CH); 8.63 (1H, d, CH). Molecular ion observed [M–H]$^+$=433 consistent with the molecular formula C$_{19}$H$_{21}$F$_3$N$_2$O$_4$S.

Synthesis of Compound 17

4-(3,5-Dimethoxy-phenylamino)-2-fluoro-N-(tetrahydro-furan-2-ylmethyl)-benzenesulfonamide a) 4-Bromo-2-fluoro-benzenesulfonyl chloride (250 mg, 0.91 mmol) was added in one portion to a stirred solution of tetrahydrofurylmethylamine (231 mg, 2.29 mmol) in dry THF (15 mL), under N$_2$ atmosphere. After 24 h at rt, water and EtOAc were added, and the layers were separated. The organic layer was washed with 1 N HCl and saturated NaCl solutions, dried over Na$_2$SO$_4$, filtered and evaporated. The clean product was obtained as a yellow oil (310 mg, 100% Yield), transferred to the next step without further purification.

b) The product of step (a) (310 mg, 0.91 mmol) was dissolved in dry toluene (20 mL) under N$_2$ atmosphere. To the stirring solution were added Pd(OAc)$_2$ (21 mg, 0.092 mmol), BINAP (63 mg, 0.10 mmol) and cesium carbonate (374 mg, 1.15 mmol) and the reaction mixture was stirred at rt for 20 min. Dimethoxyaniline (163 mg, 1.06 mmol) was added and the mixture was stirred at rt for 10 min. Stirring was continued at 110° C. under N$_2$ atmosphere for 6 hours, cooled and allowed to proceed overnight at rt. The mixture was filtered through a small pad of silica gel on a sinter glass, eluted with additional amount of 30 mL toluene and then 50 mL petrol ether: EtOAc 1:1. 246 mg of yellowish crude oil obtained which was further purified using Combiflash (PE-THF) affording the clean desired product as a yellow oil (180 mg, 48% yield).

$^1$H NMR: (CDCl$_3$) δ 7.69 (t, 1H, CH); 6.80 (dd, 1H, CH); 6.75 (dd, 1H, CH); 6.34 (d, 2H, CH); 6.27 (t, 1H, CH); 4.96 (t, 1H, NH); 3.99 (m, 1H, OCH); 3.88-3.72 (m, 2H, OCH$_2$); 3.81 (s, 6H, OCH$_3$); 3.17 (ddd, 1H, CH$_2$N); 2.96 (dt, 1H, CH$_2$N); 1.92 (m, 2H, CH$_2$); 1.66 (m, 2H, CH$_2$).

MS: m/z 411.10 (MH$^+$).

Synthesis of Compound 18

4-(3,5-Dimethoxy-phenylamino)-3-fluoro-N-(tetrahydro-furan-2-ylmethyl)-benzenesulfonamide a) 4-Bromo-3-fluoro-benzenesulfonyl chloride (250 mg, 0.91 mmol) was added in one portion to a stirred solution of tetrahydrofurylmethylamine (231 mg, 2.29 mmol) in dry THF (20 mL), under N$_2$ atmosphere. After 24 h at rt, water and EtOAc were added, and the layers were separated. The organic layer was washed with 1 N HCl and saturated NaCl solutions, dried over sodium sulfate, filtered and evaporated. The clean product was obtained as a yellow oil (304 mg, 99% Yield), transferred to the next step without further purification.

b) The product of step (a) (304 mg, 0.9 mmol) was dissolved in dry toluene (20 mL) under N$_2$ atmosphere. To the stirring solution were added Pd(OAc)$_2$ (20 mg, 0.09 mmol), BINAP (62 mg, 0.10 mmol) and cesium carbonate (366 mg, 1.13 mmol) and the reaction mixture was stirred at rt for 20 min. Dimethoxyaniline (158 mg, 1.03 mmol) was added and the mixture was stirred at rt for 10 min. Stirring was continued at 110° C. under N$_2$ atmosphere for 6 hours, cooled and allowed to proceed overnight at rt. The mixture was filtered through a small pad of silica gel on a sinter glass, eluted with additional amount of 30 mL toluene and then 50 mL petrol ether: EtOAc 1:1. 300 mg of yellowish crude oil obtained which was further purified using Combiflash (PE-THF) affording the clean desired product as a yellow oil (225 mg, 61% yield).

Synthesis of Compound 19

4-(3,5-Dimethoxy-phenylamino)-2,5-difluoro-N-(tetrahydro-furan-2-ylmethyl)-benzenesulfonamide a) 4-Bromo-2,5-difluoro-benzenesulfonyl chloride (250 mg, 0.86 mmol) was added in one portion to a stirred solution of tetrahydrofurylmethylamine (217 mg, 2.14 mmol) in dry THF (20 mL), under N$_2$ atmosphere. After 24 h at rt, water and EtOAc were added, and the layers were separated. The organic layer was washed with 1 N HCl and saturated NaCl solutions, dried over sodium sulfate, filtered and evaporated. The clean product was obtained as a yellow oil (309 mg, 100% Yield), transferred to the next step without further purification.

b) The product of step (a) (309 mg, 0.86 mmol) was dissolved in dry toluene (20 mL) under N$_2$ atmosphere. To the stirring solution were added Pd(OAc)$_2$ (20 mg, 0.09 mmol), BINAP (60 mg, 0.096 mmol) and cesium carbonate (353 mg, 1.09 mmol) and the reaction mixture was stirred at rt for 20 min. Dimethoxyaniline (154 mg, 1.01 mmol) was added and the mixture was stirred at rt for 10 min. Stirring was continued at 110° C. under N$_2$ atmosphere for 6 hours, cooled and allowed to proceed overnight at rt. The mixture was filtered through a small pad of silica gel on a sinter glass, eluted with additional amount of 30 mL toluene and then 50 mL petrol ether: EtOAc 1:1. 326 mg of yellowish crude oil obtained which was further purified using Combiflash (PE-THF) affording the clean desired product as a yellow oil (188 mg, 51% yield).

$^1$H NMR: δ 9.48 (s, 1H, H$_1$); 7.34-7.25 (m, 5H, Ph); 5.70 (bd, 1H, NH); 5.09 (s, 2H, H$_5$); 4.23 (quint, J=7.2 Hz, 1H, H$_2$); 1.29 (d, J=7.5 Hz, 3H, H$_3$).

$^{13}$C NMR: δ 199.51 (C$_1$); 155.96 (C$_4$); 136.14, 128.49, 128.18, 128.06, (Ph); 66.95 (C$_5$); 55.78 (C$_2$); 14.53 (C$_3$).

MS: m/z 208 (MH$^+$, 12); 178 (M$^+$–CHO, 18); 91 (C$_7$H$_7^+$, 100).

HRMS: (DCI/CH$_4$) m/z for C$_{11}$H$_{14}$NO$_3$ (MH$^+$): calcd. 208.0974, found 208.0989; for C$_{10}$H$_{12}$NO$_2$ (M$^+$–CHO): calcd. 178.0868, found 178.0803.

Synthesis of Compound 20

4-(3,5-Dimethoxy-phenylamino)-N-(3-methoxypropyl)-2-trifluoromethyl-benzenesulfonamide a) 4-Bromo-2-trifluoromethylbenzenesulfonyl chloride (200 mg) was added in one portion to a stirred solution of 3-Methoxy-propylamine (166 mg) in THF (15 ml) under nitrogen at rt. The reaction mixture was stirred over night at the described conditions. Ethyl acetate (50 ml) was added and mixture was washed once with 1 N HCl, water and brine. After drying over sodium sulfate solvent was removed under reduced pressure and the resulting crude (210 mg) was used in the next stage without further purification.

b) A mixture of the product of step (a) (210 mg), 3-Methoxy-propylamine (175 mg), Pd(OAc)$_2$ (13 mg), BINAP (35 mg) and cesium carbonate (218 mg) in 15 ml toluene was relaxed for 12 hours. The reaction mixture was eluted through a silica bed with Toluene and then with PE:EtOAc (1:1). The toluene fraction was discarded and the solvent of the PE:EtOAc fraction was removed under reduced pressure. The crude product was purified by Combiflash (PE-THF). Yield 120 mg, 48%

Synthesis of Compound 21

4-(3,5-Dimethoxy-phenylamino)-N-(tetrahydro-furan-2-ylmethyl)-2-trifluoromethyl-benzenesulfonamide Mixture of 4-bromo-N-(tetrahydrofuran-2-ylmethyl)-2-trifluoromethyl benzenesulfonamide (171 mg, 0.44 mmol), 2,4-dimethoxyaniline (47 mg, 0.96 mmol), Pd(OAc)$_2$ (24 mg, 0.10 mmol), BINAP (78 mg, 0.10 mmol) and cesium carbonate (327 mg, 1.01 mmol) in 15 ml toluene was relaxed for 6 hours. Toluene was evaporated in vacuum and crude oil was purified twice by Combiflash (PE-THF). Yield 33%

$^1$H NMR: (CDCl$_3$) δ: 1.60-1.67 (1H, m, CH); 1.84-2.02 (3H, m, CH); 2.91-2.97 (1H, m, CH); 3.11-3.16 (1H, m, CH); 3.70-3.84(1H, m, CH); 3.95-3.98 (1H, m, CH); 4.97 (1H, s, NH); 6.32 (1H, s, NH); 7.17(1H, dd, CH); 7.26-7.30 (1H, dd, CH); 7.36 (1H, d, CH); 7.40 (1H, d, CH); 7.49 (1H, d, CH); 8.09 (1H, d, CH). Molecular ion observed [M–H]$^+$=469 consistent with the molecular formula C$_{18}$H$_{17}$Cl$_2$F$_3$N$_2$O$_3$S.

Synthesis of Compound 22

4-(3,5-Dimethoxy-phenylamino)-N-pyridin-4-ylmethyl-2-trifluoromethyl-benzenesulfonamide a) 4-Bromo-2-trifluoromethylbenzenesulfonyl chloride (200 mg) was added in one portion to a stirred solution of C-Pyridin-4-yl-methylamine (200 mg) in THF (15 ml) under nitrogen at rt. The reaction mixture was stirred over night at the described conditions. Ethyl acetate (50 ml) was added and mixture was washed once with 1 N HCl, water and brine. The combined water phases were neutralized with NaHCO$_3$ and extracted with EtOAc. This organic phase was washed with brine. After drying over sodium sulfate the solvent was removed under reduced pressure and the resulting crude (170 mg) was used in the next stage without further purification.

b) A mixture of the product of step (a) (170 mg), Pd(OAc)$_2$ (10 mg), BINAP (27 mg) and cesium carbonate (170 mg) in 15 ml toluene was relaxed for 12 hours. The reaction mixture was eluted through a silica bed with Toluene and then with PE: EtOAc (1:1) and then with EtOAc. The toluene fraction was discarded and the solvent of the PE:EtOAc fraction was removed under reduced pressure. The crude product was purified by Combiflash (PE-THF). Yield 85 mg, 42%

$^1$H NMR (300 MHz, CDCl$_3$, rt) δ 3.77 (s, 6H, ArOCH$_3$), 4.19 (d, 2H, J=6.3 Hz, CH$_2$), 5.47 (t broad, 1H, NH), 6.26 (t, 1H, J=2.1 Hz, ArH), 6.32 (d, 1H, J=2.1 Hz, ArH), 6.65 (s broad, 1H, NH), 7.08 (dd, 1H, J=2.4 Hz, J=9 Hz, ArH), 7.27 (d, 2H, J=4.8 Hz, Py), 7.29 (d broad, 1H, ArH), 7.92 (d, 1H, J=9 Hz, ArH), and 8.48 (d, 2H, J=4.8 Hz, Py).

MS: m/z 468.2 (MH$^+$)

Synthesis of Compound 23

(3,5-Dimethoxy-phenyl)-[4-(morpholine-4-sulfonyl)-3-trifluoromethyl-phenyl]-amine a) 4-Bromo-2-trifluoromethylbenzenesulfonyl chloride (200 mg) was added in one portion to a stirred solution of morpholine (160 mg) in THF (15 ml) under nitrogen at rt. The reaction mixture was stirred over night at the described conditions. Ethyl acetate (50 ml) was added and mixture was washed once with 1 N HCl, water and brine. After drying over sodium sulfate the solvent was removed under reduced pressure and the resulting crude (160 mg) was used in the next stage without further purification.

b) A mixture of the product of step (a) (160 mg), Pd(OAc)$_2$ (10 mg), BINAP (27 mg) and cesium carbonate (170 mg) in 15 ml toluene was relaxed for 12 hours. The reaction mixture was eluted through a silica bed with Toluene and then with PE: EtOAc (1:1) and then with EtOAc. The toluene fraction was discarded and the solvent of the PE:EtOAc fraction was removed under reduced pressure. The crude product was purified by Combiflash (PE-THF). Yield 190 mg, 99%

$^1$H NMR (300 MHz, CDCl$_3$, rt) δ 3.18 (dd, 4H, J=4.8 Hz, J=4.9 Hz CH$_2$), 3.73 (dd, 4H, J=4.8 Hz, J=4.9 Hz CH$_2$), 3.79 (s, 6H, ArOCH$_3$), 6.23 (s broad, 1H, NH), 6.28 (t, 1H, J=2.1 Hz, ArH), 6.335 (d, 2H, J=2.1 Hz, ArH), 7.19 (dd, 1H, J=2.4 Hz, J=9 Hz, ArH), 7.38 (d, 1H, J=2.4 Hz, ArH), and 7.92 (d, 1H, J=9 Hz, ArH).

MS: m/z 447.1 (MH$^+$)

Synthesis of Compound 24

4-(3,5-Dimethoxy-phenylamino)-N-(2-morpholin-4-yl-ethyl)-2-trifluoromethyl-benzenesulfonamide a) 4-Bromo-2-trifluoromethylbenzenesulfonyl chloride (200 mg) was added in one portion to a stirred solution of 2-Morpholin-4-yl-ethylamine (242 mg) in THF (15 ml) under nitrogen at rt. The reaction mixture was stirred over night at the described conditions. Ethyl acetate (50 ml) was added and mixture was washed with water and brine. After drying over sodium sulfate the solvent was removed under reduced pressure and the resulting crude (225 mg) was used in the next stage without further purification.

b) A mixture of the product of step (a) (225 mg), Pd(OAc)$_2$ (12 mg), BINAP (34 mg) and cesium carbonate (166 mg) in 15 ml toluene was relaxed for 12 hours. The reaction mixture was eluted through a silica bed with Toluene and then with PE: EtOAc (1:1) and then with EtOAc. The toluene fraction was discarded and the solvent of the PE:EtOAc fraction was removed under reduced pressure. The crude product was purified by Combiflash (PE-THF). Yield 170 mg, 65%

$^1$H NMR (300 MHz, CDCl$_3$, rt) δ 2.55 (s broad, 4H, CH$_2$), 2.65 (s broad, 2H, CH$_2$), 3.15 (s broad, 2H, CH$_2$), 3.75 (m, 4H, CH$_2$), 3.79 (s, 6H, ArOCH$_3$), 5.72 (s broad, 1H, NH), 6.267 (t, 1H, J=2.1 Hz, ArH), 6.33 (d, 2H, J=2.1 Hz, ArH), 6.368 (s, 1H, NH), 7.19 (dd, 1H, J=2.4 Hz, J=8.8 Hz, ArH), 7.375 (d, 1H, J=2.4 Hz, ArH), and 8.00 (d, 1H, J=8.7 Hz, ArH).

MS: m/z 490.1 (MH$^+$)

Synthesis of Compound 25

4-Cyclohexylamino-N-(tetrahydro-furan-2-ylmethyl)-2-trifluoromethyl-benzenesulfonamide Mixture of 4-bromo-N-(tetrahydrofuran-2-ylmethyl)-2-trifluoromethylbenzenesulfonamide (200 mg, 0.51 mmol), cyclohexylamine (193 mg, 1.94 mmol), Pd(OAc)$_2$ (22 mg, 0.10 mmol), BINAP (70 mg, 0.11 mmol) and cesium carbonate (340 mg, 1.01 mmol) in 15 ml toluene was relaxed for 6 hours. Toluene was evaporated in vacuum and crude oil was purified twice by Combiflash (PE-THF). Yield 29%

$^1$H NMR: (CDCl$_3$) δ: 1.23-1.39 (4H, m, CH); 1.63-2.07 (10H, m, CH); 2.87-2.93 (1H, m, CH); 3.06-3.11 (1H, m, CH); 3.30-3.42(1H, m, CH); 3.69-3.83 (2H, m, CH); 3.93-3.97(1H, m, CH); 4.68 (1H, s, NH); 6.70 (1H, d, CH); 6.97-6.99(1H, d, CH); 7.93-7.96 (1H, d, CH). Molecular ion observed [M–H]$^+$=407 consistent with the molecular formula $C_{18}H_{25}F_3N_2O_3S$.

Synthesis of Compound 26

4-(Bicyclo[2.2.1]hept-2-ylamino)-N-(tetrahydro-furan-2-ylmethyl)-2-trifluoromethyl-benzenesulfonamide Mixture of 4-bromo-N-(tetrahydrofuran-2-ylmethyl)-2-trifluoromethylbenzenesulfonamide (194 mg, 0.50 mmol), aminonorbornane (109 mg, 0.98 mmol), Pd(OAc)$_2$ (28 mg, 0.10 mmol), BINAP (63 mg, 0.10 mmol) and cesium carbonate (310 mg, 1.3 mmol) in 15 ml toluene was relaxed for 6 hours. Toluene was evaporated in vacuum and crude oil was purified twice by Combiflash (PE-THF). Yield 59%

$^1$H NMR: (CDCl$_3$) δ: 1.18-1.27 (4H, m, CH); 1.43-1.61 (4H, m, CH); 1.83-2.10(4H, m, CH); 2.27-2.28 (1H, d, CH); 2.35-2.36 (1H, s, CH);2.85-2.91(1H, m, CH); 3.03-3.1(1H, m, CH); 3.27-3.30 (1H, m, CH); 3.68-3.82(2H, m, CH); 3.92-3.95(1H, m, CH); 4.85 (1H, s, NH); 6.65-6.68 (1H, d, CH); 6.95 (1H, s, CH); 7.92-7.95 (1H, d, CH). Molecular ion observed [M–H]$^+$=419 consistent with the molecular formula $C_{19}H_{25}F_3N_2O_3S$.

Synthesis of Compound 27

2-Chloro-4-(3,5-dimethoxy-phenylamino)-N-(tetrahydro-furan-2-ylmethyl)-benzenesulfonamide a) 4-Bromo-2-chloro-benzenesulfonyl chloride (250 mg, 0.86 mmol) was added in one portion to a stirred solution of tetrahydrofurylmethylamine (218 mg, 2.16 mmol) in dry THF (20 mL), under N$_2$ atmosphere. After 24 h at rt, water and EtOAc were added, and the layers were separated. The organic layer was washed with 1 N HCl and saturated NaCl solutions, dried over sodium sulfate, filtered and evaporated. The clean product was obtained as a yellow oil (305 mg, 100% Yield), transferred to the next step without further purification.

b) The product of step (a) (120 mg, 0.34 mmol) was dissolved in dry toluene (10 mL) under N$_2$ atmosphere. To the stirring solution were added Pd(OAc)$_2$ (7.6 mg, 0.034 mmol), BINAP (23 mg, 0.037 mmol) and cesium carbonate (138 mg, 0.43 mmol) and the reaction mixture was stirred at rt for 20 min. Dimethoxyaniline (60 mg, 0.39 mmol) was added and the mixture was stirred at rt for 10 min. Stirring was continued at 110° C. under N$_2$ atmosphere for 6 hours, cooled and allowed to proceed overnight at rt. The mixture was filtered through a small pad of silica gel on a sinter glass, eluted with additional amount of 30 mL toluene and then 50 mL petrol ether: EtOAc 1:1. 131 mg of yellowish crude oil obtained which was further purified using Combiflash (PE-THF) affording the clean desired product as a yellow oil (93 mg, 64% yield).

$^1$H NMR: (CDCl$_3$) δ 7.89 (d, 1H, CH); 7.09 (d, 1H, CH); 6.91 (dd, 1H, CH); 6.33 (d, 2H, CH); 6.26 (t, 1H, CH); 5.23 (t, 1H, NH); 3.98 (m, 1H, OCH); 3.88-3.70 (m, 2H, OCH$_2$); 3.81 (s, 6H, OCH$_3$); 3.08 (ddd, 1H, CH$_2$N); 2.87 (dt, 1H, CH$_2$N); 1.92 (m, 2H, CH$_2$); 1.65 (m, 2H, CH$_2$).

MS: m/z 427.20 (MH$^+$).

Synthesis of Compound 28

2,6-Dichloro-4-(3,5-dimethoxy-phenylamino)-N-(tetrahydro-furan-2-ylmethyl)-benzenesulfonamide a) 4-Bromo-2,6-dichloro-benzenesulfonyl chloride (250 mg, 0.77 mmol) was added in one portion to a stirred solution of tetrahydrofurylmethylamine (195 mg, 1.93 mmol) in dry THF (20 mL), under N$_2$ atmosphere. After 24 h at rt, water and EtOAc were added, and the layers were separated. The organic layer was washed with 1 N HCl and saturated NaCl solutions, dried over sodium sulfate, filtered and evaporated. The clean product was obtained as a yellow oil (292 mg, 98% Yield), transferred to the next step without further purification.

b) The product of step (a) (142 mg, 0.37 mmol) was dissolved in dry toluene (10 mL) under N$_2$ atmosphere. To the stirring solution were added Pd(OAc)$_2$ (8.2 mg, 0.037 mmol), BINAP (25 mg, 0.04 mmol) and cesium carbonate (148 mg, 0.46 mmol) and the reaction mixture was stirred at rt for 20 min. Dimethoxyaniline (64 mg, 0.42 mmol) was added and the mixture was stirred at rt for 10 min. Stirring was continued at 110° C. under N$_2$ atmosphere for 6 hours, cooled and allowed to proceed overnight at rt. The mixture was filtered through a small pad of silica gel on a sinter glass, eluted with additional amount of 30 mL toluene and then 50 mL petrol ether: EtOAc 1:1. 153 mg of yellowish crude oil obtained which was further purified using Combiflash (PE-THF) affording the clean desired product as a yellow oil (85 mg, 50% yield).

$^1$H NMR: (CDCl$_3$) δ 7.01 (s, 2H, CH); 6.32 (d, 2H, CH); 6.30 (t, 1H, CH); 6.08 (bs, 1H, NH); 5.55 (t, 1H, NH); 4.01 (m, 1H, OCH); 3.94-3.70 (m, 2H, OCH$_2$); 3.81 (s, 6H, OCH$_3$); 3.20 (ddd, 1H, CH$_2$N); 2.97 (dt, 1H, CH$_2$N); 1.94 (m, 2H, CH$_2$); 1.69 (m, 2H, CH$_2$).

MS: m/z 461.10 (MH$^+$).

Synthesis of Compound 29

4-(3,5-Dimethoxy-phenylamino)-N-furan-2-ylmethyl-2-trifluoromethyl-benzenesulfonamide a) 4-Bromo-2-trifluoromethylbenzenesulfonyl chloride (200 mg) was added in one portion to a stirred solution of C-Furan-2-yl-methylamine (181 mg) in THF (15 ml) under nitrogen at rt. The reaction mixture was stirred over night at the described conditions. Ethyl acetate (50 ml) was added and mixture was washed with water and brine. After drying over sodium sulfate the solvent was removed under reduced pressure and the resulting crude (197 mg) was used in the next stage without further purification.

b) A mixture of the product of step (a) (197 mg), Pd(OAc)$_2$ (12 mg), BINAP (32 mg) and cesium carbonate (199 mg) in 15 ml toluene was relaxed for 12 hours. The reaction mixture was eluted through a silica bed with Toluene and then with PE:EtOAc (1:1) and then with EtOAc. The toluene fraction was discarded and the solvent of the PE:EtOAc fraction was removed under reduced pressure. The crude product was purified by Combiflash (PE-THF). Yield 28 mg, 12%

$^1$H NMR (300 MHz, CDCl$_3$, rt) 3.79 (s, 6H, ArOCH$_3$), 4.19 (d, 2H, J=6 Hz, CH$_2$), 4.85 (t, broad, 1H, NH), 6.068 (dd, 1H, J=0.9 Hz, J=3.3 Hz, CH), 6.207 (dd, 1H, J=1.5 Hz, J=3.3 Hz, CH), 6.68 (t, 1H, J=2.1 Hz, ArH), 6.32 (d, 2H, J=2.1 Hz, ArH), 6.98 (s, 1H, NH), 7.13 (dd, 1H, J=2.4 Hz, J=9 Hz, ArH), 7.227 (dd, 1H, J=0.9 Hz, J=1.8 Hz, CH), 7.318 (d, 1H, J=2.4 Hz, ArH), and 7.985 (d, 1H, J=9 Hz, ArH).

MS: m/z 457.2 (MH$^+$)

Synthesis of Compound 30

4-(3,5-Dimethoxy-phenylamino)-N-isoquinolin-5-yl-2-trifluoromethyl-benzenesulfonamide a) 4-Bromo-2-trifluoromethylbenzenesulfonyl chloride (200 mg) was added in one portion to a stirred solution of Isoquinolin-5-ylamine (186 mg) in THF (15 ml) under nitrogen at rt. The reaction mixture was stirred over night at the described conditions. Ethyl acetate (50 ml) was added and mixture was washed with water and brine. After drying over sodium sulfate the solvent was removed under reduced pressure and the resulting crude (210 mg) was used in the next stage without further purification.

b) A mixture of the product of step (a) (210 mg), Pd(OAc)$_2$ (11 mg), BINAP (30 mg) and cesium carbonate (190 mg) in 15 ml toluene was relaxed for 12 hours. The reaction mixture was eluted through a silica bed with Toluene and then with PE:EtOAc (1:1) and then with EtOAc. The toluene fraction was discarded and the solvent of the PE:EtOAc fraction was removed under reduced pressure. The crude product was purified by Combiflash (PE-THF). Yield 34 mg, 14%

$^1$H NMR (300 MHz, CDCl$_3$, rt) 3.76 (s, 6H, ArOCH$_3$), 5.01 (s, 1H, NH), 6.259 (s, 2H, ArH), 6.322 (s, broad, 1H, ArH), 6.92 (dd, 1H, J=2.1 Hz, J=8 Hz ArH), 6.98 (s, 1H, ArH), 7.365 (d, 1H, J=2.1 Hz, ArH), 7.537 (t, 1H, J=7.8, ArH), 7.61 (d, 1H, J=6 Hz, ArH), 7.79 (d, 1H, J=6 Hz, ArH), 7.88 (d, 1H, J=8.1 Hz, ArH), 8.51 (d, 1H, J=6 Hz, ArH), and 9.248 (s, 1H, ArH).

MS: m/z 504.2 (MH$^+$)

Synthesis of Compound 31

4-(2,3-Dihydro-indol-1-yl)-N-(tetrahydro-furan-2-ylmethyl)-2-trifluoromethyl-benzenesulfonamide a) 4-Bromo-2-trifluoromethyl-benzenesulfonyl chloride (250 mg, 0.77 mmol) was added in one portion to a stirred solution of tetrahydrofurylmethylamine (195 mg, 1.93 mmol) in dry THF (20 mL), under N$_2$ atmosphere. After 24 h at rt, water and EtOAc were added, and the layers were separated. The organic layer was washed with 1 N HCl and saturated NaCl solutions, dried over sodium sulfate, filtered and evaporated. The clean product was obtained as a yellow oil (290 mg, 97% Yield), transferred to the next step without further purification.

b) The product of step (a) (146 mg, 0.38 mmol) was dissolved in dry toluene (10 mL) under N$_2$ atmosphere. To the stirring solution were added Pd(OAc)$_2$ (8.5 mg, 0.038 mmol), BINAP (26 mg, 0.04 mmol) and cesium carbonate (154 mg, 0.48 mmol) and the reaction mixture was stirred at rt for 20 min. Indoline (52 mg, 0.43 mmol) was added and the mixture was stirred at rt for 10 min. Stirring was continued at 110° C. under N$_2$ atmosphere for 6 hours, cooled and allowed to proceed overnight at rt. The mixture was filtered through a small pad of silica gel on a sinter glass, eluted with additional amount of 30 mL toluene and then 50 mL petrol ether: EtOAc 1:1. 153 mg of yellowish crude oil obtained which was further purified using Combiflash (PE-THF) affording the clean desired product as a yellow oil (128 mg, 79% yield).

$^1$H NMR: (CDCl$_3$) δ 8.12 (d, 1H, CH); 7.64 (d, 1H, CH); 7.37-7.18 (m, 4H, CH); 6.96 (m, 1H, CH); 4.95 (t, 1H, NH); 4.07 (t, 2H, CH$_2$N); 3.98 (m, 1H, OCH); 3.77 (m, 2H, OCH$_2$); 3.23 (t, 2H, CH$_2$N); 3.16 (ddd, 1H, CH$_2$N); 2.95 (dt, 1H, CH$_2$N); 1.92 (m, 2H, CH$_2$); 1.67 (m, 2H, CH$_2$).

MS: m/z 427.20 (MH$^+$).

Synthesis of Compound 32

4-(Cyclopropylmethyl-propyl-amino)-N-(tetrahydro-furan-2-ylmethyl)-2-trifluoromethyl-benzenesulfonamide a) 4-Bromo-2-trifluoromethyl-benzenesulfonyl chloride (250 mg, 0.77 mmol) was added in one portion to a stirred solution of tetrahydrofurfurylamine (195 mg, 1.93 mmol) in dry THF (20 mL), under N$_2$ atmosphere. After 24 h at rt, water and EtOAc were added, and the layers were separated. The organic layer was washed with 1 N HCl and saturated NaCl solutions, dried over sodium sulfate, filtered and evaporated. The clean product was obtained as a yellow oil (290 mg, 97% Yield), transferred to the next step without further purification.

b) The product of step (a) (135 mg, 0.35 mmol) was dissolved in dry toluene (10 mL) under N$_2$ atmosphere. To the stirring solution were added Pd(OAc)$_2$ (7.8 mg, 0.035 mmol), BINAP (24 mg, 0.038 mmol) and cesium carbonate (141 mg, 0.43 mmol) and the reaction mixture was stirred at rt for 20 min. Cyclopropylmethyl-propyl-amine (45 mg, 0.40 mmol) was added and the mixture was stirred at rt for 10 min. Stirring was continued at 110° C. under N$_2$ atmosphere for 6 hours, cooled and allowed to proceed overnight at rt. The mixture was filtered through a small pad of silica gel on a sinter glass, eluted with additional amount of 30 mL toluene and then 50 mL petrol ether:EtOAc 1:1. 78 mg of yellowish crude oil obtained which was further purified using Combiflash (PE-THF) affording the clean desired product as a yellow oil (12 mg, 8% yield).

MS: m/z 421.20 (MH$^+$).

Synthesis of Compound 33

[4-(2,3-Dihydro-indole-1-sulfonyl)-3-trifluoromethyl-phenyl]-(3,5-dimethoxy-phenyl)-amine a) 4-Bromo-2-trifluoromethylbenzenesulfonyl chloride (200 mg) was added in one portion to a stirred solution of 2,3-Dihydro-1H-indole (222 mg) in THF (15 ml) under nitrogen at rt. The reaction mixture was stirred over night at the described conditions. Ethyl acetate (50 ml) was added and mixture was washed once with 1N HCl, water and brine. After drying over sodium sulfate solvent was removed under reduced pressure and the resulting crude (213 mg) was used in the next stage without further purification.

b) A mixture of the product of step (a) (213 mg), Pd(OAc)$_2$ (13 mg), BINAP (35 mg), cesium carbonate (221 mg) and 3,5-Dimethoxy-phenylamine (173 mg) in 15 ml toluene was relaxed for 12 hours. The reaction mixture was eluted through a silica bed with Toluene and then with PE:EtOAc (1:1). The toluene fraction was discarded and the solvent of the PE:EtOAc fraction was removed under reduced pressure. The crude product was purified by Combiflash (linear gradient PE-THF). Yield 160 mg, 60%

$^1$H NMR (300 MHz, CDCl3, rt) δ 3.08 (t, 2H, J=8.4 Hz, CH$_2$), 3.72 (s, 6H, ArOCH$_3$), 4.08 (t, 2H, J=8.7 Hz, CH$_2$), 6.27 (t, 1H, J=2.1 Hz, ArH), 6.32 (d, 2H, J=2.4 Hz, ArH), 6.98 (dt, 1H, J=0.9 Hz, J=7.5 Hz, ArH), 7.14 (m, 3H, ArH), 7.364 (s, 1H, ArH), 7.38 (d, 1H, J=6 Hz, ArH), and 7.89 (d, 1H, J=8.7 Hz, ArH).

MS: m/z 479.1 (MH$^+$)

Synthesis of Compound 34

4-(3,5-Dimethoxy-phenylamino)-N,N-bis-(2-methoxy-ethyl)-2-trifluoromethyl-benzenesulfonamide a) 4-Bromo-2-trifluoromethylbenzenesulfonyl chloride (200 mg) was added in one portion to a stirred solution of Bis-(2-methoxy-ethyl)-amine (248 mg) in THF (15 ml) under nitrogen at rt. The reaction mixture was stirred over night at the described conditions. Ethyl acetate (50 ml) was added and mixture was washed once with 1N HCl, water and brine. After drying over sodium sulfate solvent was removed under reduced pressure and the resulting crude (280 mg) was used in the next stage without further purification.

b) A mixture of the product of step (a) (280 mg), Pd(OAc)$_2$ (15 mg), BINAP (42 mg) cesium carbonate (260 mg) and 3,5-Dimethoxy-phenylamine (205 mg) in 15 ml toluene was relaxed for 12 hours. The reaction mixture was eluted through a silica bed with Toluene and then with PE:EtOAc (1:1). The toluene fraction was discarded and the solvent of the PE:EtOAc fraction was removed under reduced pressure. The crude product was purified by Combiflash (linear gradient PE-THF). Yield 270 mg, 82%.

$^1$H NMR (300 MHz, CDCl3, rt) δ 3.32 (s, 6H, ROCH$_3$), 3.54 (s broad, 8H, CH$_2$), 3.78 (s, 6H, ArOCH$_3$), 6.22 (s broad, 1H, NH), 6.27 (t, 1H, J=2.4 Hz, ArH), 6.33 (d, 2H, J=2.1 Hz, ArH), 7.17 (dd, 1H, J=2.4 Hz, J=8.7 Hz, ArH), 7.386 (d, 2H, J=2.4 Hz, ArH), and 7.96 (d, 2H, J=9 Hz, ArH).

MS: m/z 493.1 (MH$^+$)

Synthesis of Compound 35

4-(2,4-Dichloro-phenylamino)-N-(tetrahydro-pyran-4-ylmethyl)-2-trifluoromethyl-benzenesulfonamide a) To the solution of 1-aminomethyltetrahydropyran (284 mg. 2.46 mmol) in 15 ml THF 4-bromo-2-trifluoromethylbenzenesulfonyl chloride (381 mg, 1.17 mmol) was added in one portion and reaction mixture was stirred for a day. Ethyl acetate was added and mixture was washed twice with 1 N HCl, water and brine. After drying over sodium sulfate solvent was evaporated and crude solid used in the next stage. Yield 72%.

b) Mixture of the product of step (a) (202 mg, 0.50 mmol), 2,4-dichloroaniline (97 mg, 0.61 mmol), Pd(OAc)$_2$ (25 mg, 0.1 mmol), BINAP (62 mg, 0.1 mmol) and cesium carbonate (415 mg, 1.27 mmol) in 15 ml toluene was relaxed for 8 hours. Toluene was evaporated in vacuum and crude oil was purified by Combiflash (PE-THF). Yield 41%

$^1$H NMR: (CDCl$_3$) δ: 1.21-1.26 (2H, m, CH); 1.58-1.63 (2H, m, CH); 168-1.79 (1H, m, CH); 2.79-2.84(2H, m, CH); 3.29-3.38(2H, m, CH); 3.92-3.97 (2H, m, CH); 4.62 (1H, s, NH); 6.32 (1H, s, NH); 7.16-7.20(1H, dd, CH); 7.25-7.28 (1H, dd, CH); 7.29-7.35(1H, d, CH); 7.38-7.39 (1H, d, CH); 7.48-7.49 (1H, d, CH); 8.06-8.09 (1H, d, CH). Molecular ion observed [M–H]$^+$=483 consistent with the molecular formula C$_{19}$H$_{19}$Cl$_2$F$_3$N$_2$O$_3$S.

Synthesis of Compound 36

N-Cyclopropylmethyl-4-(2,4-difluoro-phenylamino)-2-trifluoromethyl-benzenesulfonamide Mixture of 4-bromo-N-cyclopropylmethyl-2-trifluoromethylbenzenesulfonamide (360 mg, 1.0 mmol), 2,4-difluoroaniline (156 mg, 1.2 mmol), Pd(OAc)$_2$ (26 mg, 0.11 mmol), BINAP (70 mg, 0.11 mmol) and cesium carbonate (350 mg, 1.07 mmol) in 15 ml toluene was relaxed for 6 hours. Toluene was evaporated in vacuum and crude oil was purified by Combiflash (PE-THF). Yield 61%

$^1$H NMR: (CDCl$_3$) δ: 0.08-0.13 (2H, m, CH); 0.45-0.52 (2H, m, CH); 0.86-0.91 (1H, m, CH); 2.81-2.85 (2H, dd, CH); 4.67 (1H, s, NH); 6.19 (1H, s, NH); 6.95-7.01 (3H, m, CH); 7.24-7.25 (1H, d, CH); 7.32-7.39 (1H, m, CH); 8.03-8.06(1H, d, CH). Molecular ion observed [M–H]$^+$=407 consistent with the molecular formula C$_{17}$H$_{15}$F$_5$N$_2$O$_2$S.

Synthesis of Compound 37

-(2,4-Difluoro-phenylamino)-N-furan-2-ylmethyl-benzenesulfonamide a) 4-Bromo-benzenesulfonyl chloride (255.5 mg, 1.0 mmol) was added in one portion to a stirred solution of furfurylamine (243 mg, 2.5 mmol) in dry THF (15 mL), under N$_2$ atmosphere. After 24 h at rt, water and EtOAc were added, and the layers were separated. The organic layer was washed with 1 N HCl and saturated NaCl solutions, dried over sodium sulfate, filtered and evaporated. The clean product was obtained as a yellow oil (310 mg, 98% yield), transferred to the next step without further purification.

b) The product of step (a) (144 mg, 0.46 mmol) was dissolved in dry toluene (10 mL) under N$_2$ atmosphere. To the stirring solution were added Pd(OAc)$_2$ (10.2 mg, 0.046 mmol), BINAP (31 mg, 0.05 mmol) and cesium carbonate (185 mg, 0.57 mmol) and the reaction mixture was stirred at rt for 20 min. 2,4-Difluoro-phenylamine (68 mg, 0.52 mmol) was added and the mixture was stirred at rt for 10 min. Stirring was continued at 110° C. under N$_2$ atmosphere for 6 hours, cooled and allowed to proceed overnight at rt. The mixture was filtered through a small pad of silica gel on a sinter glass, eluted with additional amount of 30 mL toluene and then 50 mL petrol ether:EtOAc 1:1. 86 mg of yellowish crude oil obtained which was further purified using Combiflash (PE-THF) affording the clean desired product as a yellow oil (38 mg, 23% yield).

$^1$H NMR: (CDCl$_3$) δ 7.68 (d, 1H, CH); 7.66 (m, 1H, CH); 7.33 (m, 2H, CH); 6.92 (m, 3H, CH); 6.89 (d, 1H, CH); 6.24 (dd, 1H, CH); 6.11 (d, 1H, CH); 4.17 (s, 2H, CH$_2$N).

MS: m/z 365.00 (MH$^+$).

Synthesis of Compound 38

4-(2,4-Difluoro-phenylamino)-N-furan-2-ylmethyl-2-trifluoromethyl-benzenesulfonamide a) 4-Bromo-2-trifluoromethyl-benzenesulfonyl chloride (250 mg, 0.77 mmol) was added in one portion to a stirred solution of furfurylamine (188 mg, 1.93 mmol) in dry THF (15 mL), under N$_2$ atmosphere. After 24 h at rt, water and EtOAc were added, and the layers were separated. The organic layer was washed with 1 N HCl and saturated NaCl solutions, dried over sodium sulfate, filtered and evaporated. The clean product was obtained as a yellow oil (296 mg, 100% yield), transferred to the next step without further purification.

b) The product of step (a) (146 mg, 0.38 mmol) was dissolved in dry toluene (10 mL) under N$_2$ atmosphere. To the stirring solution were added Pd(OAc)$_2$ (8.5 mg, 0.038 mmol), BINAP (26 mg, 0.042 mmol) and cesium carbonate (155 mg, 0.48 mmol) and the reaction mixture was stirred at rt for 20 min. 2,4-Difluoro-phenylamine (57 mg, 0.44 mmol) was added and the mixture was stirred at rt for 10 min. Stirring was continued at 110° C. under N$_2$ atmosphere for 6 hours, cooled and allowed to proceed overnight at rt. The mixture was filtered through a small pad of silica gel on a sinter glass, eluted with additional amount of 30 mL toluene and then 50 mL petrol ether:EtOAc 1:1. 113 mg of yellowish crude oil obtained which was further purified using Combiflash (PE-THF) affording the clean desired product as a yellow oil (95 mg, 58% yield).

$^1$H NMR: (CDCl$_3$) δ 7.99 (d, 1H, CH); 7.31 (m, 1H, CH); 7.21 (dd, 1H, CH); 7.18 (d, 1H, CH); 7.02-6.91 (m, 3H, CH); 6.20 (dd, 1H, CH); 6.05 (d, 1H, CH); 4.94 (t, 1H, NH); 4.19 (d, 2H, CH$_2$N).

MS: m/z 433.30 (MH$^+$).

Synthesis of Compound 39

N-Cyclopropylmethyl-4-(2,4-difluoro-phenylamino)-benzenesulfonamide a) 4-Bromo-N-cyclopropylmethyl-benzenesulfonamide (290 mg) was prepared and used in the next stage without further purification.

b) The product of step (a) (290 mg), Pd(OAc)$_2$ (22 mg), BINAP (62 mg), cesium carbonate (325 mg) in 15 ml toluene was stirred at rt under a nitrogen atmosphere for 15 min. 2,4-Difluoro-phenylamine (170 mg) was then added and the reaction mixture was relaxed for 3½ hours. The reaction mixture was eluted through a silica bed with Toluene and then with PE:EtOAc (1:1). The toluene fraction was discarded and the solvent of the PE:EtOAc fraction was removed under reduced pressure. The crude product was purified by Combiflash (linear gradient PE-THF). Yield 250 mg, 74%.

$^1$H NMR (300 MHz, CDCl3, rt) δ 0.094 (m, 2H, CH$_2$), 0.478 (m, 2H, CH$_2$), 0.91 (m, 1H, CH), 2.816 (d, 2H, J=6.9 Hz, CH$_2$) 6.92 (m, 4H, J=5.4 Hz, ArH), 7.433 (m, 1H, ArH), and 7.72 (dt, 2H, J=8.7 Hz, J=2.7 Hz, ArH).

MS: m/z

Synthesis of Compound 40

4-(Bicyclo[2.2.1]hept-2-ylamino)-N-cyclopropylmethyl-benzenesulfonamide a) 4-Bromo-N-cyclopropylmethyl-benzenesulfonamide (260 mg) was prepared by Alex and used in the next stage without further purification.

b) A mixture of the product of step (a) (260 mg), Pd(OAc)$_2$ (22 mg), BINAP (62 mg), cesium carbonate (326 mg) in 15 ml toluene was stirred at rt under a nitrogen atmosphere for 10 min. Exo-2-aminonorbornane (145 mg) was then added and the reaction mixture was relaxed for 4 hours and further stirred at rt for another 12 Hrs. The reaction mixture was eluted through a silica bed with Toluene and then with PE:EtOAc (1:1). The toluene fraction was discarded and the solvent of the PE:EtOAc fraction was removed under reduced pressure. The crude product was purified by flash chromatography (isocratic PE:EtOAc, 80:20). Yield 15 mg, 5%. The product is about 80% pure judging from its $^1$H-NMR spectrum.

$^1$H NMR (300 MHz, CDCl3, rt) δ 0.11 (m, 2H, CH$_2$), 0.49 (m, 2H, CH$_2$), 0.91 (m, 1H, CH), 1.2 (m, 5H, R), 1.58 (m, 2H, CH$_2$), 1.842 (ddd, 1H, J=9.9 Hz, J=12.9 Hz, J=2.1 Hz, CH), 2.345 (t, 2H, J=5.1 Hz, CH$_2$), 2.822 (d, 2H, J=7.2 Hz, CH$_2$) 3.1 (dd, 1H, J=3.3 Hz, J=7.2 Hz, CH), 6.79 (d, broad, 2H, J=7.5 Hz, ArH), and 7.672 (dt, 2H, J=8.7 Hz, J=2.1 Hz, ArH).

MS: m/z

Synthesis of Compound 41

4-(Bicyclo[2.2.1]hept-2-ylamino)-N-(tetrahydro-pyran-4-ylmethyl)-2-trifluoromethyl-benzene-sulfonamide Mixture of 4-bromo-N-(tetrahydropyran-4-ylmethyl)-2-trifluoromethylbenzenesulfonamide (151 mg, 0.37 mmol), aminonorbornane (101 mg, 0.90 mmol), Pd(OAc)$_2$ (24 mg, 0.10 mmol), BINAP (70 mg, 0.10 mmol) and cesium carbonate (404 mg, 1.24 mmol) in 20 ml toluene was relaxed for 6 hours. Toluene was evaporated in vacuum and crude oil was purified twice by Combiflash (PE-THF). Yield 62%

$^1$H NMR: (CDCl$_3$) δ: 1.19-1.30 (6H, m, CH); 1.43-1.79 (5H, m, CH); 1.83-1.86(2H, m, CH); 2.27-2.28 (2H, d, CH); 2.75-2.81 (2H, m, CH); 3.29-3.37(3H, m, CH); 3.92-3.96 (2H, m, CH); 4.58 (1H, s, NH); 6.72 (1H, d, CH); 6.95 (1H, s, CH); 7.94-7.97 (1H, d, CH). Molecular ion observed [M−H]$^+$=433 consistent with the molecular formula C$_{20}$H$_{27}$F$_3$N$_2$O$_3$S.

Synthesis of Compound 42

4-(Bicyclo[2.2.1]hept-2-ylamino)-N-furan-2-ylmethyl-2-trifluoromethyl-benzenesulfonamide and a) 4-Bromo-2-trifluoromethyl-benzenesulfonyl chloride (250 mg, 0.77 mmol) was added in one portion to a stirred solution of furfurylamine (188 mg, 1.93 mmol) in dry THF (15 mL), under N$_2$ atmosphere. After 24 h at rt, water and EtOAc were added, and the layers were separated. The organic layer was washed with 1 N HCl and saturated NaCl solutions, dried over sodium sulfate, filtered and evaporated. The clean product was obtained as a yellow oil (296 mg, 100% yield), transferred to the next step without further purification.

b) The product of step (a) (150 mg, 0.39 mmol) was dissolved in dry toluene (10 mL) under $N_2$ atmosphere. To the stirring solution were added Pd(OAc)$_2$ (8.8 mg, 0.039 mmol), BINAP (27 mg, 0.043 mmol) and cesium carbonate (159 mg, 0.49 mmol) and the reaction mixture was stirred at rt for 20 min. exo-2-Aminonorbornane (50 mg, 0.45 mmol) was added and the mixture was stirred at rt for 10 min. Stirring was continued at 110° C. under $N_2$ atmosphere for 6 hours, cooled and allowed to proceed overnight at rt. The mixture was filtered through a small pad of silica gel on a sinter glass, eluted with additional amount of 30 mL toluene and then 50 mL petrol ether:EtOAc 1:1. 140 mg of yellowish crude oil obtained which was further purified using Combiflash (PE-THF) affording the clean desired product as a yellow oil (39 mg, 24% yield).

$^1$H NMR: (CDCl$_3$) δ 7.94 (d, 1H, CH); 7.23 (dd, 1H, CH); 6.98 (d, 1H, CH); 6.88 (d, 1H, CH); 6.62 (dd, 1H, CH); 6.20 (dd, 1H, CH); 6.06 (dd, 1H, NH); 4.86 (t, 1H, NH); 4.14 (d, 2H, CH$_2$N); 3.29 (dd, 1H, CHN); 2.36 (bt, 1H, CH); 2.27 (s, 2H, CH); 1.89 (ddd, 1H, CH); 1.59 (m, 2H, CH); 1.45 (m, 2H, CH); 1.25 (m, 2H, CH).

MS: m/z 415 (MH$^+$).

Synthesis of Compound 43

4-(2-Chloro-4-cyano-phenylamino)-N-cyclopropylmethyl-2-trifluoromethyl-benzenesulfonamide a) 4-Bromo-2-trifluoromethylbenzenesulfonyl chloride (300 mg) was added in one portion to a stirred solution of C-Cyclopropyl-methylamine (132 mg) in THF (15 ml) under nitrogen at rt. The reaction mixture was stirred over night at the described conditions. Ethyl acetate (50 ml) was added and mixture was washed once with 1N HCl, water and brine. After drying over sodium sulfate solvent was removed under reduced pressure and the resulting crude (334 mg) was used in the next stage without further purification.

b) A mixture of the product of step (a) (111 mg), Pd(OAc)$_2$ (7 mg), BINAP (19 mg), cesium carbonate (120 mg) and 4-Amino-3-chloro-benzonitrile (95 mg) in 15 ml toluene was relaxed for 12 hours. The reaction mixture was eluted through a silica bed with Toluene and then with PE:EtOAc (1:1). The toluene fraction was discarded and the solvent of the PE:EtOAc fraction was removed under reduced pressure. The crude product was purified by Combiflash (linear gradient PE-THF). Yield 90 mg, 67%. Finally, it was recrystallized from acetonitrile: water (1:1). Yield: 38 mg of colorless flakes.

$^1$H NMR (300 MHz, CDCl3, rt) δ 0.12 (m, 2H, CH$_2$), 0.49 (m, 2H, CH$_2$), 0.9 (m, 1H, CH), 2.87 (dd, 2H, J=5.7 Hz, J=7.2 Hz, CH$_2$) 4.735 (t, 1H, J=5.4 Hz, NH), 6.754 (s broad, 1H, 5 NH), 7.402 (d, 1H, J=8.7 Hz, ArH), 7.431 (dd, 1H, J=2.1 Hz, J=8.6 Hz, ArH), 7.432 (dd, 1H, J=1.8 Hz, J=8.7 Hz, ArH), 7.586 (d, 1H, J=1.8 Hz, ArH), 7.736 (d, 1H, J=1.8 Hz, ArH), and 8.21 (d, 2H, J=8.7 Hz, ArH).

MS: m/z 428.1 (M$^-$)

Synthesis of Compound 44

N-cyclopropylmethyl-4-(2,4-dimethoxy-phenylamino)-2-trifluoromethyl-benzenesulfonamide a) 4-Bromo-2-trifluoromethylbenzenesulfonyl chloride (150 mg) was added in one portion to a stirred solution of C-Cyclopropyl-methylamine (70 mg) in THF (15 ml) under nitrogen at rt. The reaction mixture was stirred over night at the described conditions. Ethyl acetate (50 ml) was added and mixture was washed once with 1N HCl, water and brine. After drying over sodium sulfate solvent was removed under reduced pressure and the resulting crude (176 mg) was used in the next stage without further purification.

b) The product of step (a) (176 mg), Pd(OAc)$_2$ (11 mg), BINAP (31 mg), cesium carbonate (191 mg) and 2,4-dimethoxyaniline (176 mg) in 15 ml toluene was relaxed for 12 hours. The reaction mixture was eluted through a silica bed with Toluene and then with PE:EtOAc (1:1). The toluene fraction was discarded and the solvent of the PE:EtOAc fraction was removed under reduced pressure. The crude product was purified by Combiflash (linear gradient PE-THF). Yield 137.2 mg, 65%.

$^1$H NMR (300 MHz, CDCl3, rt) δ 0.12 (m, 2H, CH$_2$), 0.48 (m, 2H, CH$_2$), 0.85 (m, 1H, CH), 2.785 (d, 2H, J=6.9 Hz, CH$_2$) 3.826 (s, 3H, ArOCH$_3$), 3.838 (s, 3H, ArOCH$_3$), 4.621 (s broad, 1H, NH), 6.54 (m, 2H, ArH), 6.97 (dd, 1H, J=2.1 Hz, J=9 Hz, ArH), 7.224 (m, 1H, ArH), and 7.971 (d, 2H, J=9 Hz, ArH).

MS: m/z 431.1 (M$^+$)

Synthesis of Compound 45

N-cyclopropylmethyl-4-(2,4-dimethoxy-phenylamino)-N-propyl-2-trifluoromethyl-benzenesulfonamide a) 4-Bromo-2-trifluoromethylbenzenesulfonyl chloride (300 mg) was added in one portion to a stirred solution of Cyclopropylmethyl-propyl-amine (305 mg) in THF (15 ml) under nitrogen at rt. The reaction mixture was stirred over night at the described conditions. Ethyl acetate (50 ml) was added and mixture was washed once with 1N HCl, water and brine. After drying over sodium sulfate, the solvent was removed under reduced pressure and the resulting crude (376 mg) was used in the next stage without further purification.

b) A mixture of compound (a) (188 mg), Pd(OAc)$_2$ (10.5 mg), BINAP (29.2 mg), cesium carbonate (183 mg) and 2,4-Dimethoxy-phenylamine (144 mg) in 15 ml toluene was relaxed for 12 hours. The reaction mixture was eluted through a silica bed with Toluene and then with PE:EtOAc (1:1). The toluene fraction was discarded and the solvent of the PE:EtOAc fraction was removed under reduced pressure. The crude product was purified by Combiflash (linear gradient PE-THF). Yield 170 mg, 76%.

$^1$H NMR (300 MHz, CDCl3, rt) δ 0.16 (m, 2H, CH$_2$), 0.499 (m, 2H, CH$_2$), 0.831 (t, J=7.2 Hz, 3H, CH$_3$), 0.925 (m, 1H, CH), 1.58 (tq, 2H, J=7.5 Hz, J=7.2 Hz CH$_2$), 3.116 (d, 2H, J=6.9 Hz, CH$_2$), 3.293 (t, J=7.5 Hz, 2H, CH$_2$), 3.826 (s, 3H, ArOCH3), 3.833(s, 3H, ArOCH3), 6.526 (m, broad, 2H, ArH), 6.64 (d, broad, 1H, J=8.7 Hz, ArH), 7.21 (m, broad, 2H, ArH), 7.892 (d, 1H, J=8.7 Hz, ArH.

MS: m/z 473.1 (M$^+$)

Synthesis of Compound 46

N-cyclopropylmethyl-4-(4-morpholin-4-yl-phenylamino)-2-trifluoromethyl-benzenesulfonamide Mixture of 4-bromo-N-cyclopropylmethyl-2-trifluoromethylbenzenesulfonamide (360 mg, 1.0 mmol), 2,4-difluoroaniline (156 mg, 1.2 mmol), Pd(OAc)$_2$ (26 mg, 0.11 mmol), BINAP (70 mg, 0.11 mmol) and cesium carbonate (350 mg, 1.07 mmol) in 15 ml toluene was relaxed for 6 hours. Toluene was evaporated in vacuum and crude oil was purified by Combiflash (PE-THF). Yield 61%

$^1$H NMR: (CDCl$_3$) δ: 0.08-0.13 (2H, m, CH); 0.45-0.52 (2H, m, CH); 0.86-0.91 (1H, m, CH); 2.81-2.85 (2H, dd, CH); 4.67 (1H, s, NH); 6.19 (1H, s, NH); 6.95-7.01 (3H, m, CH); 7.24-7.25 (1H, d, CH); 7.32-7.39 (1H, m, CH); 8.03-8.06(1H, d, CH). Molecular ion observed [M−H]$^+$=407 consistent with the molecular formula C$_{17}$H$_{15}$F$_5$N$_2$O$_2$S.

Synthesis of Compound 47

N-cyclopropylmethyl-4-(2,3-dihydro-benzo[1.4] dioxin-6-ylamino)-2-trifluoromethyl-benzenesulfonamide a) 4-Bromo-N-cyclopropylmethyl-2-trifluoromethyl-benzenesulfonamide (100 mg) was prepared by Alex in a large batch and used in the next stage without further purification.

b) A mixture of compound (a) (100 mg), Pd(OAc)$_2$ (6.3 mg), BINAP (17 mg), cesium carbonate (110 mg) and 2,3-Dihydro-benzo[1,4]dioxin-6-ylamine (84 mg) in 15 ml toluene was relaxed for 12 hours. The reaction mixture was eluted through a silica bed with Toluene and then with PE:EtOAc (1:1). The toluene fraction was discarded and the solvent of the PE:EtOAc fraction was removed under reduced pressure. The crude product was purified by Combiflash (linear gradient PE-THF). Yield 87 mg, 74%.

$^1$H NMR (300 MHz, CDCl3, rt) δ 0.08 (m, 2H, CH$_2$), 0.48 (m, 2H, CH$_2$), 0.87 (m, 1H, CH), 2.799 (d, 2H, J=5.1 Hz, CH$_2$), 4.285 (s, 4H, 2×ArOCH$_2$), 4.62 (s, broad, 1H, NH), 6.71 (m, broad, 2H, ArH), 6.882 (d, 1H, J=8.7 Hz, ArH), 6.979 (m, broad, 1H, ArH), 7.190 (d, 1H, J=2.1 Hz, ArH) and 7.968 (d, 1H, J=8.7 Hz, ArH).

MS: m/z 429.0 (M$^+$)

Synthesis of Compound 48

N-Cyclopropylmethyl-4-[(6,6-dimethyl-bicyclo [3.1.1]hept-3-ylmethyl)-amino]-2-trifluoromethyl-benzenesulfonamide Mixture of 4-bromo-N-cyclopropylmethyl-2-trifluoromethylbenzenesulfonamide (200 mg, 0.55 mmol), (−)-cis-myrtanylamine (153 mg, 1.0 mmol), Pd(OAc)$_2$ (26 mg, 0.1 mmol), BINAP (62 mg, 0.1 mmol) and cesium carbonate (401 mg, 1.26 mmol) in 15 ml toluene was relaxed for 6 hours. Toluene was evaporated in vacuum and crude oil was purified by Combiflash (PE-THF). Yield 42%

$^1$H NMR (CDCl$_3$) δ: 0.08-0.13 (2H, m, CH); 0.45-0.52 (2H, m, CH); 0.86-0.91 (1H, m, CH); 2.81-2.85 (2H, dd, CH); 4.67 (1H, s, NH); 6.19 (1H, s, NH); 6.95-7.01 (3H, m, CH); 7.24-7.25 (1H, d, CH); 7.32-7.39 (1H, m, CH); 8.03-8.06(1H, d, CH). Molecular ion observed [M−H]$^+$=456 consistent with the molecular formula C$_{17}$H$_{15}$F$_5$N$_2$O$_2$S.

Synthesis of Compound 49

4-(4-Hydroxy-cyclohexylamino)-N-(tetrahydro-pyran-4-ylmethyl)-2-trifluoromethyl-benzenesulfonamide Mixture of 4-bromo-N-tetrahydrocyclopyranylmethyl-2-trifluoromethylbenzene sulfonamide (200 mg, 0.5 mmol), 4-tert-Butyldimethylsilanyloxy)-cyclohexylamine (176 mg, 0.76 mmol), Pd(OAc)$_2$ (22 mg, 0.1 mmol), BINAP (62 mg, 0.1 mmol) and cesium carbonate (431 mg, 1.32 mmol) in 15 ml toluene was relaxed for 6 hours. Toluene was evaporated in vacuum, crude oil was dissolved in THF and 2 ml of tetrabutylammonium fluoride in THF was added. Mixture was stirred overnight. After removing off solvent crude oil was purified by Combiflash (PE-THF). Yield 41%

NMR (CDCl$_3$) δ: 1.21-1.56 (8H, m, CH); 1.58-1.63 (4H, m, CH); 1.68-1.79 (1H, m, CH); 2.79-2.84(2H, m, CH); 3.23-3.38(3H, m, CH); 3.25-3.58 (1H, m, CH); 3.92-3.97 (2H, m, CH); 4.67 (1H, s, NH); 5.02(1H, s, OH); 6.98 (1H, s, CH); 7.00-7.03 (1H, d, CH); 7.21-7.24 (1H, m, NH); 7.98-8.09 (1H, d, CH). Molecular ion observed [M−H]$^+$=437 consistent with the molecular formula C$_{19}$H$_{27}$F$_3$N$_2$O$_4$S.

Synthesis of Compound 50

4-(2,4-Dichloro-phenylamino)-N-(3-dimethylamino-2,2-dimethyl-propyl)-2-trifluoromethyl-benzenesulfonamide a) 4-Bromo-2-trifluoromethylbenzenesulfomyl chloride (500 mg) was added in one portion to a stirred solution of N,N,2,2-Tetramethyl-1,3-propanediamine (1.82 g) in THF (30 ml) under nitrogen at rt. The reaction mixture was stirred over night at the described conditions. Ethyl acetate (50 ml) was added and mixture was washed once with NaHCO23, water and brine. After drying over sodium sulfate, the solvent was removed under reduced pressure and a fraction of the resulting crude (yield: 666 mg) was used in the next stage without further purification.

b) A mixture of the product of step (a) (196 mg), Pd(OAc)$_2$ (10.5 mg), BINAP (29.2 mg), cesium carbonate (183 mg) and 2,4-Dichloro-phenylamine (152 mg) in 15 ml toluene was relaxed for 12 hours. The reaction mixture was eluted through a silica bed with Toluene and then with PE:EtOAc (1:1). The toluene fraction was discarded and the solvent of the PE:EtOAc fraction was removed under reduced pressure. The crude product was purified by Combiflash (linear gradient PE-THF). Yield 85 mg, 36%.

$^1$H NMR (300 MHz, CDCl3, rt) δ 1.43 (s, 6H, CH$_3$), 1.608, 2.963, and 3.08 (broad signals, 10H), 6.401 (s, broad, 1H, NH), 6.96 (m, broad, 1H, ArH), 7.24 (m, broad, 2H, ArH), 7.355 (d, broad, 2H, ArH), 7.47 (d, 1H, J=2.4 Hz, ArH.

MS: m/z 498.1 (M$^+$)

Synthesis of Compound 51

4-(2-Chloro-pyridin-3-ylamino)-N-(tetrahydro-pyran-4-ylmethyl)-2-trifluoromethyl-benzenesulfonamide a) 4-Bromo-2-trifluoromethyl-benzenesulfonyl chloride (647 mg, 2.0 mmol) was added in one portion to a stirred solution of 4-amino-methyltetrahydropyran (460 mg, 4.0 mmol) in dry THF (25 mL), under N$_2$ atmosphere. After 24 h at rt, water and EtOAc were added, and the layers were separated. The organic layer was washed with 1 N HCl and saturated NaCl solutions, dried over sodium sulfate, filtered and evaporated. The clean product was obtained as a yellow oil (705 mg, 88% yield), transferred to the next step without further purification.

b) The product of step (a) (100 mg, 0.25 mmol) was dissolved in dry toluene (10 mL) under N$_2$ atmosphere. To the stirring solution were added Pd(OAc)$_2$ (5.6 mg, 0.025 mmol), BINAP (17 mg, 0.028 mmol) and cesium carbonate (102 mg, 0.31 mmol) and the reaction mixture was stirred at rt for 20 min. 3-Amino-2-chloro-pyridine (37 mg, 0.29 mmol) was added and the mixture was stirred at rt for 10 min. Stirring was continued at 110° C. under N$_2$ atmosphere for 6 hours, cooled and allowed to proceed overnight at rt. The mixture was filtered through a small pad of silica gel on a sinter glass, eluted with additional amount of 30 mL toluene and then 50 mL EtOAc. 118 mg of yellowish crude oil obtained which was further purified using Combiflash (PE-THF) affording the clean desired product as a yellow oil (25 mg, 22% yield).

$^1$H NMR: (CDCl$_3$) δ 8.16 (dd, 1H, CH); 8.13 (d, 1H, CH); 7.75 (dd, 1H, CH); 7.49 (d, 1H, CH); 7.31 (dd, 1H, CH); 7.00 (s, 1H, CH); 6.52 (bs, 1H, NH); 4.69 (t, 1H, NH); 3.97 (dd, 2H, OCH$_2$); 3.36 (dt, 2H, OCH$_2$); 2.85 (t, 2H, CH$_2$N); 1.76 (m, 1H, CH); 1.63 (m, 2H, CH$_2$); 1.26 (m, 2H, CH$_2$).

MS: m/z 450.00 (MH$^+$).

Synthesis of Compound 52

4-(2-Ethyl-2H-pyrazol-3-ylamino)-N-(tetrahydro-pyran-4-ylmethyl)-2-trifluoromethyl-benzene-sulfonamide a) 4-Bromo-2-trifluoromethyl-benzenesulfonyl chloride (647 mg, 2.0 mmol) was added in one portion to a stirred solution of 4-amino-methyltetrahydropyran (460 mg, 4.0 mmol) in dry THF (25 mL), under N$_2$ atmosphere. After 24 h at rt, water and EtOAc were added, and the layers were separated. The organic layer was washed with 1 N HCl and saturated NaCl solutions, dried over sodium sulfate, filtered and evaporated. The clean product was obtained as a yellow oil (705 mg, 88% yield), transferred to the next step without further purification.

b) The product of step (a) (100 mg, 0.25 mmol) was dissolved in dry toluene (10 mL) under N$_2$ atmosphere. To the stirring solution were added Pd(OAc)$_2$ (5.6 mg, 0.025 mmol), BINAP (17 mg, 0.028 mmol) and cesium carbonate (102 mg, 0.31 mmol) and the reaction mixture was stirred at rt for 20 min. 3-Amino-2-ethyl-pyrazole (32 mg, 0.29 mmol) was added and the mixture was stirred at rt for 10 min. Stirring was continued at 110° C. under N$_2$ atmosphere for 6 hours, cooled and allowed to proceed overnight at rt. The mixture was filtered through a small pad of silica gel on a sinter glass, eluted with additional amount of 30 mL toluene and then 50 mL EtOAc. 88 mg of yellowish crude oil obtained which was further purified using Combiflash (PE-THF) affording the clean desired product as a yellow oil (67 mg, 62% yield).

$^1$H NMR: (CDCl$_3$) δ 8.02 (d, 1H, CH); 7.58 (d, 1H, CH); 7.22 (d, 1H, CH); 6.91 (dd, 1H, CH); 6.52 (bs, 1H, NH); 6.14 (d, 1H, CH); 4.68 (t, 1H, NH); 4.11 (q, 2H, NCH$_2$CH$_3$); 3.95 (dd, 2H, CH$_2$O); 3.34 (dt, 2H, CH$_2$O); 2.81 (t, 2H, CH$_2$N); 1.73 (m, 1H, CH); 1.60 (m, 2H, CH$_2$); 1.41 (t, 3H, NCH$_2$CH$_3$); 1.23 (m, 2H, CH$_2$).

MS: m/z 433.10 (MH$^+$).

Synthesis of Compound 53

4-(Cyclopropylmethyl-propyl-amino)-N-(tetrahydro-pyran-4-ylmethyl)-2-trifluoromethyl-benzene-sulfonamide a) 4-Bromo-2-trifluoromethyl-benzenesulfonyl chloride (647 mg, 2.0 mmol) was added in one portion to a stirred solution of 4-amino-methyltetrahydropyran (460 mg, 4.0 mmol) in dry THF (25 mL), under N$_2$ atmosphere. After 24 h at rt, water and EtOAc were added, and the layers were separated. The organic layer was washed with 1 N HCl and saturated NaCl solutions, dried over sodium sulfate, filtered and evaporated. The clean product was obtained as a yellow oil (705 mg, 88% yield), transferred to the next step without further purification.

b) The product of step (a) (200 mg, 0.5 mmol) was dissolved in dry toluene (15 mL) under N$_2$ atmosphere. To the stirring solution were added Pd(OAc)$_2$ (11.2 mg, 0.05 mmol), BINAP (34 mg, 0.055 mmol) and cesium carbonate (203 mg, 0.63 mmol) and the reaction mixture was stirred at rt for 20 min. Cyclopropylmethyl-propyl-amine (226 mg, 2.0 mmol) was added and the mixture was stirred at rt for 10 min. Stirring was continued at 110° C. under N$_2$ atmosphere for 6 hours, cooled and allowed to proceed overnight at rt. The mixture was filtered through a small pad of silica gel on a sinter glass, eluted with additional amount of 30 mL toluene and then 50 mL EtOAc. 132 mg of yellowish crude oil obtained which was further purified using Combiflash (PE-THF) affording the clean desired product as a yellow oil (48 mg, 22% yield).

$^1$H NMR: (CDCl$_3$) δ 8.08 (d, 1H, CH); 7.09 (d, 1H, CH); 6.83 (dd, 1H, CH); 4.57 (t, 1H, NH); 3.95 (m, 2H, OCH$_2$); 3.38 (m, 2H, CH$_2$N); 3.30 (t, 2H, OCH$_2$); 2.84 (t, 2H, CH$_2$N); 2.78 (t, 2H, CH$_2$N); 1.72 (m, 1H, CH); 1.67 (m, 2H, CH$_2$CH$_2$N); 1.60 (m, 2H, CH$_2$); 1.26 (m, 3H, CH+CH$_2$); 0.96 (t, 3H, CH$_3$); 0.61 (m, 2H, CH$_2$); 0.25 (m, 2H, CH$_2$).

MS: m/z 435.20 (MH$^+$).

Synthesis of Compound 54

4-(3,5-Dimethoxy-phenylamino)-N-(tetrahydro-pyran-4-ylmethyl)-2-trifluoromethyl-benzenesulfona-mide a) 4-Bromo-2-trifluoromethyl-benzenesulfonyl chloride (647 mg, 2.0 mmol) was added in one portion to a stirred solution of 4-amino-methyltetrahydropyran (460 mg, 4.0 mmol) in dry THF (25 mL), under N$_2$ atmosphere. After 24 h at rt, water and EtOAc were added, and the layers were separated. The organic layer was washed with 1 N HCl and saturated NaCl solutions, dried over sodium sulfate, filtered and evaporated. The clean product was obtained as a yellow oil (705 mg, 88% yield), transferred to the next step without further purification.

b) The product of step (a) (100 mg, 0.25 mmol) was dissolved in dry toluene (10 mL) under N$_2$ atmosphere. To the stirring solution were added Pd(OAc)$_2$ (5.6 mg, 0.025 mmol), BINAP (17 mg, 0.028 mmol) and cesium carbonate (102 mg, 0.31 mmol) and the reaction mixture was stirred at rt for 20 min. 3,5-Dimethoxyaniline (44 mg, 0.29 mmol) was added and the mixture was stirred at rt for 10 min. Stirring was continued at 110° C. under N$_2$ atmosphere for 6 hours, cooled and allowed to proceed overnight at rt. The mixture was filtered through a small pad of silica gel on a sinter glass, eluted with additional amount of 30 mL toluene and then 50 mL EtOAc. 167 mg of yellowish crude oil obtained which was further purified using Combiflash (PE-THF) affording the clean desired product as a yellow oil (80 mg, 67% yield).

$^1$H NMR: (CDCl$_3$) δ 8.01 (d, 1H, CH); 7.37 (d, 1H, CH); 7.18 (dd, 1H, CH); 6.33 (d, 2H, CH); 6.27 (t, 1H, CH); 4.62 (t, 1H, NH); 3.93 (m, 2H, OCH$_2$); 3.79 (s, 6H, OCH$_3$); 3.34 (dt,

2H, OCH$_2$); 2.81 (t, 2H, CH$_2$N); 1.73 (m, 1H, CH); 1.61 (m, 2H, CH$_2$); 1.24 (m, 2H, CH$_2$).
MS: m/z 475.10 (MH$^+$).

Synthesis of Compound 55

4-(4-Dimethylamino-phenylamino)-N-(tetrahydro-pyran-4-ylmethyl)-2-trifluoromethyl-benzene-sulfonamide a) 4-Bromo-2-trifluoromethyl-benzenesulfonyl chloride (647 mg, 2.0 mmol) was added in one portion to a stirred solution of 4-amino-methyltetrahydropyran (460 mg, 4.0 mmol) in dry THF (25 mL), under N$_2$ atmosphere. After 24 h at rt, water and EtOAc were added, and the layers were separated. The organic layer was washed with 1 N HCl and saturated NaCl solutions, dried over sodium sulfate, filtered and evaporated. The clean product was obtained as a yellow oil (705 mg, 88% yield), transferred to the next step without further purification.
b) The product of step (a) (100 mg, 0.25 mmol) was dissolved in dry toluene (10 mL) under N$_2$ atmosphere. To the stirring solution were added Pd(OAc)$_2$ (5.6 mg, 0.025 mmol), BINAP (17 mg, 0.028 mmol) and cesium carbonate (102 mg, 0.31 mmol) and the reaction mixture was stirred at rt for 20 min. N,N-Dimethyl-phenylene-1,4-diamine (40 mg, 0.29 mmol) was added and the mixture was stirred at rt for 10 min. Stirring was continued at 110° C. under N$_2$ atmosphere for 6 hours, cooled and allowed to proceed overnight at rt. The mixture was filtered through a small pad of silica gel on a sinter glass, eluted with additional amount of 30 mL toluene and then 50 mL EtOAc. 230 mg of yellowish crude oil obtained which was further purified using Combiflash (PE-THF) affording the clean desired product as a yellow oil (44 mg, 38.5% yield).
MS: m/z 458.10 (MH$^+$).

Synthesis of Compound 56

4-(2-Chloro-4-cyano-phenylamino)-N-(tetrahydro-pyran-4-ylmethyl)-2-trifluoromethyl-benzene-sulfonamide a) 4-Bromo-2-trifluoromethyl-benzenesulfonyl chloride (647 mg, 2.0 mmol) was added in one portion to a stirred solution of 4-amino-methyltetrahydropyran (460 mg, 4.0 mmol) in dry THF (25 mL), under N$_2$ atmosphere. After 24 h at rt, water and EtOAc were added, and the layers were separated. The organic layer was washed with 1 N HCl and saturated NaCl solutions, dried over sodium sulfate, filtered and evaporated. The clean product was obtained as a yellow oil (705 mg, 88% yield), transferred to the next step without further purification.
b) The product of step (a) (110 mg, 0.27 mmol) was dissolved in dry toluene (10 mL) under N$_2$ atmosphere. To the stirring solution were added Pd(OAc)$_2$ (6.2 mg, 0.027 mmol), BINAP (19 mg, 0.03 mmol) and cesium carbonate (111 mg, 0.34 mmol) and the reaction mixture was stirred at rt for 20 min. 4-Amino-3-chloro-benzonitrile (48 mg, 0.31 mmol) was added and the mixture was stirred at rt for 10 min. Stirring was continued at 110° C. under N$_2$ atmosphere for 6 hours, cooled and allowed to proceed overnight at rt. The mixture was filtered through a small pad of silica gel on a sinter glass, eluted with additional amount of 30 mL toluene and then 50 mL EtOAc. 141 mg of yellowish crude oil obtained which was further purified using Combiflash (PE-THF) affording the clean desired product as a yellow oil (39 mg, 30.5% yield).
$^1$H NMR: (CDCl$_3$) δ 8.19 (d, 1H, CH); 7.74 (d, 1H, CH); 7.59 (d, 1H, CH); 7.54 (dd, 1H, CH); 7.44 (dd, 1H, CH); 7.41 (d, 1H, CH); 6.79 (bs, 1H, NH); 4.71 (t, 1H, NH); 3.96 (dd, 2H, OCH$_2$); 3.35 (dt, 2H, OCH$_2$); 2.86 (t, 2H, CH$_2$N); 1.75 (m, 1H, CH); 1.62 (m, 2H, CH$_2$); 1.25 (m, 2H, CH$_2$).
MS: m/z 471.90 (MH$^-$).

Synthesis of Compound 57

N-Cyclopropylmethyl-4-(2,4-dichloro-phenylamino)-N-methyl-2-trifluoromethyl-benzene-sulfonamide To a solution of N-Cyclopropylmethyl-4-(2,4-dichloro-phenylamino)-2-trifluoromethyl-benzenesulfonamide, (256 mg. 0.58 mmol), methyl iodide (92 mg, 0.65 mmol) and tetrabutylammonium hydrosulfate (38 mg, 0.11 mmol) in 15 ml dichloromethane 3 ml 25% solution of NaOH was added and mixture was stirred for 3 hours. Water was added and mixture was washed twice with 1 N HCl and brine. After drying over sodium sulfate solvent was evaporated and crude solid used in the next stage. Yield 97%.
NMR (CDCl$_3$) δ: 0.09-0.13 (2H, m, CH); 0.45-0.51 (2H, m, CH); 0.89 (1H, m, CH); 2.91 (3H, s, CH); 3.08-3.10 (2H, d, CH); 6.29 (1H, s, NH); 7.16-7.19 (1H, dd, CH); 7.24-7.28 (3H, m, CH); 7.32-7.39 (2H, m, CH); 7.51 (1H, d, CH); 8.09 (1H, d, CH). Molecular ion observed [M–H]$^+$=453 consistent with the molecular formula C$_{18}$H$_{17}$Cl$_2$F$_3$N$_2$O$_2$S.

Synthesis of Compound 58

4-(Bicyclo[2.2.1]hept-2-ylamino)-N-cyclopropylmethyl-2-trifluoromethyl-benzenesulfonamide Mixture of 4-bromo-N-cyclopropylmethyl-2-trifluoromethylsulfonamide (196 mg, 0.54 mmol), 2-aminonorbornane (115 mg, 1.03 mmol), Pd(OAc)$_2$ (25 mg, 0.1 mmol), BINAP (69 mg, 0.1 mmol) and cesium carbonate (415 mg, 1.27 mmol) in 15 ml toluene was relaxed for 8 hours. Toluene was evaporated in vacuum and crude oil was purified by Combiflash (PE-THF). Yield 41%
NMR (CDCl$_3$) δ: 0.43-0.49 (2H, m, CH); 0.84-0.92 (2H, m, CH); 1.16-1.31 (5H, m, CH); 1.48-1.63 (3H, m, CH); 1.83-1.90 (1H, m, CH); 2.30-2.62(2H, d, CH); 2.78-2.80(2H, m, CH); 3.27-3.31 (1H, m, CH); 4.62 (1H, s, NH); 6.74(1H, m, CH); 7.01 (1H, s, CH); 7.96-7.99(1H, d, CH); Molecular ion observed [M–H]$^+$=489 consistent with the molecular formula C$_{18}$H$_{23}$F$_3$N$_2$O$_3$S.

Synthesis of Compound 59

N-Cyclopropylmethyl-4-(2,4-dimethoxy-phenylamino)-2-methyl-benzenesulfonamide a) 4-Bromo-2-methyl-benzenesulfonyl chloride (538 mg) was added in one portion to a stirred solution of C-Cyclopropyl-methylamine (142 mg) in THF (15 ml) under nitrogen at rt. The reaction mixture was stirred over night at the described conditions. Ethyl acetate (50 ml) was added and mixture was washed once with HCl 1N, water and brine. After drying over sodium sulfate, the solvent was removed under reduced pressure and a fraction of the resulting crude (yield: 550 mg) was used in the next stage without further purification.

b) A mixture of compound (a) (85 mg), Pd(OAc)$_2$ (6.3 mg), BINAP (17 mg), cesium carbonate (110 mg) and 3,5-Dimethoxy-phenylamine (85 mg) in 15 ml toluene was relaxed for 12 hours. The reaction mixture was eluted through a silica bed with Toluene and then with PE:EtOAc (1:1). The toluene fraction was discarded and the solvent of the PE:EtOAc fraction was removed under reduced pressure. The crude product was purified by Combiflash (linear gradient PE-THF). Yield 42 mg, 40%.

$^1$H NMR (300 MHz, CDCl3, rt) δ 0.095 (m, 2H, CH$_2$), 0.48 (m, 2H, CH$_2$), 0.89 (m, 1H, CH), 2.58 (s, 3H, CH$_3$), 2.79 (d, 2H, J=7.2 Hz, CH$_2$) 3.78 (s, 6H, ArOCH$_3$), 6.199 (t, 1H, J=1.8 Hz, ArH), 6.31 (d, 2H, J=2.1 Hz ArH), 76.9 (m, 2H, ArH), and 7.82 (d, 2H, J=9.3 Hz, ArH).

MS: m/z 377.2 (M$^+$)

Synthesis of Compound 60

4-(2,4-Dichloro-phenylamino)-2-trifluoromethyl-benzenesulfonamide a) 4-Bromo-2-trifluoromethyl-benzenesulfonyl chloride (323.5 mg, 1.0 mmol) was added in one portion to a stirred solution of NH$_3$/MeOH (5 mL), under N$_2$ atmosphere. After 24 h at rt, water and EtOAc were added, and the layers were separated. The organic layer was washed with 1 N HCl and saturated NaCl solutions, dried over sodium sulfate, filtered and evaporated. The clean product was obtained as a white solid (260 mg, 86% yield), transferred to the next step without further purification.

b) The product of step (a) (130 mg, 0.43 mmol) was dissolved in dry toluene (10 mL) under N$_2$ atmosphere. To the stirring solution were added Pd(OAc)$_2$ (9.6 mg, 0.043 mmol), BINAP (29 mg, 0.047 mmol) and cesium carbonate (174 mg, 0.53 mmol) and the reaction mixture was stirred at rt for 20 min. 2,4-Dichloroaniline (80 mg, 0.49 mmol) was added and the mixture was stirred at rt for 10 min. Stirring was continued at 110° C. under N$_2$ atmosphere for 6 hours, cooled and allowed to proceed overnight at rt. The mixture was filtered through a small pad of silica gel on a sinter glass, eluted with additional amount of 30 mL toluene and then 50 mL EtOAc. 79 mg of yellowish crude oil obtained which was further purified using Combiflash (PE-THF) affording the clean desired product as a yellow oil (13 mg, 7.5% yield).

MS: m/z 384.90 (MH$^+$).

Synthesis of Compound 61

4-(Bicyclo[2.2.1]hept-2-ylamino)-2-trifluoromethyl-benzenesulfonamide a) 4-Bromo-2-trifluoromethyl-benzenesulfonyl chloride (323.5 mg, 1.0 mmol) was added in one portion to a stirred solution of NH$_3$/MeOH (5 mL), under N$_2$ atmosphere. After 24 h at rt, water and EtOAc were added, and the layers were separated. The organic layer was washed with 1 N HCl and saturated NaCl solutions, dried over sodium sulfate, filtered and evaporated. The clean product was obtained as a white solid (260 mg, 86% yield), transferred to the next step without further purification.

b) The product of step (a) (130 mg, 0.43 mmol) was dissolved in dry toluene (10 mL) under N$_2$ atmosphere. To the stirring solution were added Pd(OAc)$_2$ (9.6 mg, 0.043 mmol), BINAP (29 mg, 0.047 mmol) and cesium carbonate (170 mg, 0.53 mmol) and the reaction mixture was stirred at rt for 20 min. exo-2-Aminonorbornane (55 mg, 0.49 mmol) was added and the mixture was stirred at rt for 10 min. Stirring was continued at 110° C. under N$_2$ atmosphere for 6 hours, cooled and allowed to proceed overnight at rt. The mixture was filtered through a small pad of silica gel on a sinter glass, eluted with additional amount of 30 mL toluene and then 50 mL EtOAc. 46 mg of yellowish crude oil obtained which was further purified using Combiflash (PE-THF) affording the clean desired product as a yellow oil (22 mg, 15% yield).

MS: m/z 335.10 (MH$^+$).

Synthesis of Compound 62

4-(1-Aza-bicyclo[2.2.2]oct-3-ylamino)-N-(tetrahydro-pyran-4-ylmethyl)-2-trifluoromethyl-benzenesulfonamide Mixture of 4-bromo-N-cyclopropylmethyl-2-trifluoromethylsulfonamide (196 mg, 0.51 mmol), aminoquinuclidine (127 mg, 0.63 mmol), Pd(OAc)$_2$ (23 mg, 0.1 mmol), BINAP (62 mg, 0.1 mmol) and cesium carbonate (821 mg, 2.52 mmol) in 15 ml toluene was relaxed for 8 hours. Toluene was evaporated in vacuum and crude oil was purified by Combiflash (PE-THF). Yield 29%

NMR (CDCl$_3$) δ: 1.03-1.10 (2H, m, CH); 1.51-1.80 (4H, m, CH); 1.90-1.92 (2H, m, CH); 2.07-2.08 (1H, m, CH); 2.15-2.17 (1H, m, CH); 2.62-2.67(2H, t, CH); 2.94-2.98 (1H, m, CH); 3.15-3.25 (5H, m, CH); 3.67-3.81(3H, m, CH); 3.98 (1H, m, CH); 6.87-6.91(1H, dd, CH); 7.11-7.12 (1H, d, CH); 7.75-7.79(1H, d, CH); 10.19 (1H, s, NH). Molecular ion observed [M−H]$^+$=448 consistent with the molecular formula C$_{20}$H$_{28}$F$_3$N$_2$O$_3$S.

Synthesis of Compound 63

N-Adamantan-1-yl-4-(2,4-dichloro-phenylamino)-2-trifluoromethyl-benzenesulfonamide a) To the solution of adamantylamine (186 mg. 1.24 mmol) in 15 ml THF 4-bromo-2-trifluoromethylbenzenesulfonyl chloride (341 mg, 1.05 mmol) was added in one portion and reaction mixture was stirred for a day. Ethyl acetate was added and mixture was washed twice with 1 N HCl, water and brine. After drying over sodium sulfate solvent was evaporated and crude solid used in the next stage. Yield 89%.

b) Mixture of the product of step (a) (300 mg, 0.63 mmol), 2,4-dichloroaniline (194 mg, 1.19 mmol), Pd(OAc)$_2$ (25 mg, 0.11 mmol), BINAP (75 mg, 0.13 mmol) and cesium carbonate (329 mg, 1.02 mmol) in 15 ml toluene was relaxed for 6 hours. Toluene was evaporated in vacuum and crude oil was purified by Combiflash (PE-THF). Yield 62%

NMR (CDCl$_3$) δ: 1.60 (6H, s, CH); 1.82-1.83 (6H, d, CH); 2.04 (3H, s, CH); 4.55 (1H, s, NH); 6.31 (1H, s, NH); 7.19-7.20 (1H, dd, CH); 7.22-7.29 (2H, dd, CH); 7.35-7.39 (2H, m, CH); 7.48-7.49(1H, d, CH); 8.16-8.19 (1H, d, CH). Molecular ion observed [M−H]$^+$=519 consistent with the molecular formula C$_{23}$H$_{23}$Cl$_2$F$_3$N$_2$O$_2$S.

Synthesis of Compound 64

4-(2,4-Dichloro-phenylamino)-N-(1,1,3,3-tetramethyl-butyl)-2-trifluoromethyl-benzenesulfonamide a) 4-Bromo-2-trifluoromethylbenzenesulfomyl chloride (300 mg) was added in one portion to a stirred solution of 1,1,3,3-Tetramethyl-butylamine (350 mg) in THF (15 ml) under nitrogen at rt. The reaction mixture was stirred over night at the described conditions. Ethyl acetate (50 ml) was added and mixture was washed once with HCl 1N, water and brine. After drying over sodium sulfate, the solvent was removed under reduced pressure and a fraction of the resulting crude (yield: 356 mg) was used in the next stage without further purification.

b) A mixture of compound (a) (350 mg), Pd(OAc)$_2$ (18 mg), BINAP (52 mg), cesium carbonate (328 mg) and 2,4-Dichloro-phenylamine (275 mg) in 15 ml toluene was relaxed for 12 hours. The reaction mixture was eluted through a silica bed with Toluene and then with PE:EtOAc (70:30). The toluene fraction was discarded and the solvent of the PE:EtOAc fraction was removed under reduced pressure. The crude product was purified by Combiflash (linear gradient PE-THF). Yield 285 mg, 68%.

$^1$H NMR (300 MHz, CDCl3, rt) δ 1.025 (s, 9H, 3CH$_3$), 1.279 (s, 6H, 2CH$_3$), 1.855 (m, 1H, CH$_2$), 1.3.749 (m, 1H, CH$_2$), 4.317 (s, broad, 1H, NH), 6.31 (s, broad, 1H, NH), 7.18 (m, 1H, ArH), 7.21 (m, 1H, ArH), 7.346 (m, 2H, ArH), 7.474 (d, 1H, J=2.4 Hz, ArH), 8.13 (d, 1H, J=9 Hz, ArH).

Synthesis of Compound 65

4-(2,4-Dichloro-phenylamino)-N-phenyl-2-trifluoromethyl-benzenesulfonamide a) 4-Bromo-2-trifluoromethyl-benzenesulfonyl chloride (100 mg, 0.31 mmol) was added in one portion to a stirred solution of aniline (86 mg, 0.93 mmol) in dry THF (6 mL), under N$_2$ atmosphere. After 24 h at rt, water and EtOAc were added, and the layers were separated. The organic layer was washed with 1 N HCl and saturated NaCl solutions, dried over sodium sulfate, filtered and evaporated. The clean product was obtained as a white solid (120 mg, 100% yield), transferred to the next step without further purification.

b) The product of step (a) (125 mg, 0.33 mmol) was dissolved in dry toluene (10 mL) under N$_2$ atmosphere. To the stirring solution were added Pd(OAc)$_2$ (7.4 mg, 0.033 mmol), BINAP (22.5 mg, 0.036 mmol) and cesium carbonate (134 mg, 0.41 mmol) and the reaction mixture was stirred at rt for 20 min. 2,4-Dichloroaniline (61 mg, 0.38 mmol) was added and the mixture was stirred at rt for 10 min. Stirring was continued at 110° C. under N$_2$ atmosphere for 6 hours, cooled and allowed to proceed overnight at rt. The mixture was filtered through a small pad of silica gel on a sinter glass, eluted with additional amount of 30 mL toluene and then 50 mL EtOAc. 229 mg of yellowish crude oil obtained which was further purified using Combiflash (PE-THF) affording the clean desired product as a yellow oil (86 mg, 56.5% yield).

$^1$H NMR: (CDCl$_3$) δ 7.86 (d, 1H, CH); 7.46 (d, 1H, CH); 7.35 (d, 1H, CH); 7.30-7.07 (m, 7H, CH); 7.01 (dd, 1H, CH); 6.60 (bs, 1H, NH); 6.28 (bs, 1H, NH).

MS: m/z 460.90 (MH$^+$).

Synthesis of Compound 66

N-(1-Cyclopropyl-1-methyl-ethyl)-4-(2,4-dichloro-phenylamino)-2-trifluoromethyl-benzenesulfonamide a) To the solution of 1-cyclopropyl-1-methyl-ethylamine toluene sulfonate (286 mg. 1.05 mmol) and triethylamine (305 mg, 3.0 mmol) in 15 ml THF 4-bromo-2-tri-fluoromethylbenzenesulfonyl chloride (348 mg, 1.07 mmol) was added in one portion and reaction mixture was stirred for a day. Ethyl acetate was added and mixture was washed twice with 1 N HCl, water and brine. After drying over sodium sulfate solvent was evaporated and crude solid used in the next stage. Yield 82%.

b) Mixture of the product of step (a) (318 mg, 0.82 mmol), 2,4-dichloroaniline (183 mg, 1.12 mmol), Pd(OAc)$_2$ (25 mg, 0.11 mmol), BINAP (60 mg, 0.10 mmol) and cesium carbonate (338 mg, 1.04 mmol) in 15 ml toluene was relaxed for 6 hours. Toluene was evaporated in vacuum and crude oil was purified by Combiflash (PE-THF). Yield 62%.

NMR (CDCl$_3$) δ: 0.286-0.319 (4H, m, CH); 1.00 (1H, m, CH); 1.13 (6H, s, CH); 4.71 (1H, s, NH); 6.29 (1H, s, NH); 7.16-7.20 (1H, dd, CH); 7.24-7.27 (2H, dd, CH); 7.31-7.34 (1H, d, CH); 7.37-7.38 (1H, d, CH); 7.47-7.48 (1H, d, CH); 8.15-8.18 (1H, d, CH). Molecular ion observed [M–H]$^-$=465 consistent with the molecular formula C$_{19}$H$_{19}$Cl$_2$F$_3$N$_2$O$_2$S.

Synthesis of Compound 67

N-Benzyl-4-(2,4-dichloro-phenylamino)-2-trifluoromethyl-benzenesulfonamide a) 4-Bromo-2-trifluoromethyl-benzenesulfonyl chloride (323.5 mg, 1.0 mmol) was added in one portion to a stirred solution of benzylamine (321 mg, 3.0 mmol) in dry THF (15 mL), under N$_2$ atmosphere. After 24 h at rt, water and EtOAc were added, and the layers were separated. The organic layer was washed with 1 N HCl and saturated NaCl solutions, dried over sodium sulfate, filtered and evaporated. The clean product was obtained as a white solid (390 mg, 99% yield), transferred to the next step without further purification.

b) The product of step (a) (390 mg, 0.99 mmol) was dissolved in dry toluene (25 mL) under N$_2$ atmosphere. To the stirring solution were added Pd(OAc)$_2$ (22 mg, 0.099 mmol), BINAP (68.5 mg, 0.11 mmol) and cesium carbonate (403 mg, 1.24 mmol) and the reaction mixture was stirred at rt for 20 min. 2,4-Dichloroaniline (184 mg, 1.14 mmol) was added and the mixture was stirred at rt for 10 min. Stirring was continued at 110° C. under N$_2$ atmosphere for 6 hours, cooled and allowed to proceed overnight at rt. The mixture was filtered through a small pad of silica gel on a sinter glass, eluted with additional amount of 30 mL toluene and then 50 mL EtOAc. 524 mg of yellowish crude oil obtained which was further purified using Combiflash (PE-THF) affording the clean desired product as a yellow oil (250 mg, 53% yield).

¹H NMR: (CDCl₃) δ 8.06 (d, 1H, CH); 7.49 (d, 1H, CH); 7.48-7.19 (m, 8H, CH); 7.14 (dd, 1H, CH); 6.33 (bs, 1H, NH); 4.88 (t, 1H, NH); 4.16 (d, 2H, CH₂N).
MS: m/z 474.90 (MH⁺).

Synthesis of Compound 68

1-[4-(2,4-Dichloro-phenylamino)-2-trifluoromethyl-benzenesulfonylamino]-cyclopropanecarboxylic acid methyl ester a) To a solution of 1-aminocyclopropane-1-carboxylic acid methyl ester (100 mg. 0.86 mmol) and triethylamine (342 mg, 2.94 mmol) in 15 ml of THF 4-bromo-2-trifluoromethylbenzenesulfonyl chloride (173 mg, 0.53 mmol) was added in one portion and reaction mixture was stirred for a day. Ethyl acetate was added and mixture was washed twice with 1 N HCl, water and brine. After drying over sodium sulfate solvent was evaporated and crude solid used in the next stage. Yield 60%.

b) Mixture of the product of step (a) (120 mg, 0.36 mmol), 2,4-dichloroaniline (59 mg, 0.36 mmol), Pd(OAc)₂ (13 mg, 0.10 mmol), BINAP (30 mg, 0.05 mmol) and cesium carbonate (207 mg, 0.63 mmol) in 15 ml toluene was relaxed for 6 hours. Toluene was evaporated in vacuum and crude oil was purified by Combiflash (PE-THF). Yield 11%

NMR (CDCl₃) δ: 1.452-1.484 (4H, q, CH); 3.402 (3H, s, CH); 5.62 (1H, s, NH); 6.33 (1H, s, NH); 7.12-7.15 (1H, dd, CH); 7.280-7.287 (1H, d, CH); 7.39 (1H, s, CH); 7.386-7.394 (1H, d, CH); 7.483-7.490 (1H, d, CH); 7.99-8.02 (1H, d, CH). Molecular ion observed [M−H]⁺=483 consistent with the molecular formula C₁₈H₁₅Cl₂F₃N₂O₄S.

Synthesis of Compound 69

4-(1-Acetyl-2,3-dihydro-1H-indol-6-ylamino)-N-cyclopropylmethyl-2-trifluoromethyl-benzene-sulfonamide A mixture of 4-Bromo-N-cyclopropylmethyl-2-trifluoromethyl-benzenesulfonamide (51 mg), Pd(OAc)₂ (3.2 mg), BINAP (14 mg), cesium carbonate (55 mg) and 1-(6-Amino-2,3-dihydro-indol-1-yl)-ethanone (50 mg) in 15 ml toluene was relaxed for 12 hours. The reaction mixture was eluted through a silica bed with Toluene and then with PE:EtOAc (70:30). The toluene fraction was discarded and the solvent of the PE:EtOAc fraction was removed under reduced pressure. The crude product was purified by Combiflash (linear gradient PE-THF). Yield 32 mg, 49%.

¹H NMR (300 MHz, CDCl3, rt) δ 0.097 (m, 2H, CH₂), 0.48 (m, 2H, CH₂), 0.89 (m, 1H, CH), 2.58 (s, 3H, CH₃), 2.267 (s, 3H, C(O)CH₃), 2.82 (t, 2H, J=6.6 Hz, CH₂), 3.24 (m, 2H, CH₂), 4.14 (m, 2H, CH₂), 4.651 (s, broad, 1H, NH), 7.02 (m, broad, 3H, ArH), 7.233 (m, broad, 2H, ArH), 7.99 (d, 1H, J=9.3, ArH), and 8.23 (d, 2H, J=8.7 Hz, ArH).
MS: m/z 454.1 (M⁺)

Synthesis of Compound 70

N-Cyclopropylmethyl-4-(2-methyl-1,3-dioxo-2,3-dihydro-1H-isoindol-5-ylamino)-2-trifluoromethyl-benzenesulfonamide A mixture of 4-Bromo-N-cyclopropylmethyl-2-trifluoromethyl-benzenesulfonamide (150 mg), Pd(OAc)₂ (9.5 mg), BINAP (26 mg), cesium carbonate (164 mg) and 5-Amino-2-methyl-isoindole-1,3-dione (148 mg) in 15 ml toluene was relaxed for 12 hours. The reaction mixture was eluted through a silica bed with Toluene and then with PE:EtOAc (1:1). The toluene fraction was discarded and the solvent of the PE:EtOAc fraction was removed under reduced pressure. The crude product was purified by Combiflash (linear gradient PE-THF). Yield 83 mg, 43%.

¹H NMR (300 MHz, CDCl3, rt) δ 0.13 (m, 2H, CH₂), 0.49 (m, 2H, CH₂), 0.89 (m, 1H, CH), 2.87 (t, broad, 2H, J=7.2 Hz, CH₂), 3.18 (s, 3H, CH₃), 4.72 (t, broad, 1H, NH), 6.75 (s, broad, 1H, NH), 6.98 (s, 1H, ArH), 7.37 (dt, J=8.1, J=2.7, 1H, ArH), 7.489 (d, 1H, J=2.1, ArH), 7.579 (d, 1H, J=1.8, ArH), 7.81 (d, 1H, J=8.1, ArH), and 8.14 (d, 2H, J=8.7 Hz, ArH).
MS: m/z 454.1 (M⁺)

Synthesis of Compound 71

N-Cyclopropylmethyl-4-(2-ethyl-2H-pyrazol-3-ylamino)-2-trifluoromethyl-benzenesulfonamide a) 4-Bromo-2-trifluoromethyl-benzenesulfonyl chloride (500 mg, 1.55 mmol) was added in one portion to a stirred solution of cyclopropyl-methylamine (274 mg, 3.86 mmol) in dry THF (30 mL), under N₂ atmosphere. After 24 h at rt, water and EtOAc were added, and the layers were separated. The organic layer was washed with 1 N HCl and saturated NaCl solutions, dried over sodium sulfate, filtered and evaporated. The clean product was obtained as a yellow oil (574 mg, 100% yield), transferred to the next step without further purification.

b) The product of step (a) (150 mg, 0.42 mmol) was dissolved in dry toluene (15 mL) under N₂ atmosphere. To the stirring solution were added Pd(OAc)₂ (9.5 mg, 0.042 mmol), BINAP (29 mg, 0.046 mmol) and cesium carbonate (171 mg, 0.53 mmol) and the reaction mixture was stirred at rt for 20 min. 3-Amino-2-ethyl-pyrazole (54 mg, 0.48 mmol) was added and the mixture was stirred at rt for 10 min. Stirring was continued at 110° C. under N₂ atmosphere for 6 hours, cooled and allowed to proceed overnight at rt. The mixture was filtered through a small pad of silica gel on a sinter glass, eluted with additional amount of 30 mL toluene and then 50 mL EtOAc. 143 mg of yellowish crude oil obtained which was further purified using Combiflash (PE-THF) affording the clean desired product as a yellow oil (94 mg, 58% yield).

¹H NMR: (CDCl₃) δ 8.03 (d, 1H, CH); 7.58 (d, 1H, CH); 7.15 (d, 1H, CH); 6.83 (dd, 1H, CH); 6.15 (d, 1H, CH); 6.07 (bs, 1H, NH); 2.83 (dd, 2H, CH₂N); 4.70 (t, 1H, NH); 4.06 (q, 2H, CH₂CH₃); 1.41 (t, 3H, CH₂CH₃); 0.89 (m, 1H, CH); 0.49 (m, 2H, CH₂); 0.11 (m, 2H, CH₂).
MS: m/z 389.10 (MH⁺).

Synthesis of Compound 72

N-Cyclopropylmethyl-4-(4-dimethylamino-phenylamino)-2-trifluoromethyl-benzenesulfonamide a) 4-Bromo-2-trifluoromethyl-benzenesulfonyl chloride (500 mg, 1.55 mmol) was added in one portion to a stirred solution of cyclopropyl-methylamine (274 mg, 3.86 mmol) in dry THF (30 mL), under N₂ atmosphere. After 24 h at rt, water and EtOAc were added, and the layers were separated. The organic layer was washed with 1 N HCl and saturated NaCl solutions, dried over sodium sulfate, filtered and evaporated. The clean product was obtained as a yellow oil (574 mg, 100% yield), transferred to the next step without further purification.

b) The product of step (a) (150 mg, 0.42 mmol) was dissolved in dry toluene (15 mL) under $N_2$ atmosphere. To the stirring solution were added $Pd(OAc)_2$ (9.5 mg, 0.042 mmol), BINAP (29 mg, 0.046 mmol) and cesium carbonate (171 mg, 0.53 mmol) and the reaction mixture was stirred at rt for 20 min. N,N-Dimethyl-benzene-1,4-diamine (65 mg, 0.48 mmol) was added and the mixture was stirred at rt for 10 min. Stirring was continued at 110° C. under $N_2$ atmosphere for 6 hours, cooled and allowed to proceed overnight at rt. The mixture was filtered through a small pad of silica gel on a sinter glass, eluted with additional amount of 30 mL toluene and then 50 mL EtOAc. 199 mg of yellowish crude oil obtained which was further purified using Combiflash (PE-THF) affording the clean desired product as a yellow oil (72 mg, 41.5% yield).

$^1H$ NMR: ($CDCl_3$) δ 7.93 (d, 1H, CH); 7.13-7.07 (m, 3H, CH); 6.85 (dd, 1H, CH); 6.76-6.73 (m, 2H, CH); 6.03 (bs, 1H, NH); 4.60 (t, 1H, NH); 2.98 (s, 6H, $CH_3$); 2.79 (t, 2H, $CH_2N$); 0.87 (m, 1H, CH); 0.46 (m, 2H, $CH_2$); 0.084 (m, 2H, $CH_2$).

MS: m/z 414.10 ($MH^+$).

Synthesis of Compound 73

4-(2-Chloro-pyridin-3-ylamino)-N-cyclopropylmethyl-2-trifluoromethyl-benzenesulfonamide A mixture of 4-Bromo-N-cyclopropylmethyl-2-trifluoromethyl-benzenesulfonamide (150 mg), $Pd(OAc)_2$ (9.5 mg), BINAP (26 mg), cesium carbonate (164 mg) and 2-Chloro-pyridin-3-ylamine (108 mg) in 15 ml toluene was relaxed for 12 hours. The reaction mixture was eluted through a silica bed with Toluene and then with PE:EtOAc (1:1). The toluene fraction was discarded and the solvent of the PE:EtOAc fraction was removed under reduced pressure. The crude product was purified by Combiflash (linear gradient PE-THF). Yield 25 mg, 15%.

$^1H$ NMR (300 MHz, CDCl3, rt) δ still waiting for spectrum (22-01-07)

MS: m/z 406.0 ($M^+$)

Synthesis of Compound 74

4-(Bicyclo[2.2.1]hept-2-ylamino)-N-(1-cyclopropyl-1-methyl-ethyl)-2-trifluoromethyl-benzenesulfonamide a) 4-Bromo-2-trifluoromethyl-benzenesulfonyl chloride (1190 mg, 3.69 mmol) was added in one portion to a stirred solution of 1-Cyclopropyl-1-methyl-ethylamine, toluene-4-sulfonate (1000 mg, 3.69 mmol) in dry DCM (40 mL), under $N_2$ atmosphere. After 24 h at rt, water and EtOAc were added, and the layers were separated. The organic layer was washed with 1 N HCl and saturated NaCl solutions, dried over sodium sulfate, filtered and evaporated. The clean product was obtained as a yellow oil (1.26 gr, 88.5% yield), transferred to the next step without further purification.

b) The product of step (a) (193 mg, 0.5 mmol) was dissolved in dry toluene (12 mL) under $N_2$ atmosphere. To the stirring solution were added $Pd(OAc)_2$ (11.2 mg, 0.05 mmol), BINAP (34.2 mg, 0.055 mmol) and cesium carbonate (203 mg, 0.625 mmol) and the reaction mixture was stirred at rt for 20 min. exo-2-Aminonorbornane (111 mg, 1.0 mmol) was added and the mixture was stirred at rt for 10 min. Stirring was continued at 110° C. under $N_2$ atmosphere for 6 hours, cooled and allowed to proceed overnight at rt. The mixture was filtered through a small pad of silica gel on a sinter glass, eluted with additional amount of 30 mL toluene and then 50 mL EtOAc. 267 mg of yellowish crude oil obtained which was further purified using Combiflash (PE-THF) affording the clean desired product as a yellowish solid (170 mg, 81.6% yield).

$^1H$ NMR: ($CDCl_3$) δ 8.04 (d, 1H, CH); 6.89 (d, 1H, CH); 6.63 (dd, 1H, CH); 4.64 (bs, 1H, NH); 4.29 (d, 1H, NH); 3.30 (m, 1H, CH); 2.36 (bs, 1H, CH); 2.28 (bs, 1H, CH); 1.88 (m, 1H, CH); 1.59 (m, 3H, CH); 1.45 (m, 1H, CH); 1.25 (m, 3H, CH); 1.11 (s, 6H, $CH_3$); 0.99 (m, 1H, CH); 0.29 (m, 4H, $CH_2$).

MS: m/z 417.20 ($MH^+$).

Synthesis of Compound 75

N-(1-Cyclopropyl-1-methyl-ethyl)-4-(3,5-dimethoxy-phenylamino)-2-trifluoromethyl-benzenesulfonamide a) 4-Bromo-2-trifluoromethyl-benzenesulfonyl chloride (1.19 gr, 3.69 mmol) was added in one portion to a stirred solution of 1-Cyclopropyl-1-methyl-ethylamine, toluene-4-sulfonate (1.0 gr, 3.69 mmol) in dry DCM (40 mL), under $N_2$ atmosphere. After 24 h at rt, water and EtOAc were added, and the layers were separated. The organic layer was washed with 1 N HCl and saturated NaCl solutions, dried over sodium sulfate, filtered and evaporated. The clean product was obtained as a yellow oil (1.26 gr, 88.5% yield), transferred to the next step without further purification.

b) The product of step (a) (120 mg, 0.31 mmol) was dissolved in dry toluene (10 mL) under $N_2$ atmosphere. To the stirring solution were added $Pd(OAc)_2$ (6.9 mg, 0.031 mmol), BINAP (21 mg, 0.034 mmol) and cesium carbonate (126 mg, 0.39 mmol) and the reaction mixture was stirred at rt for 20 min. 3,5-Dimethoxyaniline (55 mg, 0.36 mmol) was added and the mixture was stirred at rt for 10 min. Stirring was continued at 110° C. under $N_2$ atmosphere for 6 hours, cooled and allowed to proceed overnight at rt. The mixture was filtered through a small pad of silica gel on a sinter glass, eluted with additional amount of 30 mL toluene and then 50 mL EtOAc. 200 mg of yellowish crude oil obtained which was further purified using Combiflash (PE-THF) affording the clean desired product as a yellowish solid (130 mg, 91.6% yield).

$^1H$ NMR: ($CDCl_3$) δ 8.09 (d, 1H, CH); 7.35 (d, 1H, CH); 7.17 (dd, 1H, CH); 6.32 (d, 2H, CH); 6.25 (t, 1H, CH); 4.69 (bs, 1H, NH); 3.79 (s, 6H, $OCH_3$); 1.12 (s, 6H, $CH_3$); 1.00 (m, 1H, CH); 0.29 (m, 4H, $CH_2$).

MS: m/z 459.20 ($MH^+$).

Synthesis of Compound 76

4-(2-Chloro-pyridin-3-ylamino)-N-(1-cyclopropyl-1-methyl-ethyl)-2-trifluoromethyl-benzenesulfonamide a) 4-Bromo-2-trifluoromethyl-benzenesulfonyl chloride (1190 mg, 3.69 mmol) was added in one portion to a stirred solution of 1-Cyclopropyl-1-methyl-ethylamine, toluene-4-sulfonate (1000 mg, 3.69 mmol) in dry DCM (40 mL), under $N_2$ atmosphere. After 24 h at rt, water and EtOAc were added, and the layers were separated. The organic layer was washed with 1 N HCl and saturated NaCl solutions, dried over sodium sulfate, filtered and evaporated. The clean product was obtained as a yellow oil (1.26 gr, 88.5% yield), transferred to the next step without further purification.

b) The product of step (a) (150 mg, 0.39 mmol) was dissolved in dry toluene (10 mL) under $N_2$ atmosphere. To the stirring solution were added Pd(OAc)$_2$ (8.7 mg, 0.039 mmol), BINAP (27 mg, 0.043 mmol) and cesium carbonate (158 mg, 0.49 mmol) and the reaction mixture was stirred at rt for 20 min. 3-Amino-2-chloro-pyridin (58 mg, 0.45 mmol) was added and the mixture was stirred at rt for 10 min. Stirring was continued at 110° C. under $N_2$ atmosphere for 6 hours, cooled and allowed to proceed overnight at rt. The mixture was filtered through a small pad of silica gel on a sinter glass, eluted with additional amount of 30 mL toluene and then 50 mL EtOAc. 185 mg of yellowish crude oil obtained which was further purified using Combiflash (PE-THF) affording the clean desired product as a yellowish oil (156 mg, 92% yield).

$^1$H NMR: (CDCl$_3$) δ 8.21 (d, 1H, CH); 8.12 (dd, 1H, CH); 7.84 (dd, 1H, CH); 7.71 (dd, 1H, CH); 7.45 (d, 1H, CH); 7.27 (dd, 1H, CH); 6.47 (bs, 1H, NH); 4.75 (bs, 1H, NH); 1.14 (s, 6H, CH$_3$); 1.01 (m, 1H, CH); 0.29 (m, 4H, CH$_2$).

MS: m/z 434.10 (MH$^+$).

Synthesis of Compound 77

N-Cyclopropylmethoxy-4-(2,4-dichloro-phenylamino)-2-trifluoromethyl-benzenesulfonamide a) To the solution of O-cyclopropylmethyl hydroxylamine hydrochloride (486 mg. 3.99 mmol) and triethylamine (506 mg, 5.0 mmol) in 15 ml THF 4-bromo-2-tri-fluoromethylbenzenesulfonyl chloride (644 mg, 1.99 mmol) was added in one portion and reaction mixture was stirred for a day. Ethyl acetate was added and mixture was washed twice with 1 N HCl, water and brine. After drying over sodium sulfate solvent was evaporated and crude solid used in the next stage. Yield 63%.

b) Mixture of the product of step (a) (282 mg, 0.75 mmol), 2,4-dichloroaniline (167 mg, 1.03 mmol), Pd(OAc)$_2$ (21 mg, 0.10 mmol), BINAP (67 mg, 0.10 mmol) and cesium carbonate (348 mg, 1.04 mmol) in 15 ml toluene was relaxed for 6 hours. Toluene was evaporated in vacuum and crude oil was purified by Combiflash (PE-THF). Yield 32%.

NMR (CDCl$_3$) δ: 0.1950.289 (2H, m, CH); 0.511-0.573 (2H, m, CH); 1.01-1.06 (1H, m, CH); 3.83-3.85 (2H, d, CH); 5.36 (1H, s, NH); 6.64 (1H, s, NH); 7.18-7.22 (1H, dd, CH); 7.29-7.39 (3H, m, CH); 7.48-7.49 (1H, d, CH); 8.10-8.13 (1H, d, CH). Molecular ion observed [M–H]$^-$=453 consistent with the molecular formula C$_{17}$H$_{15}$Cl$_2$F$_3$N$_2$O$_3$S.

Synthesis of Compound 78

3-Chloro-4-[4-(cyclopropylmethyl-sulfamoyl)-3-trifluoromethyl-phenylamino]-benzoic acid ethyl ester a) 4-Bromo-2-trifluoromethyl-benzenesulfonyl chloride (2000 mg, 6.18 mmol) was added in one portion to a stirred solution of cyclopropyl-methylamine (1100 mg, 15.5 mmol) in dry THF (60 mL), under $N_2$ atmosphere. After 24 h at rt, water and EtOAc were added, and the layers were separated. The organic layer was washed with 1 N HCl and saturated NaCl solutions, dried over sodium sulfate, filtered and evaporated. The clean product was obtained as a yellow oil (2.22 gr, 100% yield), transferred to the next step without further purification.

b) The product of step (a) (406 mg, 1.13 mmol) was dissolved in dry toluene (30 mL) under $N_2$ atmosphere. To the stirring solution were added Pd(OAc)$_2$ (25 mg, 0.113 mmol), BINAP (77 mg, 0.124 mmol) and cesium carbonate (459 mg, 1.41 mmol) and the reaction mixture was stirred at rt for 20 min. Ethyl 4-amino-3-chloro-benzoate (260 mg, 1.30 mmol) was added and the mixture was stirred at rt for 10 min. Stirring was continued at 110° C. under $N_2$ atmosphere for 6 hours, cooled and allowed to proceed overnight at rt. The mixture was filtered through a small pad of silica gel on a sinter glass, eluted with additional amount of 30 mL toluene and then 50 mL EtOAc. 240 mg of yellowish crude oil obtained which was further purified using Combiflash (PE-THF) affording the clean desired product as a yellowish oil (156 mg, 34.4% yield).

MS: m/z 477.00 (MH$^+$.

Synthesis of Compound 79

3-Chloro-4-[4-(cyclopropylmethyl-sulfamoyl)-3-trifluoromethyl-phenylamino]-benzoic acid a) N-bromo-N-cyclopropylmethyl-2-trifluoromethyl-benzenesulfonamide (406 mg, 1.13 mmol) was dissolved in dry toluene (30 mL) under $N_2$ atmosphere. To the stirring solution were added Pd(OAc)$_2$ (25 mg, 0.113 mmol), BINAP (77 mg, 0.124 mmol) and cesium carbonate (459 mg, 1.41 mmol) and the reaction mixture was stirred at rt for 20 min. Ethyl 4-amino-3-chloro-benzoate (260 mg, 1.30 mmol) was added and the mixture was stirred at rt for 10 min. Stirring was continued at 110° C. under $N_2$ atmosphere for 6 hours, cooled and allowed to proceed overnight at rt. The mixture was filtered through a small pad of silica gel on a sinter glass, eluted with additional amount of 30 mL toluene and then 50 mL EtOAc. 240 mg of yellowish crude oil obtained which was further purified using Combiflash (PE-THF) affording the clean desired product as a yellowish oil (156 mg, 34.4% yield).

b) The product of step (a) (180 mg, 0.39 mmol) was dissolved in MeOH (30 mL). Saturated NaHCO$_3$ solution (10 mL) was added and the suspension was stirred at 80° C. for 6 h. The mixture was cooled to rt and stirring was continued overnight. EtOAc was added, and the mixture was washed with 1N HCl and saturated NaCl solutions. The organic layer was evaporated to afford the crude product (212 mg), which was purified by Combiflash to give the clean desired acid as a white solid (22 mg, 12.5% yield).

$^1$H NMR: (CDCl$_3$) δ 8.98 (s, 1H, CO$_2$H); 7.98 (s, 1H, CH); 7.92 (d, 1H, CH); 7.83 (m, 1H, CH); 7.58 (d, 1H, CH); 7.50 (d, 1H, CH); 7.37 (d, 1H, CH); 2.75 (t, 2H, CH$_2$N); 0.83 (m, 1H, CH); 0.36 (m, 2H, CH$_2$); 0.11 (m, 2H, CH$_2$).

MS: m/z 449.00 (MH$^+$).

Synthesis of Compound 80

4-(1-Aza-bicyclo[2.2.2]oct-3-ylamino)-N-cyclopropylmethyl-2-trifluoromethyl-benzenesulfonamide a) 4-Bromo-2-trifluoromethyl-benzenesulfonyl chloride (500 mg, 1.55 mmol) was added in one portion to a stirred solution of cyclopropyl-methylamine (274 mg, 3.86 mmol) in dry THF (30 mL), under N₂ atmosphere. After 24 h at rt, water and EtOAc were added, and the layers were separated. The organic layer was washed with 1 N HCl and saturated NaCl solutions, dried over sodium sulfate, filtered and evaporated. The clean product was obtained as a white solid (574 mg, 100% yield), transferred to the next step without further purification.

b) The product of step (a) (179 mg, 0.5 mmol) was dissolved in dry toluene (12 mL) under N₂ atmosphere. To the stirring solution were added Pd(OAc)₂ (22.4 mg, 0.1 mmol), BINAP (68.4 mg, 0.11 mmol) and cesium carbonate (796 mg, 2.45 mmol) and the reaction mixture was stirred at rt for 20 min. 3-Aminoquinuclidine (126 mg, 1.0 mmol) was added and the mixture was stirred at rt for 10 min. Stirring was continued at 110° C. under N₂ atmosphere for 6 hours, cooled and allowed to proceed overnight at rt. The mixture was filtered through a small pad of silica gel on a sinter glass, eluted with additional amount of 30 mL toluene and then 50 mL EtOAc. 105 mg of yellowish crude oil obtained which was further purified using Combiflash (PE-THF) affording the clean desired product as a yellowish solid (65 mg, 32% yield).

$^1$H NMR: (CDCl₃) δ 7.80 (d, 1H, CH); 7.10 (d, 1H, CH); 6.86 (dd, 1H, CH); 5.88 (d, 1H, NH); 3.92 (bs, 1H, NH); 3.66 (m, 1H, CH); 2.86 (m, 2H, CH); 2.69 (t, 2H, CH₂N); 2.58 (m, 1H, CH); 2.12-1.89 (m, 5H, CH); 1.41-0.99 (m, 3H, CH); 0.82 (m, 1H, CH); 0.35 (m, 2H, CH₂); 0.044 (m, 2H, CH₂).

MS: m/z 404.10 (MH⁺).

Synthesis of Compound 81

3-Chloro-4-[4-(1-cyclopropyl-1-methyl-ethylsulfamoyl)-3-trifluoromethyl-phenylamino]-benzoic acid ethyl ester a) 4-Bromo-2-trifluoromethyl-benzenesulfonyl chloride (1190 mg, 3.69 mmol) was added in one portion to a stirred solution of 1-Cyclopropyl-1-methyl-ethylamine, toluene-4-sulfonate (1000 mg, 3.69 mmol) in dry DCM (40 mL), under N₂ atmosphere. After 24 h at rt, water and EtOAc were added, and the layers were separated. The organic layer was washed with 1 N HCl and saturated NaCl solutions, dried over sodium sulfate, filtered and evaporated. The clean product was obtained as a yellow oil (1.26 gr, 88.5% yield), transferred to the next step without further purification.

b) The product of step (a) (573 mg, 1.49 mmol) was dissolved in dry toluene (40 mL) under N₂ atmosphere. To the stirring solution were added Pd(OAc)₂ (33 mg, 0.149 mmol), BINAP (102 mg, 0.164 mmol) and cesium carbonate (605 mg, 1.86 mmol) and the reaction mixture was stirred at rt for 20 min. Ethyl 4-amino-3-chloro-benzoate (341 mg, 1.71 mmol) was added and the mixture was stirred at rt for 10 min. Stirring was continued at 110° C. under N₂ atmosphere for 6 hours, cooled and allowed to proceed overnight at rt. The mixture was filtered through a small pad of silica gel on a sinter glass, eluted with additional amount of 30 mL toluene and then 50 mL EtOAc. 480 mg of yellowish crude oil obtained which was further purified using Combiflash (PE-THF) affording the clean desired product as a yellowish solid (340 mg, 45% yield).

MS: m/z 503.00 (MH⁻).

Synthesis of Compound 82

3-Chloro-4-[4-(1-cyclopropyl-1-methyl-ethylsulfamoyl)-3-trifluoromethyl-phenylamino]-benzoic acid a) 4-Bromo-N-(1-cyclopropyl-1-methyl-ethyl)-2-trifluoromethyl-benzenesulfonamide (573 mg, 1.49 mmol) was dissolved in dry toluene (40 mL) under N₂ atmosphere. To the stirring solution were added Pd(OAc)₂ (33 mg, 0.149 mmol), BINAP (102 mg, 0.164 mmol) and cesium carbonate (605 mg, 1.86 mmol) and the reaction mixture was stirred at rt for 20 min. Ethyl 4-amino-3-chloro-benzoate (341 mg, 1.71 mmol) was added and the mixture was stirred at rt for 10 min. Stirring was continued at 110° C. under N₂ atmosphere for 6 hours, cooled and allowed to proceed overnight at rt. The mixture was filtered through a small pad of silica gel on a sinter glass, eluted with additional amount of 30 mL toluene and then 50 mL EtOAc. 480 mg of yellowish crude oil obtained which was further purified using Combiflash (PE-THF) affording the clean desired product as a yellowish oil (340 mg, 45% yield).

b) The product of step (a) (340 mg, 0.69 mmol) was dissolved in MeOH/H₂O (50 mL). Saturated NaHCO₃ solution (15 mL) was added and the suspension was stirred at 80° C. for 6 h. The mixture was cooled to rt and stirring was continued overnight. EtOAc was added, and the mixture was washed with 1N HCl and saturated NaCl solutions. The organic layer was evaporated to afford the crude product (230 mg), which was purified by Combiflash to give the clean desired acid as a white solid (115 mg, 35% yield).

$^1$H NMR: (CDCl₃) δ 8.98 (s, 1H, CO₂H); 8.06 (d, 1H, CH); 7.99 (d, 1H, CH); 7.86 (dd, 1H, CH); 7.60 (d, 1H, CH); 7.52 (d, 1H, CH); 7.48 (s, 1H, NH); 7.42 (dd, 1H, CH); 1.05 (s, 6H, CH₃); 1.02 (m, 1H, CH); 0.26 (m, 2H, CH₂); 0.17 (m, 2H, CH₂).

MS: m/z 475.00 (MH⁻).

Synthesis of Compound 83

{[4-(Bicyclo[2.2.1]hept-2-ylamino)-2-trifluoromethyl-benzenesulfonyl]-cyclopropylmethyl-amino}-acetic acid tert-butyl ester a) 4-bromo-N-cyclopropylmethyl-2-trifluoromethyl-benzenesulfonamide (2.07 gr, 5.78 mmol) was dissolved in dry toluene (60 mL) under N₂ atmosphere. To the stirring solution were added Pd(OAc)₂ (129.5 mg, 0.58 mmol), BINAP (396 mg, 0.64 mmol) and cesium carbonate (2.35 gr, 7.23 mmol) and the reaction mixture was stirred at rt for 20 min. exo-2-Aminonorbornane (1.28 gr, 11.56 mmol) was added and the mixture was stirred at rt for 10 min. Stirring was continued at 110° C. under N₂ atmosphere for 6 hours, cooled and allowed to proceed overnight at rt. The mixture was filtered through a small pad of silica gel on a sinter glass, eluted with additional amount of 150 mL toluene and then 250 mL EtOAc. 2.12 gr of yellowish crude oil obtained which was further purified using Combiflash (PE-THF) affording the clean desired product as a yellowish solid (1.39 gr, 62% yield).

b) The product of step (a) (194 mg, 0.50 mmol) was dissolved in DCM/H$_2$O (50/2 mL). NaOH (1.0 gr) was added and the mixture was stirred at rt for 20 min. Bromo-acetic acid tert-butyl ester (97.5 mg, 0.50 mmol) was added dropwise over 10 min followed by addition of Bu$_4$N$^+$HSO$_4^-$ (85 mg, 0.25 mmol) and the suspension was stirred at rt for 1 h. The mixture was diluted with DCM (30 mL) and water (60 mL). The layers were separated and the aqueous phase was further extracted with DCM (2×60 mL). The combined organic layers were washed with 1M HCl and sat. NaCl solutions, dried over Na$_2$SO$_4$ and filtered. After evaporation of the solvent, the oil obtained was purified by Combiflash to give the clean desired product as a yellow oil (245 mg, 97.5% yield).

$^1$H NMR: (CDCl$_3$) δ 8.01 (d, 1H, CH); 6.91 (bs, 1H, CH); 6.65 (bd, 1H, CH); 4.17 (s, 2H, CH$_2$N); 3.28 (dd, 1H, CH); 3.16 (d, 2H, CH$_2$N); 2.34 (bs, 1H, CH); 2.27 (bs, 1H, CH); 1.87 (m, 1H, CH); 1.57 (m, 3H, CH); 1.43 (m, 1H, CH); 1.40 (s, 9H, tBu); 1.28-1.18 (m, 3H, CH); 0.86 (m, 1H, CH); 0.50 (m, 2H, CH$_2$); 0.08 (m, 2H, CH$_2$).

MS: m/z 503.20 (MH$^+$).

Synthesis of Compound 84

{[4-(Bicyclo[2.2.1]hept-2-ylamino)-2-trifluoromethyl-benzenesulfonyl]-cyclopropylmethyl-amino}-acetic acid a) 4-(Bicyclo[2.2.1]hept-2-ylamino)-N-cyclopropylmethyl-2-trifluoromethyl-benzenesulfonamide (194 mg, 0.50 mmol) was dissolved in DCM/H$_2$O (50/2 mL). NaOH (1.0 gr) was added and the mixture was stirred at rt for 20 min. Bromo-acetic acid tert-butyl ester (97.5 mg, 0.50 mmol) was added dropwise over 10 min followed addition of Bu$_4$N+HSO$_4$— (85 mg, 0.25 mmol) and the suspension was stirred at rt for 1 h. The mixture was diluted with DCM (30 mL) and water (60 mL). The layers were separated and the aqueous phase was further extracted with DCM (2×60 mL). The combined organic layers were washed with 1M HCl and sat. NaCl solutions, dried over Na$_2$SO$_4$ and filtered. After evaporation of the solvent, the oil obtained was purified by Combiflash to give the clean desired product as a yellow oil (245 mg, 97.5% yield).

b) The product of step (a) (160 mg, 0.32 mmol) was dissolved in TFA/DCM (5%/95%, 20 mL). The solution was stirred at rt overnight. The solvent was evaporated and the residue (170 mg) was purified by chromatography (CH$_3$CN:H$_2$O, 9:1) to give the clean desired acid as a white solid (68 mg, 48% yield).

$^1$H NMR: (CDCl$_3$) δ 7.86 (d, 1H, CH); 7.01 (bs, 1H, CO$_2$H); 6.93 (d, 1H, CH); 6.71 (dd, 1H, CH); 4.06 (s, 2H, CH$_2$N); 3.23 (m, 1H, CH); 3.09 (d, 2H, CH$_2$N); 2.26 (bs, 1H, CH); 2.16 (bs, 1H, CH); 1.75 (m, 1H, CH); 1.47 (m, 3H, CH); 1.36-1.10 (m, 4H, CH); 0.83 (m, 1H, CH); 0.40 (m, 2H, CH$_2$); 0.05 (m, 2H, CH$_2$).

MS: m/z 447.10 (MH$^+$).

Synthesis of Compound 85

4-(Bicyclo[2.2.1]hept-2-ylamino)-N-cyclopropylmethoxy-2-trifluoromethyl-benzenesulfonamide a) To the solution of O-cyclopropylmethyl hydroxylamine hydrochloride (506 mg. 4.11 mmol) and triethylamine (506 mg, 5.0 mmol) in 15 ml THF 4-bromo-2-tri-fluoromethylbenzenesulfonyl chloride (895 mg, 2.77 mmol) was added in one portion and reaction mixture was stirred for a day. Ethyl acetate was added and mixture was washed twice with 1 N HCl, water and brine. After drying over sodium sulfate solvent was evaporated and crude solid used in the next stage. Yield 47%.

b) Mixture of the product of step (a) (144 mg, 0.38 mmol), 2-aminonorbornane (167 mg, 1.03 mmol), Pd(OAc)$_2$ (22 mg, 0.10 mmol), BINAP (59 mg, 0.10 mmol) and cesium carbonate (274 mg, 0.84 mmol) in 15 ml toluene was relaxed for 6 hours. Toluene was evaporated in vacuum and crude oil was purified by Combiflash (PE-THF). Yield 44%.

NMR (CDCl$_3$) δ: 0.19-0.28 (2H, m, CH); 0.52-0.56 (2H, m, CH); 0.89-0.91(1H, m, CH); 1.13-1.28(4H, m, CH); 1.85-1.92(2H, m, CH); 2.31-2.40(2H, m, CH); 3.29-3.31(1H, m, CH); 3.35 (1H, s, NH); 3.81-3.85 (2H, dd, CH); 6.64 (1H, s, NH); 6.91-6.96 (1H, dd, CH); 7.164 (1H, s, CH); 9.98-8.05 (1H, m, CH). Molecular ion observed [M–H]$^-$=405 consistent with the molecular formula C$_{18}$H$_{23}$F$_3$N$_2$O$_3$S.

Synthesis of Compound 86

N-Acetyl-4-(bicyclo[2.2.1]hept-2-ylamino)-N-cyclopropylmethyl-2-trifluoromethyl-benzenesulfonamide a) 4-Bromo-N-cyclopropylmethyl-2-trifluoromethyl-benzenesulfonamide (2.07 gr, 5.78 mmol) was dissolved in dry toluene (60 mL) under N$_2$ atmosphere. To the stirring solution were added Pd(OAc)$_2$ (129.5 mg, 0.58 mmol), BINAP (396 mg, 0.64 mmol) and cesium carbonate (2.35 gr, 7.23 mmol) and the reaction mixture was stirred at rt for 20 min. exo-2-Aminonorbornane (1.28 gr, 11.56 mmol) was added and the mixture was stirred at rt for 10 min. Stirring was continued at 110° C. under N$_2$ atmosphere for 6 hours, cooled and allowed to proceed overnight at rt. The mixture was filtered through a small pad of silica gel on a sinter glass, eluted with additional amount of 150 mL toluene and then 250 mL EtOAc. 2.12 gr of yellowish crude oil obtained which was further purified using Combiflash (PE-THF) affording the clean desired product as a yellowish solid (1.39 gr, 62% yield).

b) The product of step (a) (100 mg, 0.26 mmol) was dissolved in dry THF (10 mL). NaOtBu (30 mg, 0.31 mmol) and Et$_3$N (79 mg, 0.78 mmol) were added and the mixture was stirred at rt for 20 min. A solution of Acetyl chloride, in dry THF (2 mL), was added slowly and the reaction mixture was stirred at rt for 5 h. Water and EtOAc were added and the layers separated. Evaporation of the solvent afforded the crude oil (132 mg), which was purified by Combiflash to give the clean product as a white solid (105 mg, 94% yield).

$^1$H NMR: (CDCl$_3$) δ 8.06 (d, 1H, CH); 6.89 (d, 1H, CH); 6.68 (dd, 1H, CH); 3.72 (d, 2H, CH$_2$N); 3.31 (dd, 1H, CH); 2.37 (bs, 1H, CH); 2.29 (bs, 1H, CH); 2.29 (s, 3H, CH$_3$); 1.90 (m, 1H, CH); 1.59 (m, 3H, CH); 1.45 (m, 1H, CH); 1.33-1.12 (m, 4H, CH); 0.57 (m, 2H, CH$_2$); 0.43 (m, 2H, CH$_2$).

MS: m/z 431.10 (MH$^+$).

Synthesis of Compound 87

4-Cycloheptylamino-N-cyclopropylmethyl-2-trifluoromethyl-benzenesulfonamide a) 4-Bromo-2-trifluoromethyl-benzenesulfonyl chloride (2.0 gr, 6.18 mmol) was added in one portion to a stirred solution of cyclopropyl-methylamine (1.1 gr, 15.5 mmol) in dry THF (60 mL), under $N_2$ atmosphere. After 24 h at rt, water and EtOAc were added, and the layers were separated. The organic layer was washed with 1 N HCl and saturated NaCl solutions, dried over sodium sulfate, filtered and evaporated. The clean product was obtained as a yellowish solid (2.21 gr, 100% yield), transferred to the next step without further purification.

b) The product of step (a) (120 mg, 0.34 mmol) was dissolved in dry toluene (10 mL) under $N_2$ atmosphere. To the stirring solution were added $Pd(OAc)_2$ (7.6 mg, 0.034 mmol), BINAP (23 mg, 0.037 mmol) and cesium carbonate (138 mg, 0.43 mmol) and the reaction mixture was stirred at rt for 20 min. Cycloheptylamine (57 mg, 0.50 mmol) was added and the mixture was stirred at rt for 10 min. Stirring was continued at 110° C. under $N_2$ atmosphere for 6 hours, cooled and allowed to proceed overnight at rt. The mixture was filtered through a small pad of silica gel on a sinter glass, eluted with additional amount of 30 mL toluene and then 50 mL EtOAc. 162 mg of yellowish crude oil obtained which was further purified using Combiflash (PE-THF) affording the clean desired product as a yellow oil (76 mg, 57% yield).

$^1$H NMR: ($CDCl_3$) δ 7.95 (d, 1H, CH); 6.90 (d, 1H, CH); 6.61 (dd, 1H, CH); 4.60 (t, 1H, NH); 3.52 (septet, 1H, CH); 2.78 (t, 2H, $CH_2N$); 2.00 (m, 2H, $CH_2$); 1.74-1.49 (m, 10H, $CH_2$); 0.87 (m, 1H, CH); 0.46 (m, 2H, $CH_2$); 0.08 (m, 2H, $CH_2$).

MS: m/z 391.10 ($MH^+$).

Synthesis of Compound 88

4-Cyclooctylamino-N-cyclopropylmethyl-2-trifluoromethyl-benzenesulfonamide a) 4-Bromo-2-trifluoromethyl-benzenesulfonyl chloride (2.0 gr, 6.18 mmol) was added in one portion to a stirred solution of cyclopropyl-methylamine (1.1 gr, 15.5 mmol) in dry THF (60 mL), under $N_2$ atmosphere. After 24 h at rt, water and EtOAc were added, and the layers were separated. The organic layer was washed with 1 N HCl and saturated NaCl solutions, dried over sodium sulfate, filtered and evaporated. The clean product was obtained as a yellowish solid (2.21 gr, 100% yield), transferred to the next step without further purification.

b) The product of step (a) (120 mg, 0.34 mmol) was dissolved in dry toluene (10 mL) under $N_2$ atmosphere. To the stirring solution were added $Pd(OAc)_2$ (7.6 mg, 0.034 mmol), BINAP (23 mg, 0.037 mmol) and cesium carbonate (138 mg, 0.43 mmol) and the reaction mixture was stirred at rt for 20 min. Cyclooctylamine (65 mg, 0.50 mmol) was added and the mixture was stirred at rt for 10 min. Stirring was continued at 110° C. under $N_2$ atmosphere for 6 hours, cooled and allowed to proceed overnight at rt. The mixture was filtered through a small pad of silica gel on a sinter glass, eluted with additional amount of 30 mL toluene and then 50 mL EtOAc. 178 mg of yellowish crude oil obtained which was further purified using Combiflash (PE-THF) affording the clean desired product as a yellow oil (70 mg, 51% yield).

$^1$H NMR: ($CDCl_3$) δ 7.98 (d, 1H, CH); 6.97 (bs, 1H, CH); 6.69 (bd, 1H, CH); 4.64 (bs, 1H, NH); 3.57 (sextet, 1H, CH); 2.80 (t, 2H, $CH_2N$); 1.97-1.47 (m, 14H, $CH_2$); 0.89 (m, 1H, CH); 0.48 (m, 2H, $CH_2$); 0.10 (m, 2H, $CH_2$).

MS: m/z 405.10 ($MH^+$).

Synthesis of Compound 89

4-(4-tert-Butyl-cyclohexylamino)-N-cyclopropylmethyl-2-trifluoromethyl-benzenesulfonamide a) 4-Bromo-2-trifluoromethyl-benzenesulfonyl chloride (2.0 gr, 6.18 mmol) was added in one portion to a stirred solution of cyclopropyl-methylamine (1.1 gr, 15.5 mmol) in dry THF (60 mL), under $N_2$ atmosphere. After 24 h at rt, water and EtOAc were added, and the layers were separated. The organic layer was washed with 1 N HCl and saturated NaCl solutions, dried over sodium sulfate, filtered and evaporated. The clean product was obtained as a yellowish solid (2.21 gr, 100% yield), transferred to the next step without further purification.

b) The product of step (a) (120 mg, 0.33 mmol) was dissolved in dry toluene (12 mL) under $N_2$ atmosphere. To the stirring solution were added $Pd(OAc)_2$ (7.4 mg, 0.033 mmol), BINAP (23 mg, 0.036 mmol) and cesium carbonate (134 mg, 0.41 mmol) and the reaction mixture was stirred at rt for 20 min. 4-tert-Butyl-cyclohexylamine (78 mg, 0.50 mmol) was added and the mixture was stirred at rt for 10 min. Stirring was continued at 110° C. under $N_2$ atmosphere for 6 hours, cooled and allowed to proceed overnight at rt. The mixture was filtered through a small pad of silica gel on a sinter glass, eluted with additional amount of 30 mL toluene and then 50 mL EtOAc. 164 mg of yellowish crude oil obtained which was further purified using Combiflash (PE-THF) affording the clean desired product as a yellow oil (90 mg, 63% yield).

$^1$H NMR: ($CDCl_3$) δ 7.94 (d, 1H, CH); 6.91 (d, 1H, CH); 6.65 (dd, 1H, CH); 4.59 (t, 1H, NH); 3.24 (septet, 1H, CH); 2.78 (t, 2H, $CH_2N$); 2.15 (m, 1H, CH); 1.87 (m, 2H, $CH_2$); 1.28-1.01 (m, 6H, $CH_2$); 0.88 (s, 9H, tBu); 0.86 (m, 1H, CH); 0.46 (m, 2H, $CH_2$); 0.08 (m, 2H, $CH_2$).

MS: m/z 433.20 ($MH^+$).

Synthesis of Compound 90

N-Cyclopropylmethyl-4-(4-methyl-cyclohexylamino)-2-trifluoromethyl-benzenesulfonamide a) 4-Bromo-2-trifluoromethyl-benzenesulfonyl chloride (2.0 gr, 6.18 mmol) was added in one portion to a stirred solution of cyclopropyl-methylamine (1.1 gr, 15.5 mmol) in dry THF (60 mL), under $N_2$ atmosphere. After 24 h at rt, water and EtOAc were added, and the layers were separated. The organic layer was washed with 1 N HCl and saturated NaCl solutions, dried over sodium sulfate, filtered and evaporated. The clean product was obtained as a yellowish solid (2.21 gr, 100% yield), transferred to the next step without further purification.

b) The product of step (a) (120 mg, 0.33 mmol) was dissolved in dry toluene (12 mL) under $N_2$ atmosphere. To the stirring solution were added $Pd(OAc)_2$ (7.4 mg, 0.033 mmol), BINAP (23 mg, 0.036 mmol) and cesium carbonate (134 mg, 0.41 mmol) and the reaction mixture was stirred at rt for 20 min. 4-Methyl-cyclohexylamine (57 mg, 0.50 mmol) was added and the mixture was stirred at rt for 10 min. Stirring was continued at 110° C.

under N₂ atmosphere for 6 hours, cooled and allowed to proceed overnight at rt. The mixture was filtered through a small pad of silica gel on a sinter glass, eluted with additional amount of 30 mL toluene and then 50 mL EtOAc. 147 mg of yellowish crude oil obtained which was further purified using Combiflash (PE-THF) affording the clean desired product as a yellow oil (81 mg, 63% yield).

$^1$H NMR: (CDCl$_3$) δ 7.94 (d, 1H, CH); 6.95 (dd, 1H, CH); 6.66 (d, 1H, CH); 4.59 (t, 1H, NH); 3.26 (m, 1H, CH); 2.78 (t, 2H, CH$_2$N); 2.07 (m, 1H, CH); 1.81-1.59 (m, 4H, CH$_2$); 1.28-1.01 (m, 4H, CH$_2$); 0.94 (m, 3H, CH$_3$); 0.87 (m, 1H, CH); 0.46 (m, 2H, CH$_2$); 0.08 (m, 2H, CH$_2$).

MS: m/z 391.20 (MH$^+$).

Synthesis of Compound 91

N-Cyclopropylmethyl-4-hexylamino-2-trifluoromethyl-benzenesulfonamide a) 4-Bromo-2-trifluoromethyl-benzenesulfonyl chloride (2.0 gr, 6.18 mmol) was added in one portion to a stirred solution of cyclopropyl-methylamine (1.1 gr, 15.5 mmol) in dry THF (60 mL), under N₂ atmosphere. After 24 h at rt, water and EtOAc were added, and the layers were separated. The organic layer was washed with 1 N HCl and saturated NaCl solutions, dried over sodium sulfate, filtered and evaporated. The clean product was obtained as a yellowish solid (2.21 gr, 100% yield), transferred to the next step without further purification.

b) The product of step (a) (120 mg, 0.33 mmol) was dissolved in dry toluene (12 mL) under N₂ atmosphere. To the stirring solution were added Pd(OAc)₂ (7.4 mg, 0.033 mmol), BINAP (23 mg, 0.036 mmol) and cesium carbonate (134 mg, 0.41 mmol) and the reaction mixture was stirred at rt for 20 min. Hexylamine (51 mg, 0.50 mmol) was added and the mixture was stirred at rt for 10 min. Stirring was continued at 110° C. under N₂ atmosphere for 6 hours, cooled and allowed to proceed overnight at rt. The mixture was filtered through a small pad of silica gel on a sinter glass, eluted with additional amount of 30 mL toluene and then 50 mL EtOAc. 151 mg of yellowish crude oil obtained which was further purified using Combiflash (PE-THF) affording the clean desired product as a yellow oil (68 mg, 54.5% yield).

$^1$H NMR: (CDCl$_3$) δ 7.96 (d, 1H, CH); 6.93 (d, 1H, CH); 6.65 (dd, 1H, CH); 4.59 (t, 1H, NH); 4.37 (t, 1H, NH); 3.18 (q, 2H, CH$_2$N); 2.78 (t, 2H, CH$_2$N); 1.65 (m, 2H, CH$_2$); 1.42-1.26 (m, 6H, CH$_2$); 0.91 (t, 3H, CH$_3$); 0.89 (m, 1H, CH); 0.45 (m, 2H, CH$_2$); 0.06 (m, 2H, CH$_2$).

MS: m/z 379.10 (MH$^+$).

Synthesis of Compound 92

4-Cyclohexylamino-N-cyclopropylmethyl-2-trifluoromethyl-benzenesulfonamide a) 4-Bromo-2-trifluoromethyl-benzenesulfonyl chloride (2.0 gr, 6.18 mmol) was added in one portion to a stirred solution of cyclopropyl-methylamine (1.1 gr, 15.5 mmol) in dry THF (60 mL), under N₂ atmosphere. After 24 h at rt, water and EtOAc were added, and the layers were separated. The organic layer was washed with 1 N HCl and saturated NaCl solutions, dried over sodium sulfate, filtered and evaporated. The clean product was obtained as a yellowish solid (2.21 gr, 100% yield), transferred to the next step without further purification.

b) The product of step (a) (120 mg, 0.33 mmol) was dissolved in dry toluene (12 mL) under N₂ atmosphere. To the stirring solution were added Pd(OAc)₂ (7.4 mg, 0.033 mmol), BINAP (23 mg, 0.036 mmol) and cesium carbonate (134 mg, 0.41 mmol) and the reaction mixture was stirred at rt for 20 min. Cyclohexylamine (50 mg, 0.50 mmol) was added and the mixture was stirred at rt for 10 min. Stirring was continued at 110° C. under N₂ atmosphere for 6 hours, cooled and allowed to proceed overnight at rt. The mixture was filtered through a small pad of silica gel on a sinter glass, eluted with additional amount of 30 mL toluene and then 50 mL EtOAc. 143 mg of yellowish crude oil obtained which was further purified using Combiflash (PE-THF) affording the clean desired product as a yellow oil (62 mg, 50% yield).

MS: m/z 377.10 (MH$^+$).

Synthesis of Compound 93

N-Cyclopropylmethyl-4-[(tetrahydro-pyran-4-ylmethyl)-amino]-2-trifluoromethyl-benzenesulfonamide Mixture of 4-bromo-N-cyclopropylmethyl-2-trifluoromethylsulfonamide (138 mg, 0.38 mmol), tetrahydropyran-4-yl methylamine (88 mg, 0.76 mmol), Pd(OAc)₂ (25 mg, 0.1 mmol), BINAP (60 mg, 0.1 mmol) and cesium carbonate (274 mg, 0.84 mmol) in 15 ml toluene was reflaxed for 8 hours. Toluene was evaporated in vacuum and crude oil was purified by Combiflash (PE-THF). Yield 42%

NMR (CDCl$_3$) δ: 0.03-0.1 (2H, q, CH); 0.43-0.49 (2H, q, CH); 0.43-0.49 (2H, q, CH); 0.83-0.89(1H, m, CH); 1.32-1.46 (2H, m, CH); 1.67-1.72 (2H, m, CH); 1.92-1.90 (1H, m, CH); 2.76-2.80(2H, t, CH); 3.093-3.135 (2H, t, CH); 3.36-3.40 (2H, m, CH); 3.99-4.04(2H, m, CH); 4.45 (1H, m, NH); 4.57-4.61 (1H, t, NH); 6.65-6.69 (1H, m, CH); 6.93-6.98 (1H, d, CH); 7.96-7.99(1H, d, CH). Molecular ion observed [M−H]$^+$=393 consistent with the molecular formula C$_{17}$H$_{23}$F$_3$N$_2$O$_3$S.

Synthesis of Compound 94

N-Cyclopropylmethyl-4-(piperidin-1-ylamino)-2-trifluoromethyl-benzenesulfonamide Mixture of 4-bromo-N-cyclopropylmethyl-2-trifluoromethylsulfonamide (184 mg, 0.51 mmol), 1-aminopiperidine (108 mg, 1.08 mmol), Pd(OAc)₂ (24 mg, 0.1 mmol), BINAP (63 mg, 0.1 mmol) and cesium carbonate (350 mg, 1.07 mmol) in 15 ml toluene was refluxed for 8 hours. Toluene was evaporated in vacuum and crude oil was purified by Combiflash (PE-THF). Yield 43%

NMR (CDCl$_3$) δ: 0.05-011 (2H, q, CH); 0.43-0.49 (2H, q, CH); 0.83-0.89(1H, m, CH); 1.49(2H, m, CH); 1.74-1.79 (4H, m, CH); 2.76-2.80(6H, m, CH); 3.093-3.135 (2H, t, CH); 3.36-3.40 (2H, m, CH); 4.63-4.67 (1H, t, NH); 5.5(1H, t, NH); 7.09-7.12 (1H, d, CH); 7.23(1H, s, CH); 7.97-8.00 (1H, d, CH). Molecular ion observed [M−H]$^+$=378 consistent with the molecular formula C$_{16}$H$_{22}$F$_3$N$_3$O$_3$S.

Synthesis of Compound 95

N-Cyclopropylmethyl-4-(cyclopropylmethylamino)-2-trifluoromethyl-benzenesulfonamide Mixture of 4-bromo-N-cyclopropylmethyl-2-trifluoromethylsulfonamide (186 mg, 0.51 mmol), aminomethylcyclopropane (84 mg, 1.18 mmol), Pd(OAc)₂ (27 mg, 0.1 mmol), BINAP (63 mg, 0.1 mmol) and cesium carbonate (337 mg, 1.03 mmol) in 15 ml toluene was refluxed for 8 hours. Toluene was evaporated in vacuum and crude oil was purified by Combiflash (PE-THF). Yield 68%

NMR (CDCl$_3$) δ: 0.05-010 (2H, q, CH); 0.27-0.32(2H, q, CH); 0.43-0.49 (2H, q, CH); 0.59-0.65 (2H, q, CH); 0.83-0.89 (1H, m, CH); 1.08-1.13 (1H, q, CH); 1.49(2H, m, CH); 2.76-2.80(2H, t, CH); 3.03-3.05 (2H, d, CH); 4.60(1H, m, NH); 6.68-6.71 (1H, d, CH); 6.98(1H, s, CH); 7.96-7.99(1H, d, CH). Molecular ion observed [M–H]$^+$=349 consistent with the molecular formula $C_{15}H_{29}F_3N_3O_3S$.

Synthesis of Compound 96

4-Cyclohexylamino-N-cyclopropylmethyl-2-trifluoromethyl-benzenesulfonamide

Mixture of (187 mg, 0.51 mmol), aminomethylcyclohexane (101 mg, 0.89 mmol), Pd(OAc)$_2$ (26 mg, 0.1 mmol), BINAP (63 mg, 0.1 mmol) and cesium carbonate (344 mg, 1.05 mmol) in 15 ml toluene was refluxed for 8 hours. Toluene was evaporated in vacuum and crude oil was purified by Combiflash (PE-THF). Yield 48%

NMR (CDCl$_3$) δ: 0.06-0.08 (2H, q, CH); 0.43-0.47 (2H, q, CH); 0.83-0.89(1H, m, CH); 0.98-1.82 (11H, m, CH); 2.76-2.80(2H, m, CH); 3.01-3.05 (2H, d, CH); 4.60(1H,m, NH); 6.65-6.68 (1H, d, CH); 6.94(1H, s, CH); 7.94-7.97(1H, d, CH). Molecular ion observed [M–H]$^+$=391 consistent with the molecular formula $C_{18}H_{25}F_3N_3O_3S$.

Synthesis of Compound 97

4-Cyclopropylamino-N-cyclopropylmethyl-2-trifluoromethyl-benzenesulfonamide a) 4-Bromo-2-trifluoromethyl-benzenesulfonyl chloride (2.0 gr, 6.18 mmol) was added in one portion to a stirred solution of cyclopropyl-methylamine (1.1 gr, 15.5 mmol) in dry THF (60 mL), under N$_2$ atmosphere. After 24 h at rt, water and EtOAc were added, and the layers were separated. The organic layer was washed with 1 N HCl and saturated NaCl solutions, dried over sodium sulfate, filtered and evaporated. The clean product was obtained as a yellowish solid (2.21 gr, 100% yield), transferred to the next step without further purification.

b) The product of step (a) (120 mg, 0.33 mmol) was dissolved in dry toluene (12 mL) under N$_2$ atmosphere. To the stirring solution were added Pd(OAc)$_2$ (7.4 mg, 0.033 mmol), BINAP (23 mg, 0.036 mmol) and cesium carbonate (134 mg, 0.41 mmol) and the reaction mixture was stirred at rt for 20 min. Cyclopropylamine (29 mg, 0.50 mmol) was added and the mixture was stirred at rt for 10 min. Stirring was continued at 110° C. under N$_2$ atmosphere for 6 hours, cooled and allowed to proceed overnight at rt. The mixture was filtered through a small pad of silica gel on a sinter glass, eluted with additional amount of 30 mL toluene and then 50 mL EtOAc. 133 mg of yellowish crude oil obtained which was further purified using Combiflash (PE-THF) affording the clean desired product as a yellow oil (73 mg, 66% yield).

$^1$H NMR: (CDCl$_3$) δ 7.99 (d, 1H, CH); 7.11 (d, 1H, CH); 6.89 (dd, 1H, CH); 4.60 (bt, 1H, NH); 2.79 (t, 2H, CH$_2$N); 2.51 (septet, 1H, CH); 0.86 (m, 3H, CH+CH$_2$); 0.57 (m, 2H, CH$_2$); 0.46 (m, 2H, CH$_2$); 0.08 (m, 2H, CH$_2$).

MS: m/z 335.00 (MH$^+$).

Synthesis of Compound 98

N-Cyclopropylmethyl-4-(cyclopropylmethyl-propylamino)-2-trifluoromethyl-benzenesulfonamide a) 4-Bromo-2-trifluoromethyl-benzenesulfonyl chloride (2.0 gr, 6.18 mmol) was added in one portion to a stirred solution of cyclopropyl-methylamine (1.1 gr, 15.5 mmol) in dry THF (60 mL), under N$_2$ atmosphere. After 24 h at rt, water and EtOAc were added, and the layers were separated. The organic layer was washed with 1 N HCl and saturated NaCl solutions, dried over sodium sulfate, filtered and evaporated. The clean product was obtained as a yellowish solid (2.21 gr, 100% yield), transferred to the next step without further purification.

b) The product of step (a) (200 mg, 0.56 mmol) was dissolved in dry toluene (20 mL) under N$_2$ atmosphere. To the stirring solution were added Pd(OAc)$_2$ (12.5 mg, 0.056 mmol), BINAP (38 mg, 0.062 mmol) and cesium carbonate (237 mg, 0.73 mmol) and the reaction mixture was stirred at rt for 20 min. Cyclopropylmethyl-propylamine (253 mg, 2.23 mmol) was added and the mixture was stirred at rt for 10 min. Stirring was continued at 110° C. under N$_2$ atmosphere for 6 hours, cooled and allowed to proceed overnight at rt. The mixture was filtered through a small pad of silica gel on a sinter glass, eluted with additional amount of 30 mL toluene and then 50 mL EtOAc. 182 mg of yellowish crude oil obtained which was further purified using Combiflash (PE-THF) affording the clean desired product as a yellow oil (110 mg, 50.4% yield).

$^1$H NMR: (CDCl$_3$) δ 7.96 (d, 1H, CH); 7.04 (d, 1H, CH); 6.75 (dd, 1H, CH); 4.59 (t, 1H, NH); 3.38 (t, 2H, CH$_2$N); 3.27 (d, 2H, CH$_2$N); 2.78 (dd, 2H, CH$_2$N); 1.65 (m, 2H, CH$_2$CH$_2$N); 1.01 (m, 1H, CH); 0.95 (t, 3H, CH$_3$); 0.87 (m, 1H, CH); 0.60 (m, 2H, CH$_2$); 0.46 (m, 2H, CH$_2$); 0.27 (m, 2H, CH$_2$); 0.09 (m, 2H, CH$_2$).

MS: m/z 391.10 (MH$^+$).

Synthesis of Compound 99

N-Cyclopropylmethyl-4-(3-methoxy-propylamino)-2-trifluoromethyl-benzenesulfonamide a) 4-Bromo-2-trifluoromethyl-benzenesulfonyl chloride (2.0 gr, 6.18 mmol) was added in one portion to a stirred solution of cyclopropyl-methylamine (1.1 gr, 15.5 mmol) in dry THF (60 mL), under N$_2$ atmosphere. After 24 h at rt, water and EtOAc were added, and the layers were separated. The organic layer was washed with 1 N HCl and saturated NaCl solutions, dried over sodium sulfate, filtered and evaporated. The clean product was obtained as a yellowish solid (2.21 gr, 100% yield), transferred to the next step without further purification.

b) The product of step (a) (150 mg, 0.42 mmol) was dissolved in dry toluene (15 mL) under N$_2$ atmosphere. To the stirring solution were added Pd(OAc)$_2$ (9.4 mg, 0.042 mmol), BINAP (29 mg, 0.046 mmol) and cesium carbonate (171 mg, 0.53 mmol) and the reaction mixture was stirred at rt for 20 min. 3-Methoxy-propylamine (150 mg, 0.42 mmol) was added and the mixture was stirred at rt for 10 min. Stirring was continued at 110° C. under N$_2$ atmosphere for 6 hours, cooled and allowed to proceed overnight at rt. The mixture was filtered through a small pad of silica gel on a sinter glass, eluted with additional amount of 30 mL toluene and then 50 mL EtOAc. 175 mg of yellowish crude oil obtained which was further purified using Combiflash (PE-THF) affording the clean desired product as a yellow oil (75 mg, 49% yield).

$^1$H NMR: (CDCl$_3$) δ 7.96 (d, 1H, CH); 6.96 (d, 1H, CH); 6.69 (dd, 1H, CH); 4.63 (bs, 1H, NH); 3.54 (t, 2H, CH$_2$OCH$_3$); 3.37 (s, 3H, OCH$_3$); 3.31 (t, 2H, CH$_2$N); 2.78 (m, 2H, CH$_2$N); 1.92 (quint, 2H, NCH$_2$CH$_2$CH$_2$); 0.86 (m, 1H, CH); 0.45 (m, 2H, CH$_2$); 0.07 (m, 2H, CH$_2$).

MS: m/z 367.10 (MH$^+$).

Synthesis of Compound 100

N-Cyclopropylmethyl-4-[(pyridin-2-ylmethyl)-amino]-2-trifluoromethyl-benzenesulfonamide Mixture of 4-bromo-N-cyclopropylmethyl-2-trifluoromethylsulfonamide (187 mg, 0.52 mmol), 2-aminomethylpyridine (100 mg, 0.95 mmol), Pd(OAc)$_2$ (26 mg, 0.1 mmol), BINAP (63 mg, 0.1 mmol) and cesium carbonate (388 mg, 1.19 mmol) in 15 ml toluene was reflaxed for 8 hours. Toluene was evaporated in vacuum and crude oil was purified by Combiflash (PE-THF). Yield 24%

NMR (CDCl$_3$) δ: 0.07-0.11 (2H, q, CH); 0.43-0.50 (2H, q, CH); 0.83-0.89(1H, m, CH); 2.75-2.79(2H, m, CH); 4.98 (2H, bs, CH); 6.81(1H,m, NH); 6.79-6.82 (1H, dd, CH); 7.10-7.11(1H, d, CH); 7.85-7.98(1H, m, CH); 7.93-7.96(2H, m, CH); 8.40-8.45(1H, m, CH); 8.27-8.46(1H, d, CH). Molecular ion observed [M-H]$^+$=386 consistent with the molecular formula C$_{17}$H$_{18}$F$_3$N$_3$O$_2$S.

Synthesis of Compound 101

N-Cyclopropylmethyl-4-[(pyridin-3-ylmethyl)-amino]-2-trifluoromethyl-benzenesulfonamide Mixture of 4-bromo-N-cyclopropylmethyl-2-trifluoromethylsulfonamide (209 mg, 0.57 mmol), 3-aminomethylpyridine (108 mg, 1.0 mmol), Pd(OAc)$_2$ (24 mg, 0.1 mmol), BINAP (61 mg, 0.1 mmol) and cesium carbonate (388 mg, 1.19 mmol) in 15 ml toluene was reflaxed for 8 hours. Toluene was evaporated in vacuum and crude oil was purified by.

NMR (CDCl$_3$) δ: 0.09-0.13 (2H, q, CH); 0.47-0.51 (2H, q, CH); 0.83-0.89(1H, m, CH); 2.78-2.87(2H, m, CH); 4.64-4.69 (2H, m, CH); 5.81(1H, m, NH); 6.72 (1H, m, CH); 7.70-7.23(1H, m, CH); 7.95-7.98(1H, d, CH); 8.12-8.16(1H, m, CH); 8.63-8.65(1H, m, CH); 8.93(1H, s, CH). Molecular ion observed [M-H]$^+$=386 consistent with the molecular formula C$_{17}$H$_{18}$F$_3$N$_3$O$_2$S.

Synthesis of Compound 102

4-Butylamino-N-cyclopropylmethyl-2-trifluoromethyl-benzenesulfonamide

Mixture of 4-bromo-N-cyclopropylmethyl-2-trifluoromethylsulfonamide (300 mg, 0.92 mmol), 1-Butylamine (184 mg, 1.85 mmol), Pd(OAc)$_2$ (41 mg, 0.15 mmol), BINAP (110 mg, 0.17 mmol) and cesium carbonate (600 mg, 1.85 mmol) in 15 ml toluene was reflaxed for 8 hours. Toluene was evaporated in vacuum and crude oil was purified by Combiflash (PE-THF). Yield 29%

NMR (CDCl$_3$) δ: 0.03-0.08 (2H, q, CH); 0.44-0.47 (2H, m, CH); 0.83-0.94(1H, m, CH); 0.95-1.00(3H, t, CH); 1.43-1.64 (4H, m, CH); 2.75-2.80 (2H, t, CH); 3.17-3.21(2H, q, CH); 4.35 (1H, t, NH); 4.55 (1H, t, NH); 6.64-6.67 (1H, dd, CH); 6.92-6.93(1H, d, CH); 7.94-7.97(1H, d, CH). Molecular ion observed [M-H]$^+$=351 consistent with the molecular formula C$_{15}$H$_{21}$F$_3$N$_3$O$_2$S.

Synthesis of Compound 103

N-Cyclopropylmethyl-4-(morpholin-4-ylamino)-2-trifluoromethyl-benzenesulfonamide Mixture of 4-bromo-N-cyclopropylmethyl-2-trifluoromethylsulfonamide (90 mg, 0.25 mmol), 4-aminomorpholine (115 mg, 1.27 mmol), Pd(OAc)$_2$ (15 mg, 0.06 mmol), BINAP (44 mg, 0.07 mmol) and cesium carbonate (173 mg, 0.53 mmol) in 15 ml toluene was reflaxed for 8 hours. Toluene was evaporated in vacuum and crude oil was purified by Combiflash (PE-THF). Yield 62%

NMR (CDCl$_3$) δ: 0.05-0.10 (2H, q, CH); 0.43-0.49 (2H, q, CH); 0.84-0.89(1H, m, CH); 2.78-2.81(5H, m, CH); 3.83-3.89 (4H, m, CH); 4.64(1H,m, NH); 7.04-7.07(1H, dd, CH); 7.29-7.30(1H, d, CH); 7.99-8.02(1H, d, CH). Molecular ion observed [M-H]$^+$=378 consistent with the molecular formula C$_{15}$H$_{20}$F$_3$N$_3$O$_3$S.

Synthesis of Compound 104

N-Cyclopropylmethyl-4-[(pyridin-4-ylmethyl)-amino]-2-trifluoromethyl-benzenesulfonamide Mixture of 4-bromo-N-cyclopropylmethyl-2-trifluoromethylsulfonamide (157 mg, 0.44 mmol), 4-aminomethylpyridine (104 mg, 0.96 mmol), Pd(OAc)$_2$ (15 mg, 0.06 mmol), BINAP (40 mg, 0.07 mmol) and cesium carbonate (320 mg, 1.0 mmol) in 15 ml toluene was reflaxed for 8 hours. Toluene was evaporated in vacuum and crude oil was purified by Combiflash (PE-THF). Yield 39%

NMR (CDCl$_3$) δ: 0.09-0.13 (2H, q, CH); 0.47-0.51 (2H, q, CH); 0.83-0.89(1H, m, CH); 2.78-2.87(2H, m, CH); 4.64-4.69 (2H, m, CH); 5.81(1H, m, NH); 6.72 (1H, m, CH); 7.70-7.23(1H, m, CH); 7.95-7.98(1H, d, CH); 8.12-8.16(1H, m, CH); 8.63-8.65(1H, m, CH); 8.93(1H, s, CH). Molecular ion observed [M-H]$^+$=386 consistent with the molecular formula C$_{17}$H$_{18}$F$_3$N$_3$O$_2$S.

Synthesis of Compound 105

4-(Azepan-1-ylamino)-N-cyclopropylmethyl-2-trifluoromethyl-benzenesulfonamide Mixture of 4-bromo-N-cyclopropylmethyl-2-trifluoromethylsulfonamide (218 mg, 0.61 mmol), 1-azepan-ylamine (113 mg, 1.08 mmol), Pd(OAc)$_2$ (26 mg, 0.1 mmol), BINAP (76 mg, 0.1 mmol) and cesium carbonate (318 mg, 1.0 mmol) in 15 ml toluene was reflaxed for 8 hours. Toluene was evaporated in vacuum and crude oil was purified by Combiflash (PE-THF). Yield 29%

NMR (CDCl$_3$) δ: 0.61-0.11 (2H, q, CH); 0.43-0.49 (2H, q, CH); 0.83-0.94(1H, m, CH); 1.56-1.78(8H, m, CH); 2.77-2.81 (2H, t, CH); 3.06(4H, m, CH); 4.6 (1H, m, CH); 7.1-7.2 (1H, d, CH); 7.33(1H, s, CH); 7.97-8.08(1H, d, CH). Molecular ion observed [M-H]$^+$ 392 consistent with the molecular formula C$_{17}$H$_{24}$F$_3$N$_3$O$_2$S.

Synthesis of Compound 106

4-(Azepan-1-ylamino)-N-(1-cyclopropyl-1-methyl-ethyl)-2-trifluoromethyl-benzenesulfonamide Mixture of 4-bromo-N-(1-cyclopropyl-1-methylethyl)1-2-trifluoromethylsulfonamide (184 mg, 0.47 mmol), 1-azepan-ylamine (108 mg, 0.97 mmol), Pd(OAc)$_2$ (24 mg, 0.1 mmol), BINAP (63 mg, 0.1 mmol) and cesium carbonate (350 mg, 1.07 mmol) in 15 ml toluene was refluxed for 8 hours. Toluene was evaporated in vacuum and crude oil was purified by Combiflash (PE-THF). Yield 41%

NMR (CDCl$_3$) δ: 0.29-0.32 (2H, q, CH); 0.43-0.49 (2H, q, CH); 0.83-0.94(1H, m, CH); 1.125 (6H, s, CH); 1.56-1.86 (8H, m, CH); 3.21(4H, m, CH); 4.73 (1H, s, CH); 7.25-7.3 (1H, d, CH); 7.33(1H, s, CH); 8.1-8.13(1H, d, CH). Molecular ion observed [M-H]$^+$=420 consistent with the molecular formula C$_{19}$H$_{28}$F$_3$N$_3$O$_2$S.

Synthesis of Compound 107

N-(1-Cyclopropyl-1-methyl-ethyl)-4-(piperidin-1-ylamino)-2-trifluoromethyl-benzenesulfonamide a) 4-Bromo-2-trifluoromethyl-benzenesulfonyl chloride (1.19 gr, 3.69 mmol) was added in one portion to a stirred solution of 1-cyclopropyl-1-methyl-ethylamine, toluene-4-sulfonate (1.0 gr, 3.69 mmol) in dry DCM (40 mL), under N$_2$ atmosphere. After 24 h at rt, water and EtOAc were added, and the layers were separated. The organic layer was washed with 1 N HCl and saturated NaCl solutions, dried over sodium sulfate, filtered and evaporated. The clean product was obtained as a yellow oil (1.26 gr, 88.5% yield), transferred to the next step without further purification.

b) The product of step (a) (130 mg, 0.34 mmol) was dissolved in dry toluene (12 mL) under N$_2$ atmosphere. To the stirring solution were added Pd(OAc)$_2$ (7.5 mg, 0.034 mmol), BINAP (23 mg, 0.037 mmol) and cesium carbonate (144 mg, 0.442 mmol) and the reaction mixture was stirred at rt for 20 min. 1-Aminopiperidine (51 mg, 0.51 mmol) was added and the mixture was stirred at rt for 10 min. Stirring was continued at 110° C. under N$_2$ atmosphere for 6 hours, cooled and allowed to proceed overnight at rt. The mixture was filtered through a small pad of silica gel on a sinter glass, eluted with additional amount of 30 mL toluene and then 50 mL EtOAc. 250 mg of yellowish crude oil obtained which was further purified using Combiflash (PE-THF) affording the clean desired product as a yellow oil (51 mg, 37% yield).

$^1$H NMR: (CDCl$_3$) δ 8.05 (d, 1H, CH); 7.26 (d, 1H, CH); 7.04 (d, 1H, CH); 5.22 (bs, 1H, NH); 4.65 (s, 1H, NH); 2.72 (bs, 4H, CH$_2$N); 1.74 (quint, 4H, CH$_2$N); 1.11 (m, 1H, CH); 1.10 (s, 6H, CH$_3$); 0.98 (m, 1H, CH); 0.28 (m, 4H, CH$_2$).

MS: m/z 406.10 (MH$^+$).

Synthesis of Compound 108

4-Cyclohexylamino-N-(1-cyclopropyl-1-methyl-ethyl)-2-trifluoromethyl-benzenesulfonamide a) 4-Bromo-2-trifluoromethyl-benzenesulfonyl chloride (1.19 gr, 3.69 mmol) was added in one portion to a stirred solution of 1-cyclopropyl-1-methyl-ethylamine, toluene-4-sulfonate (1.0 gr, 3.69 mmol) in dry DCM (40 mL), under N$_2$ atmosphere. After 24 h at rt, water and EtOAc were added, and the layers were separated. The organic layer was washed with 1 N HCl and saturated NaCl solutions, dried over sodium sulfate, filtered and evaporated. The clean product was obtained as a yellow oil (1.26 gr, 88.5% yield), transferred to the next step without further purification.

b) The product of step (a) (106 mg, 0.27 mmol) was dissolved in dry toluene (12 mL) under N$_2$ atmosphere. To the stirring solution were added Pd(OAc)$_2$ (6.2 mg, 0.027 mmol), BINAP (18.5 mg, 0.03 mmol) and cesium carbonate (114 mg, 0.35 mmol) and the reaction mixture was stirred at rt for 20 min. Cyclohexylamine (41 mg, 0.41 mmol) was added and the mixture was stirred at rt for 10 min. Stirring was continued at 110° C. under N$_2$ atmosphere for 6 hours, cooled and allowed to proceed overnight at rt. The mixture was filtered through a small pad of silica gel on a sinter glass, eluted with additional amount of 30 mL toluene and then 50 mL EtOAc. 180 mg of yellowish crude oil obtained which was further purified using Combiflash (PE-THE) affording the clean desired product as a yellow oil (31 mg, 28% yield).

$^1$H NMR: (CDCl$_3$) δ 8.01 (d, 1H, CH); 6.89 (bs, 1H, CH); 6.65 (bd, 1H, CH); 4.62 (s, 1H, NH); 3.32 (m, 1H, CHN); 2.04 (m, 2H, CH$_2$); 1.79 (m, 2H, CH$_2$); 1.68 (m, 1H, CH); 1.22 (m, 4H, CH$_2$); 1.10 (s, 6H, CH$_3$); 0.98 (m, 1H, CH); 0.28 (m, 4H, CH$_2$).

MS: m/z 405.10 (MH$^+$).

Synthesis of Compound 109

4-(4-Cyano-3-trifluoromethyl-phenylamino)-N-cyclopropylmethyl-2-trifluoromethyl-benzenesulfonamide Mixture of 4-bromo-N-cyclopropylmethyl-2-trifluoromethylsulfonamide (178 mg, 0.48 mmol), 4-amino-2-trifluoromethyl-benzonitrile (130 mg, 0.69 mmol), Pd(OAc)$_2$ (24 mg, 0.1 mmol), BINAP (66 mg, 0.10 mmol) and cesium carbonate (225 mg, 0.69 mmol) in 15 ml toluene was refluxed for 8 hours. Toluene was evaporated in vacuum and crude oil was purified by Combiflash (PE-THF). Yield 41%

NMR (CDCl$_3$) δ: 0.11-0.17 (2H, q, CH); 0.48-0.54 (2H, q, CH); 0.83-0.94(1H, m, CH); 2.88-2.92 (2H, t, CH); 4.75 (1H, m, NH); 6.79 (1H, m, NH); 7.35-7.41 (2H, dd, CH); 7.45(1H, s, CH); 7.54(1H, s, CH); 7.78-8.81(1H, d, CH); 8.19-8.22 (1H, d, CH). Molecular ion observed [M-H]$^+$=464 consistent with the molecular formula C$_{19}$H$_{15}$F$_6$N$_3$O$_2$S.

Synthesis of Compound 110

N-Cyclopropylmethyl-2-trifluoromethyl-4-(1,6,6-trimethyl-bicyclo[3.1.1]hept-3-ylamino)-benzenesulfonamide Mixture of 4-bromo-N-cyclopropylmethyl-2-trifluoromethylsulfonamide (188 mg, 0.52 mmol), (1R,2R,3R,5S)-(−)-isopinocampheneylamine (112 mg, 0.73 mmol), Pd(OAc)$_2$ (29 mg, 0.13 mmol), BINAP (77 mg, 0.12 mmol) and cesium carbonate (288 mg, 0.88 mmol) in 15 ml toluene was refluxed for 8 hours. Toluene was evaporated in vacuum and crude oil was purified by Combiflash (PE-THF). Yield 20%

NMR (CDCl$_3$) δ: 0.11-0.17 (2H, q, CH); 0.44-047(2H, q, CH); 0.83-0.94(1H, m, CH); 0.91-0.95(1H, d, CH); 1.075 (3H, s CH); 1.16-1.19 (3H, d, CH); 1.26 (3H, s, CH); 1.58-1.62 (1H, m, CH); 1.84-1.90 (2H, m, CH); 2.00-2.03 (1H, m, CH); 2.39-2.46 (1H, m, CH); 2.61-2.71 (1H, m, CH); 2.76-2.80 (2H, t, CH); 3.74 (1H, m, CH); 4.33 (1H, m, NH); 4.58 (1H, m, NH); 6.49-6.69 (2H, dd, CH); 6.93(1H, d, CH); 7.94-7.97(1H, s, CH). Molecular ion observed [M-H]$^+$=431 consistent with the molecular formula C$_{21}$H$_{29}$F$_3$N$_2$O$_2$S.

Example 2

Structures and Selected Properties

The structures of the compounds prepared according to the synthetic procedures disclosed above in Example 1 are presented in tabulated form in FIG. 1. Information regarding certain physicochemical properties of some of these compounds is also included. Expected water solubility (g/l), logP and logD at pH 7 were calculated using Advanced Chemistry Development software (ACD labs, version 4.04). The logP value is the logarithm of the partition coefficient of the compound in organic phase/water systems, wherein the organic solvent is usually octanol. Contrary to logP, wherein the neutral form of a compound is accounted for, logD expresses the hydrophobicity of the compound at a given pH, considering all species of the compound. The logD value is the logarithm of the distribution coefficient at a given pH. Both logP and logD are considered predictive of the hydrophobicity/lipophilicity, hence of the solubility of the drug, and are parameters of some relevance to the expected ADME (Absorption, Distribution, Metabolism, and Excretion) profile of the drug. When available, the binding affinity toward the human cannabinoid receptors ($CB_1$, $CB_2$), expressed in $IC_{50}$ (nM), as assayed according to Example 30 below, is indicated.

Evaluation of the therapeutic effects of the novel compounds of the invention was carried out in a series of experimental systems to support the utility of these drugs. Most of the techniques used to prepare the in vitro or in vivo models, testing the compounds and analyzing the outcome are widely practiced in the art, and most practitioners are familiar with the standard resource materials that describe specific conditions and procedures. However, for convenience, the following descriptions may serve as guidelines.

Unless otherwise indicated, the test compounds are prepared as follows: for in vitro assays the compounds are first dissolved in DMSO and then stepwise diluted in the assay buffer, generally tissue culture medium, down to a final concentration of 0.1% DMSO. For in vivo assays the test compounds are first diluted in CREMOPHOR EL®:ethanol (70% and 30% w/w respectively) and further diluted 1:20 in physiological buffer, generally saline, to reach the appropriate dose. Thus, the vehicle is the original "solvent" diluted in the appropriate buffer.

All experimentations in animals were performed under humane conditions according to the Israeli Law for Animal Protection—Experiments in Animal 1994. All studies were reviewed by internal ethics committee and approved by the National responsible authority. Unless otherwise stated, animals were acclimated one week before initiation of study, and maintained under controlled environment. Animals were housed, at most 5 per cage for rats and at most 10 per cage for mice, on a 12 hours light/12 hours dark regimen, at a constant temperature of 22±4° C. and controlled humidity of 55±15% RH, with pellets of rodent diet and drinking filtered water ad libitum. At the end of the experiments, the animals were euthanized with an i.p. injection of 100 mg/kg sodium pentobarbitone (CTS). As a rule, the experiments were performed and the various scores measured by persons blinded to the treatment group.

BIOLOGICAL SECTION

Example 3

Binding Affinity for the CB1 and CB2 Receptors

The binding assays were performed by testing the ability of the new compounds to displace the radiolabeled synthetic non-selective cannabinoid agonist [$^3$H]CP55940 (168 Ci/mmol; PerkinElmer) from the human $CB_1$ ($hCB_1$) or human $CB_2$ ($hCB_2$) receptors on membranes derived from stably transfected HEK-293 cells (PerkinElmer). Membranes were diluted in assay buffer (50 mM Tris-HCl, 1 mM EDTA, 1 mM $MgCl_2$, 1 mg/ml BSA, pH=7.4). The amount of membrane was determined for each batch of membranes according to protein binding assay. The minimum amount of membrane that gave 50% specific binding was used for the binding assay. In most assays, binding was tested using 8 µg and 4 µg protein of $hCB_1$ and $hCB_2$ membranes, respectively. The tested compounds were dissolved in DMSO and diluted in assay buffer to a final concentration of 0.1% solvent. Total binding of [$^3$H]CP55940 was evaluated with 1.5 nM to $hCB_1$ and with 0.5 nM to $hCB_2$, according to $K_d$ affinity of [$^3$H]CP55940 for the respective membranes. The ability of the tested compounds to displace [$^3$H]CP55940 was evaluated first at a single concentration point of 100 nM for binding toward $hCB_2$ or $hCB_1$. In certain cases, the displacement was tested at compound concentrations ranging from 0.03 nM to 10 µM. Non-specific binding was measured by the addition of 1 µM of unlabelled CP55940 to the tubes. Binding assays were performed in triplicate in a total volume of 500 µl for 60 minutes at 30° C., in a shaking bath. Free and bound radioligands were separated by rapid filtration through GF/C filter plates (PerkinElmer) that had been presoaked with 0.1% Polyethylenimine (Sigma). Filters were shaken for 1 hour in 7 ml scintillation fluid (PerkinElmer) and radioactivity was determined by liquid scintillation counter (Wallac; PerkinElmer). For binding analysis, log concentration was plotted versus percent of specific binding out of total binding (Prism; GraphPad). $IC_{50}$ values were extrapolated from this plot.

Results are reported in FIG. 1. For compounds tested over a range of concentrations allowing the appropriate calculations, the values reported ($CB_1$, $CB_2$) represent the $IC_{50}$ of the compound in nM, unless otherwise indicated in the Figure. As can be seen in FIG. 1, compounds of the invention either bind or not bind to human cannabinoid receptors at the concentrations tested. Certain compounds bind more selectively to the $CB_2$ receptor over the $CB_1$ receptor, whereas other compounds have relatively lower selectivity.

Example 4

[$^{35}$S]GTPγS-Binding Assay

Functional activity of compounds of the invention toward the cannabinoid receptors was determined by stimulation of [$^{35}$S]-GTPγS binding using membranes from HEK-293 cells expressing the hCB1 receptor and membranes expressing the hCB2 receptor derived from either Sf9 (PerkinElmer) or from HEK-293 cells. Activities were compared to that of the known cannabinoid full agonist CP55940 (Alexis). The purpose of this experiment is to determine the potency of the compounds of the invention as agonists or antagonists toward each of the receptor tested.

[$^{35}$]-GTPγS binding reactions were performed at 30° C. in 96-well plates containing 5-10 µg membrane protein suspended in 0.1 ml binding buffer (20 mM HEPES-NaOH, pH 7.4, 5 mM $MgCl_2$, 100 mM NaCt, 0.2% (w/v) bovine serum albumin) supplemented with 50 µM GDP and 0.06 nM-10 µM of the compound being tested. Binding was initiated by the addition of [$^{35}$S]GTPγS (0.3 nM final concentration). Incubations were performed for 90 minutes and were terminated by filtration on GF/C filter plates (PerkinElmer). Filters were washed ten times with ice-cold wash buffer (20 mM HEPES-NaOH, pH 7.4, 10 mM sodium pyrophosphate). Non-specific binding was measured in the presence of 15 µM GTPγS.

Assays were performed in duplicates. Data was analyzed by plotting on the X axis the log concentration against percent of specific [$^{35}$S]GTPγS binding out of basal [$^{35}$S]GTPγS binding on the Y axis, non-linear regression is then performed using GraphPad Prism, version 3.0 (GraphPad, San Diego, Calif.) to calculate the $EC_{50}$ and $E_{max}$ of the compound. The $EC_{50}$ value represents the concentration at which there is 50% [$^{35}$S]GTPγS binding and the $E_{max}$ value the upper plateau of the curve.

CP55940 is a full agonist of the human and rat CB2 receptors. The full agonistic activity elicited with control cannabinoid agonist CP55940 yielded $E_{max}$ values 50 to 70% for the $CB_2$ receptor. The $EC_{50}$ values of the control were comparable to what has been reported in the literature. Compounds having an $EC_{50}$ value below 100 nM are considered to be potent agonists. Full or partial agonism at the receptor was determined relative to the $E_{max}$ value of CP55940. Percent of activity was calculated by dividing the $E_{max}$ value of the compound to the $E_{max}$ value of CP55940 (which represents 100% activity): A full agonist of the CB2 receptor demonstrates 90-100% activity relative to CP55940, a partial agonist demonstrates 30-90% activity relative to CP55940; and a weak partial agonist demonstrates <30% activity relative to CP55940 (Table 1).

TABLE 1

Functional activity at the human CB2 receptor

| Compound name | Cell line | EC50 | Emax (%) | % Activity (relative to CP55,940) |
|---|---|---|---|---|
| PRS-486,003 | C2-4 | 43 | 30 | 46 |
| PRS-486,004 | C2-4 | 365 | 26 | 51 |
| PRS-486,026 | C2-4 | 40 | 19 | 35 |
| PRS-486,035 | C2-4 | 20 | 19 | 35 |
| PRS-486,041 | C2-4 | 42 | 26 | 36 |
| PRS-486,044 | C2-4 | 124 | 5 | 9.8 |
| PRS-486,058 | C2-4 | 17 | 29 | 40 |
| PRS-486,074 | C2-4 | 168 | 30 | 45 |
| PRS-486,087 | C2-4 | 51 | 21 | 29 |
| PRS-486,088 | C2-4 | 4.6 | 5 | 9.8 |
| PRS-486,094 | C2-4 | 14.7 | 20 | 30 |
| PRS-486,105 | C2-4 | 141 | 34 | 43 |
| PRS-486,108 | C2-4 | 2310 | 39 | 49.3 |

Example 5

Analgesic Effect on Neuropathic Pain

Neuropathic pain, associated with chronic pain, differs from previously assessed visceral and inflammatory pain, associated with acute pain. Acute pain and chronic pain differ in their etiology, pathophysiology, diagnosis and treatment. Acute pain is nociceptive in nature and occurs secondary to chemical, mechanical and thermal stimulation of A-delta and C-polymodal pain receptors. Acute pain is self-limiting and will vanish on short-term after initial injury. Chronic pain, on the other hand, is continuous and can persist for years after the initial injury. It is produced by damage to, or pathological changes in the peripheral or central nervous system. Neuropathic pain tends to be only partially responsive to opioid therapy. Drugs active against certain types of acute pain such as visceral pain and inflammatory pain are therefore not necessarily effective against neuropathic pain.

The analgesic activity of compounds of the invention is assessed in a chronic constriction induced (CCI) model of neuropathic pain. A peripheral neuropathy is induced in the left hind limb of rats following a chronic constriction of the sciatic nerve according to Bennet et al. (Bennet, G. J. & Xie, Y-K., Pain 33: 87-107, 1988). The development of mechanical hyperalgesia is monitored using an established behavioral test analgesy meter or dynamic planter aesthesiometer.

Pre-surgery baseline values are ascertained as the mean of 2 pre-surgery values. Once the baseline values are established, the animals are surgically prepared by constricting the left sciatic nerve with 4-0 chromic catgut loose ligatures. On day 14 post-operation, the animals that have developed mechanical allodyina are arbitrarily allocated to the various treatment groups receiving either 7 or 14 days of administration based on the pre-treatment values.

The design is randomized, performed in a masked fashion as to whether drug or vehicle is being given. Male Sprague Dawley rats (average body weight 200 g, Harlan, Israel) are allowed to acclimatize to the behavioural testing equipment prior to testing. On the testing day, 24 hours after administration period lapsed, the differences between ipsilateral and contralateral hind leg thresholds were measured in grams using the Dynamic planter aesthesiometer or analgesy meter (Ugo basile).

Administration of Compound 4 of the invention (10 mg/kg, s.i.d) for 14 days produced a significant reduction of the CCI induced hyperalgesia (FIG. 2). Results are expressed as mean±SEM for each treatment group and the differences among those groups are analyzed by analysis of variance (ANOVA) followed by post-hoc analysis using Tukey's test. A value of p<0.05 is considered to be statistically significant.

Example 6

Analgesic Activity in Acute and Chronic Inflammatory Pain

Acute Inflammatory Pain. The purpose of this study is to test the analgesic activity of the compounds in inflammatory pain. Inflammatory pain is nociceptive in nature, wherein the pain sensation is often perceived for longer period than in acute pain. In the present model the duration of the preventive activity of compounds against inflammatory acute pain was assessed for up to about three hours post-drug administration. Inflammatory pain and paw edema were induced by intraplantar injection of 50% Complete Freund's Adjuvant (CFA) suspension in the animal hind paw.

Male Sprague Dawley rats (average body weight 200 g, Harlan, Israel) were transiently sedated by placement on dry ice for the duration of the injections. Rats were injected subcutaneously, in the subplantar region of one (right) paw with 0.1 ml of 50% w/v CFA in sterile saline. The contralateral (left) paw was not injected as data from the literature, confirmed by our own experience, showed that injection of 0.1 ml of normal saline did not affect later analgesic measurements. Test compounds were administered i.p. at initial single dose of 10 mg/kg, and volume dose of 5 ml/kg, twenty-four hours post CFA injection. Vehicle and Celecoxib (a non-steroidal anti-inflammatory analgesic drug for acute pain relief) treated animals were used as controls. Each treatment group comprised at least six animals.

Prior to, 24 hours post induction of inflammatory pain and one and three hours after drug administration, the animals reactions to pain stimuli were tested by mechanical stimulus. The mechanical (tactile) analgesia was assessed using a Dynamic Plantar Aesthesiomether (Ugo Basile Model 73400-002). The system was set on maximal force of 50 grams and the force applied was gradually increased at the rate of 10 g/sec. At the end of the study, animals were euthanized.

The results are presented as the force needed for hind paw withdrawal before surgery, 24 hours post surgery and 1 and 3 hours post drug administration. Results are expressed as mean±SEM for each treatment group and the differences among those groups are analyzed by analysis of variance (ANOVA). A value of p<0.05 was considered to be statistically significant and is indicated on the figure by an asterisk over the relevant treatment group. Two asterisks indicate a p value below 0.01 and three asterisks indicate a p value below 0.001.

Figure 3:
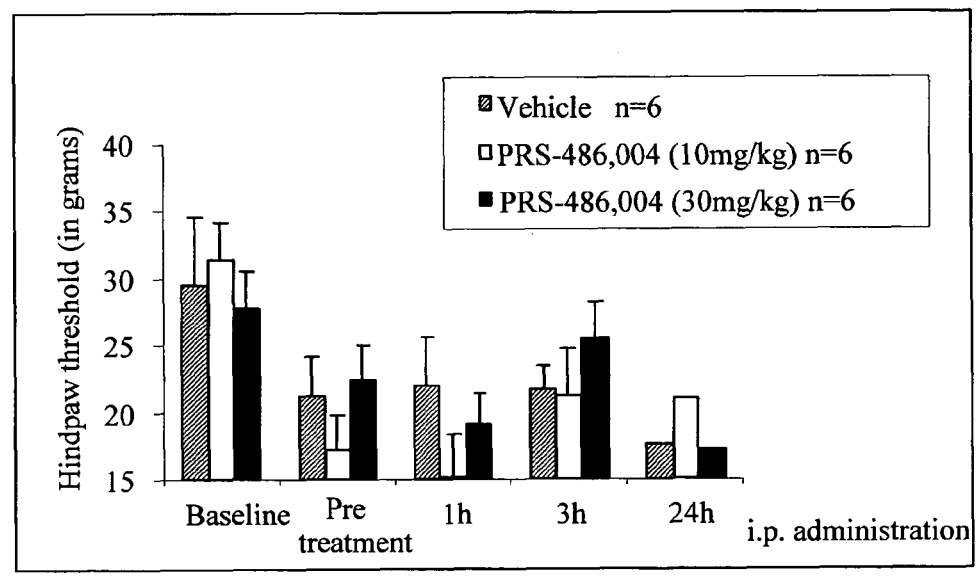
FIG. 3: shows the analgesic effect of an exemplary compound of the invention (compound 4 at a dose of 10 mg/kg and 30 mg/kg i.p) on inflammatory pain. The results are presented as the force needed for hind paw withdrawal before surgery, twenty-four hours post surgery and 1 and 3 hours post drug administration.

The baseline values for the force to be applied for left hind paw withdrawal following mechanical stimuli is about 30 gram before inflammatory pain induction. Twenty-four hours later, animals displayed a withdrawal threshold of 15-20 grams in the injured paw. Compounds of the invention were able to reduce this outcome. Results, expressed as Force measured in grams, are depicted in FIG. 3. As shown in FIG. 3, compound 4 of the invention reversed the pain threshold, three hours post administration, to injured paw by 50 to 100%, dose dependently (10 and 30 mg/kg, respectively).

Chronic Inflammatory Pain. A model of chronic inflammatory pain was used to assess the analgesic activity of the compounds of the invention in a model which closely correlates with chronic arthritis pain in humans. 150 µl, 50% w/v CFA in sterile saline, is injected into the left knee of rats. Animals are assessed for changes in weight bearing 18 hours post intra-articular injections, and thereafter once daily for 14 days. Naïve rats distribute their body weight equally between their two hind legs, upon an insult such as intra-articular injection of the left knee with adjuvant, the weight is distributed such that less weight is placed on the affected leg. Assessment of this change is an extremely sensitive method for measuring "incident" pain. Rats were dosed with drugs 14-days post intra-articular injection for three to five days and weight bearing was measured 1 hour post-administration on each day.

Male Sprague Dawley rats (average body weight 200 g, Harlan, Israel) were anesthetized using 3% Halotane in oxygen. The left knee was shaved and cleaned using a dilute Hibiscrub solution. The left knee of each rat was injected with 150 µl of CFA containing 1 mg/kg *Mycobacterium tuberculosis* (Sigma, Israel). Animals were allowed to recover from anaesthesia and assessed for changes in weight bearing the next day and every day for 14 days post injections. Injection of 0.15 ml of normal saline did not induce changes in weight bearing. Weight bearing on each hind leg was determined using a rat incapacitance tester (Linton Instrument, Norfolk, UK). Rats were placed in the incapacitance tester with their hind paws on separate sensors, and the percentage body weight distribution was calculated over a period of 4 sec. Data is expressed as percentage of contralateral weight bearing, with 100% values resulting from equal distribution across both hind legs. Test compounds were administered i.p. at initial single dose of 10 mg/kg, and volume dose of 5 ml/kg, 14-days post CFA injection to the knee and dosed for three to five days. One hour post drug administration on each day, weight bearing was measured.

Figure 4:
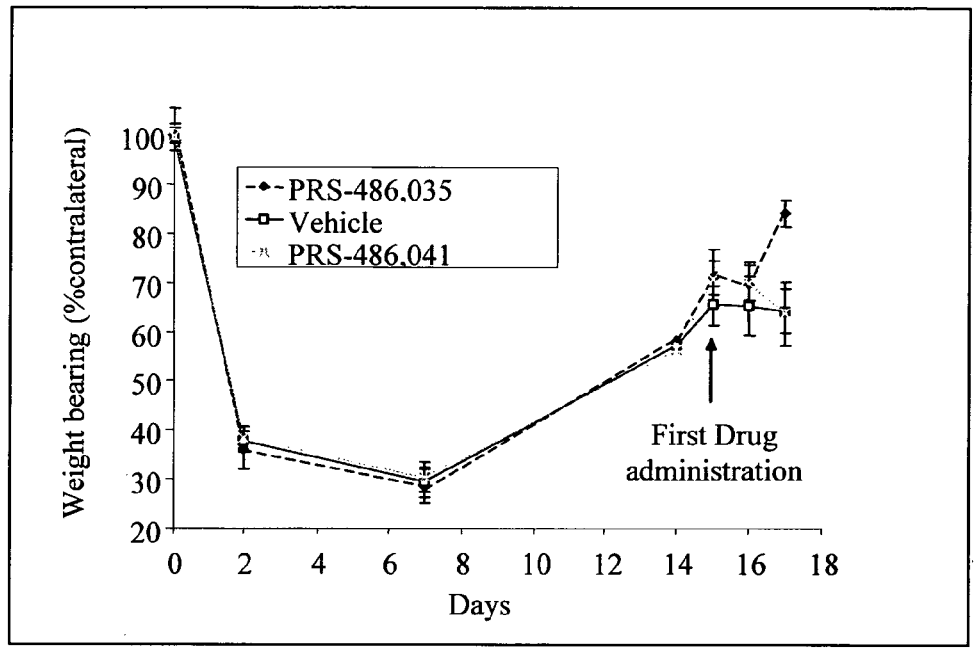
FIG. 4: shows the analgesic effect of exemplary compounds of the invention (compounds 35 and 41 at doses of 15 mg/kg b.i.d.) on chronic inflammatory pain. Results are presented as percent inhibition of writhing responses as compared to untreated group.

Administration of Compound 35 of the invention (15 mg/kg, b.i.d) for three days produced a significant reversal of the CFA induced hypersensitivity after three days of administration (FIG. 4). Reversal was progressive with maximal reversal observed after three days of administration, and an initial lower effect detected 1 hour after the first administration (day 15). Compound 41 of the invention produced a more modest analgesic effect at day 1 and 2 post administration (30% reversal).

These results confirm that compounds of the invention have analgesic activity in vivo in both acute and chronic inflammatory pain.

Example 7

Safety

The development of cannabinoid drugs is accompanied by added safety concern. As explained, the cannabimimetic effects are mediated through the CB1 receptor, and they are generally assessed in the Tetrad Assay wherein impact of compounds on the body temperature, spontaneous locomotor activity, catalepsy and response to heat induced pain are measured. In the present study, two parameters of the tetrad were monitored starting 15 minutes after compound administration: spontaneous locomotor activity and rectal temperature.

ICR male mice (average body weight 30 g, Harlan, Israel) were intravenously administered the compounds of the invention (compounds 3 and 4) at a dose of 2.5 and 10 mg/kg and at a volume dose of 5 ml/kg. Measurements were made starting 15 minutes following compound administration. All tests for each animal were completed within approximately 10 minutes. Rectal temperature (FIGS. 5 and 7) was monitored using a thermistor probe (YSI model 400, USA). Spontaneous locomotion (FIGS. 6 and 8) was assessed using the open field methodology: The number of squares crossed by the animals were recorded and analyzed during a period of three minutes. Results are expressed as average±SEM. At the end of the study, the animals were euthanized.

As shown in FIGS. 5-8, none of the tested compounds of the invention displayed adverse cannabimimetic activities in any of the parameters monitored at the dose of 2 mg/kg and 10 mg/kg i.v. HU-210, a synthetic cannabinoid 100-800% more potent than natural THC from *cannabis*, which served as control at a 100-fold lower dose, confirmed the validity of these models for the assessment of $CB_1$ related psychomimetic activity.

Figure 6:
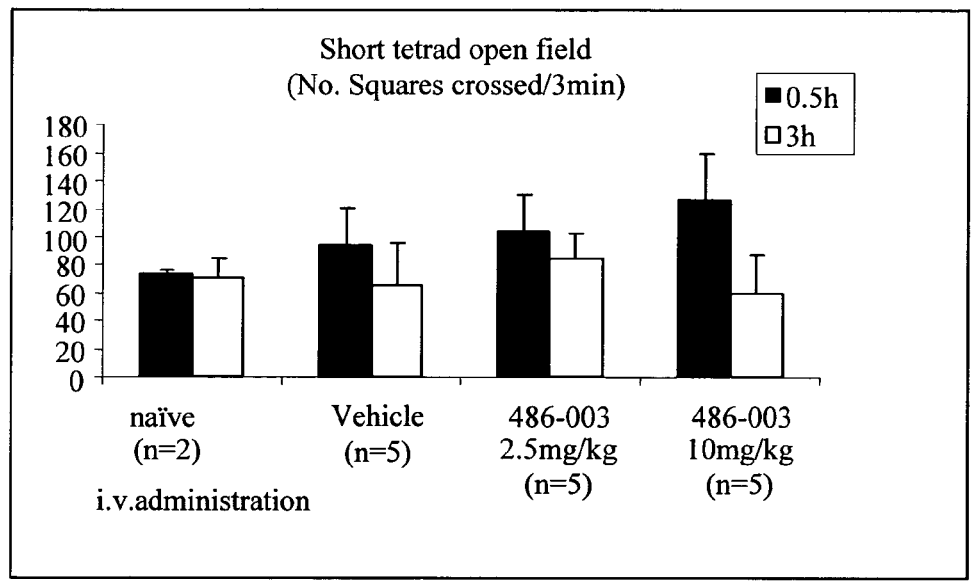
FIG. 6: shows the effect of compound 3 of the invention after i.v. administration at 2.5 mg/kg and 10 mg/kg on spontaneous locomotion assessed using the open field methodology. The number of squares crossed by the animals were recorded and analyzed during a period of three minutes.
Figure 8:
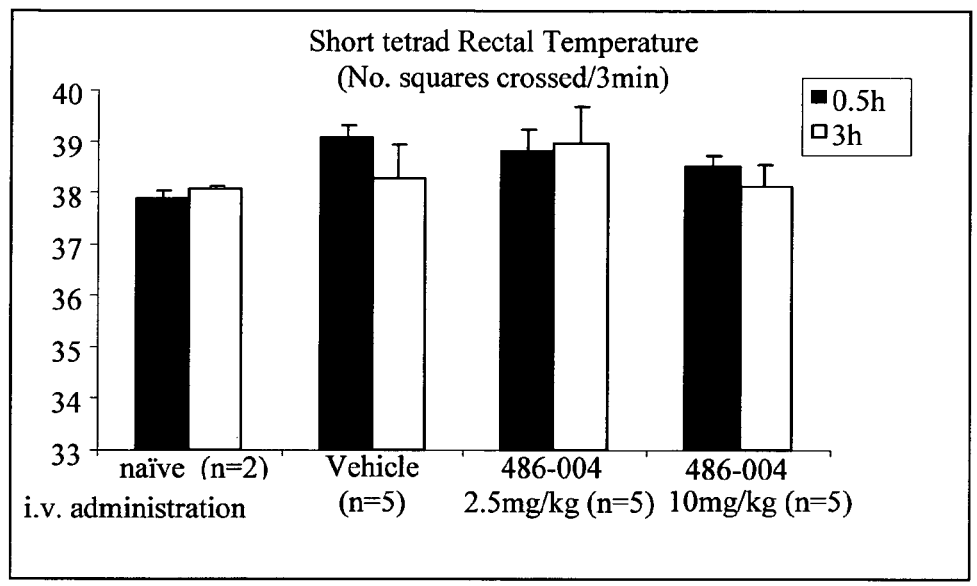
FIG. 8: shows the effect of compound 4 of the invention after i.v. administration at 2.5 mg/kg and 10 mg/kg on spontaneous locomotion assessed using the open field methodology. The number of squares crossed by the animals were recorded and analyzed during a period of three minutes.

For instance, over a period of three minutes naïve vehicle treated animals displayed similar behavior crossing on average 73.38±13.69 squares and an average of 95.63±6.24 squares, respectively (FIGS. 6 and 8). Compounds of the invention did not significantly affect spontaneous locomotor activity.

Figure 5:
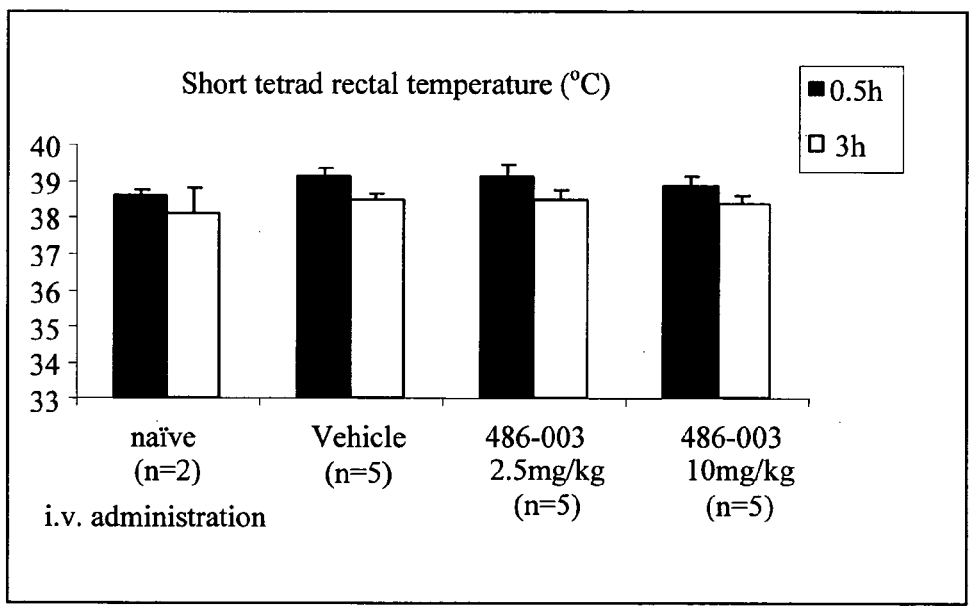
FIG. 5: shows the effect of compound 3 of the invention after i.v. administration at 2.5 mg/kg and 10 mg/kg on reduction of rectal temperature.
Figure 7:
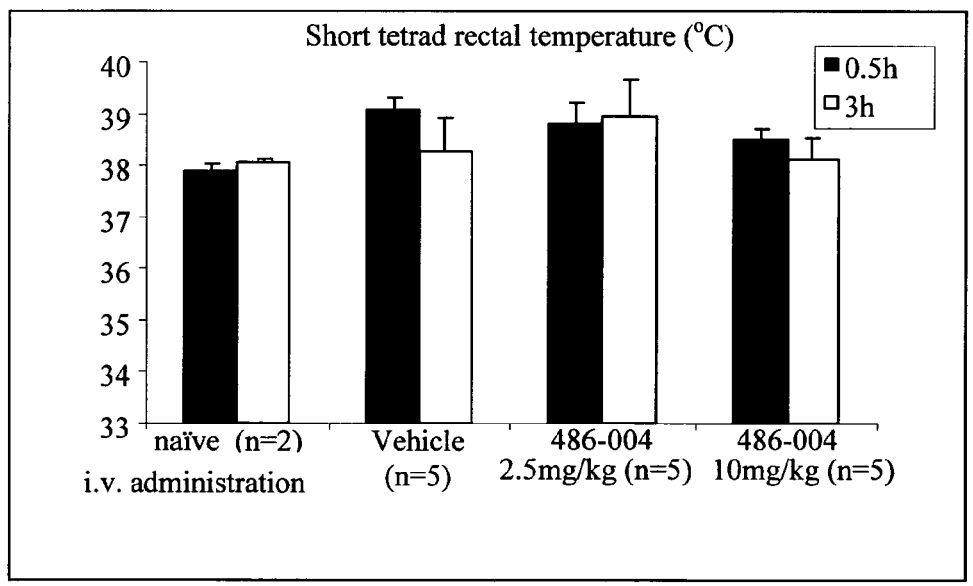
FIG. 7: shows the effect of compound 4 of the invention after i.v. administration at 2.5 mg/kg and 10 mg/kg on reduction of rectal temperature.

Similarly, naïve animals and vehicle treated animals had a rectal temperature of 38.68±0.25° C. and 38.88±0.11° C., respectively (FIGS. 5 and 7). Compounds of the invention did not affect the rectal temperatures of the animals.

Thus, compounds of the invention are devoid of deleterious cannabimimetic effects even at doses far exceeding those previously shown to have therapeutic benefits. Moreover, compounds of the invention are at least 100-fold safer than the psychoactive control HU-210.

Example 8

Thermal Analgesic Activity in CFA-Induced Inflammatory Acute Pain

The thermal analgesic effect induced by compounds of the present invention on inflammatory acute pain was assessed. Inflammatory pain and paw edema were induced by intraplantar injection of 50% Complete Freund's Adjuvant (CFA) suspension in the animal hind paw.

Male Sprague Dawley rats (average body weight 200 g, Harlan, Israel) were transiently sedated by placement on dry ice for the duration of the injections. Rats were injected subcutaneously, in the subplantar region of one (right) paw with 0.15 ml of 50% w/v CFA in sterile saline. The contralateral (left) paw was not injected as data from the literature, confirmed by our own observations, showed that injection of 0.15 ml of normal saline did not affect later analgesic measurements. Test compounds were administered i.p. at initial single dose of 10-60 mg/kg (depending on the test compound), and volume dose of 5 ml/kg, 24 hours post CFA injection. Vehicle and Celecoxib treated animals were used as controls. Each treatment group comprised at least six animals.

Prior to, 48 hours post induction of inflammatory pain and one hour after daily drug administration, the animals reaction to pain stimuli was tested by thermal stimulus. The thermal analgesia was assessed using a Plantar test (Ugo Basile). At the end of the study, animals were euthanized.

Figure 9:
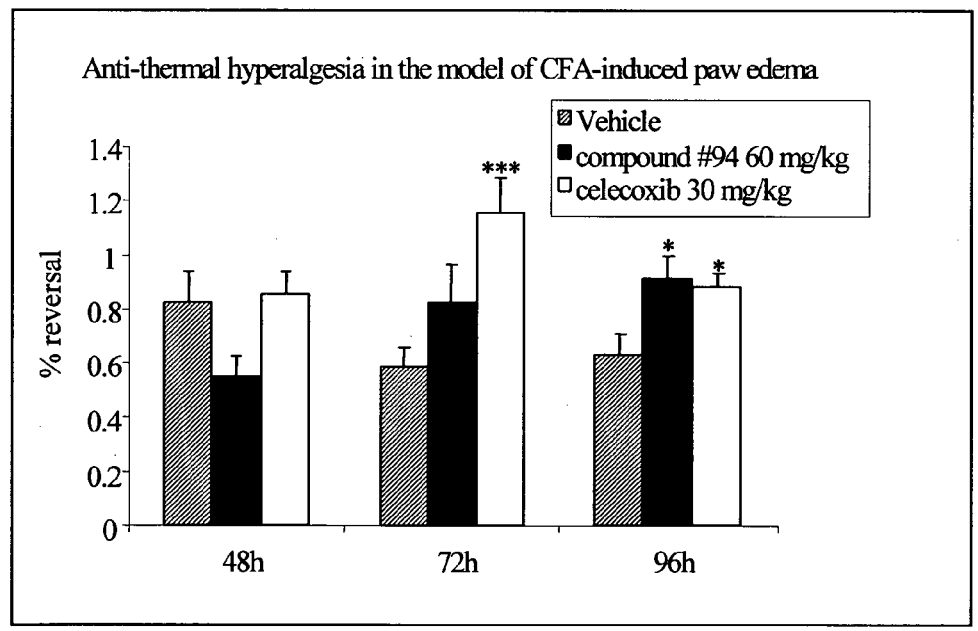
FIG. 9: shows the thermal analgesic effect of an exemplary compound of the invention (compound 94 at a dose of 60 mg/kg i.p.) on inflammatory acute pain. Results are expressed as percent of baseline value (% reversal).
Figure 10:
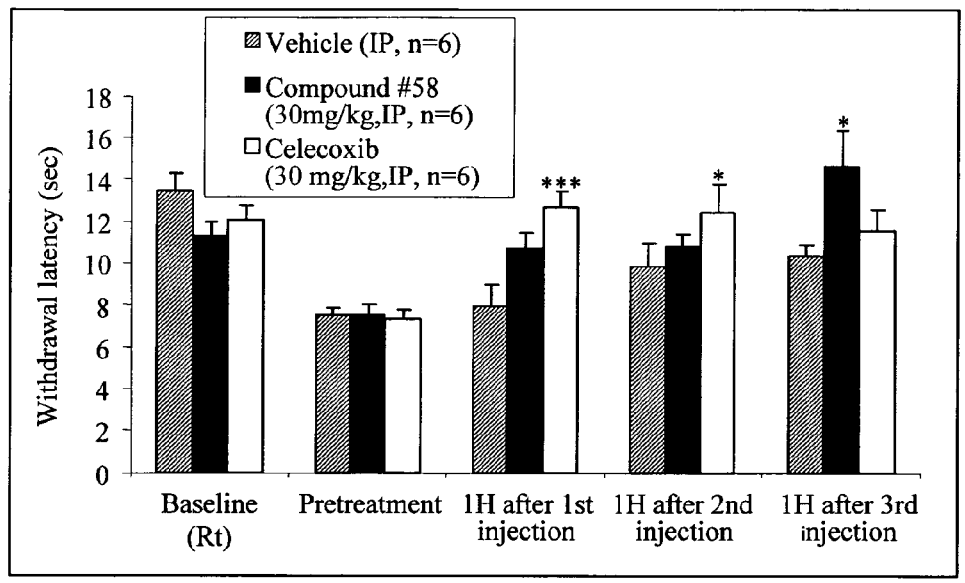
FIG. 10: shows the analgesic effect of compound 58 (at a dose of 30 mg/kg i.p.) on anti-thermal inflammatory hyperalgesia. Results are expressed as withdrawal latency.

Compounds of the invention were able to induce analgesia as seen by an increase in the withdrawal threshold. Results, expressed as percent of baseline value (% reversal) or withdrawal latency, are depicted in FIGS. 9 and 10. Compound 94 and 58 of the invention reversed the pain threshold, one hour post daily drug administration at the third day of treatment. Results are expressed as mean±SEM for each treatment group and the differences among those groups are analyzed by T-test. A value of p<0.05 was considered to be statistically significant and is indicated on the figure by an asterisk over the relevant treatment group. Two asterisks indicate a p value below 0.01 and three asterisks indicate a p value below 0.001.

Example 9

Activity of Compounds of the Invention in Inflammatory Bowel Diseases

CB2 receptors are expressed in the periphery, where they are primarily found on activated immune cells, mainly antigen-presenting cells and B cells. Several studies have suggested that agonists to this receptor may be of clinical importance in treating autoimmune diseases (Kimball et al., Am J Physiol Gastro Liver Physiol, 2006, 261:G364-71; Wright et al., Gastroenterology, 2005, 129:437-53; Rousseaux et al., Nat Med, 2007, 13:35-7).

In order to test the activity of compounds of the invention in an animal model of inflammatory bowel disease, female BALB/c mice 9-12 week old (Harlan, Israel) were used for Dextran Sulfate Salt (DSS)-induced acute colitis studies. Mice (ten per treatment group) were provided with a solution of tap water containing 5% DSS (MW. 36000-50000; MP Biomedicals, LLC) ad libitum over an 8 day period. The DSS solution was replenished every other day and switched to tap water at day 8. Body weight was measured daily. The clinical scores combined both macroscopic (diarrhea, body weight, mortality) as well as microscopic (pathological) scores. Diarrhea score in the studies for each animal represented the daily summary of stool consistency (scored as: 0, normal; 1, soft but still formed; 2, very soft; 3, diarrhea) and the presence of blood in stool (scored: 0, None; 1, visible blood traces in stool; 2, signs of blood; 3, rectal bleeding). At the end of experiment animals were euthanized and their colons are examined for signs of pathological damage. The pathological scores, colon length and weight were determined from the cecum to the anus (scored: 0, normal; 1, slight inflammation; 2, moderate inflammation and/or edema; 3, heavy inflammation and/or ulceration and/or edema).

Two compounds were tested in DSS-induced colitis in mice, compounds 4 and 58. Administered intraperitoneally both compounds demonstrated modest efficacy; statistical significance was observed in a least one of the experimental parameters, improvement in weight loss, clinical signs or gross pathology (Table 2). Results are expressed as mean ± SEM for each treatment group and the differences among those groups are analyzed by T-test. A value of p<0.05 was considered to be statistically significant and is indicated in the table by a crosshatch. Two crosshatches indicate a p value below 0.01 and three indicate a p value below 0.001. Asterisks denote statistical significant weight loss relative to animal weight in the beginning of the experiment.

TABLE 2

| Invention compounds demonstrating efficacy when dosed intraperitonealy | | | |
|---|---|---|---|
| Group | Percentage change in body weight | Clinical score | % Survival |
| Vehicle (i.p.) | −14 ± 2.28*** | 3.9 ± 0.6 | 90 |
| PRS-486,004 (20 mg/kg, i.p.) | −9.6 ± 1.59***# | 3.4 ± 0.7 | 90 |
| PRS-486,004 (40 mg/kg, i.p.) | −5 ± 2.3### | 3.1 ± 0.6 | 100 |
| Vehicle (i.p.) | −12.7 ± 1.8*** | 5.25 ± 0.13 | 80 |
| PRS-486,058 (10 mg/kg, i.p.) | −12.9 ± 2.6*** | 4.33 ± 0.22## | 100 |
| PRS-486,058 (30 mg/kg, i.p.) | −13.9 ± 2.3*** | 4.58 ± 0.2## | 100 |

Figure 11:
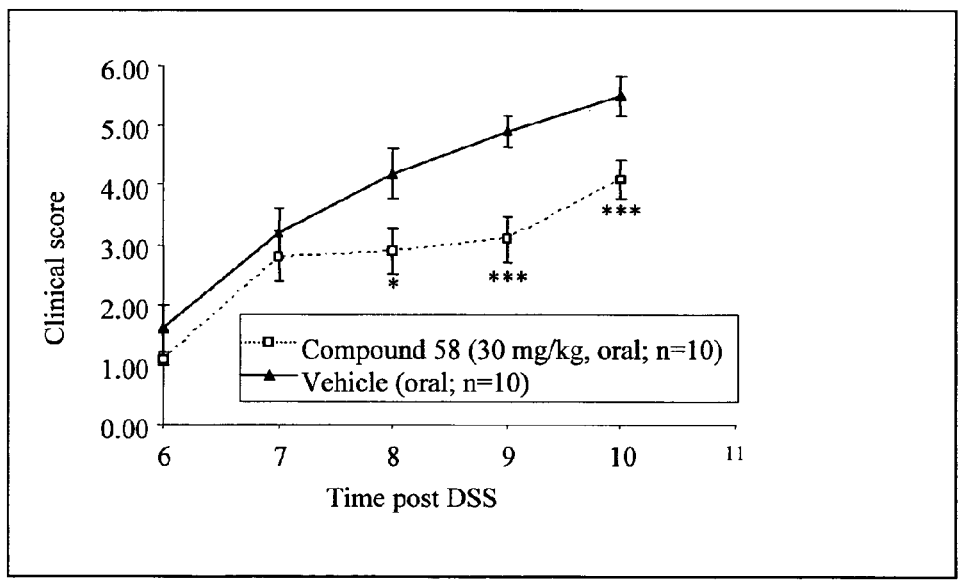
FIG. 11: shows the potential of compound of the invention (compound 58 at 30 mg/kg oral administration) in ameliorating chemically-induced colitis in mice, a model for inflammatory bowel disease. Results are expressed as clinical score over time.

Alternatively, compound 58 (30 mg/kg) was administered orally from the first day of DSS administration (day 1) until the end of the experiment (day 10). As shown in FIG. 11, a statistical significant amelioration of the clinical score was seen from day 8 until the end of the experiment. Furthermore, mortality was not observed in the drug-treated group, while 20% mortality rate was observed in the vehicle-treated group. The pathological score was also improved in drug-treated animals versus vehicle (1.9±0.5 and 2.88±0.55, respectively), although it did not reach statistical significance.

These results suggest that oral administration of the CB2 agonists of the invention decrease chemically-induced colitis, a model for inflammatory bowel disease. This gives validation to the potential use of these compounds as therapeutics in human IBD, including ulcerative colitis and Cohn's disease.

To the extent necessary to understand or complete the disclosure of the present invention, all publications, patents, and patent applications mentioned herein are expressly incorporated in their entirety by reference therein to the same extent as though each were individually so incorporated.

While the invention is capable of various modifications and alternative forms, specific embodiments thereof have been shown by way of example. It should be understood, however, that it is not intended to limit the invention to the particular forms disclosed but, on the contrary, the intention is to cover all modifications, equivalents, and alternatives falling within the spirit and scope of the invention as defined by the appended claims.

The invention claimed is:
1. A compound represented by the structure of formula (I):

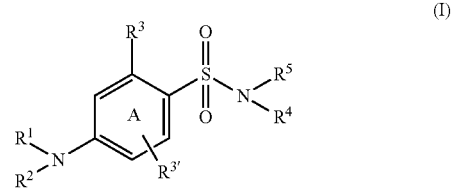

$R^1$ is selected from the group consisting of 2,4-dichlorophenyl, 3,5-dimethoxyphenyl, 2,4-dimethoxyphenyl, 4-morpholin-4-ylphenyl, 2,3-dihydro-benzo[1.4]dioxin-6-yl, 4-methoxyphenyl, phenyl, 2,4-difluorophenyl, 2-chloro-4-cyanophenyl, 4,6-dimethoxy-pyrimidin-2-yl, 6,6-dimethyl-bicyclo[3.1.1.]hept-3-ylmethyl, 2-chloro-pyridin-3-yl, 2-ethyl-2H-pyrazol-3-yl, 4-dimethylamino-phenyl, bicyclo[2.2.1]hept-2-yl, 1-aza-bicyclo[2.2.2]oct-3-yl, 1-acetyl-2,3-dihydro-1H-indol-6-yl, 2-methyl-1,3-dioxo-2,3-dihydro-1H-isoindol-5-yl, 2-chloro-4-benzoic acid ethyl ester, 2-chloro-4-benzoic acid, cycloheptyl, cyclooctyl, tetrahydro-pyran-4-ylmethyl, piperidin-1-yl, cyclopropylmethyl, cyclohexylmethyl, cyclopropyl, 3-methoxypropylamino, pyridin-2-ylmethyl, pyridin-3-ylmethyl, pyridin-4-ylmethyl, morpholin-4-yl, azepan-1-yl, 4-cyano-3-trifluoromethylphenyl, and 1,6,6-trimethyl-bicyclo[3.1.1]hept-3-yl;

$R^2$ is selected from the group consisting of hydrogen, propyl and cyclopropylmethyl;

$R^3$ is $CF_3$;

$R^{3'}$ is hydrogen;

$R^4$ is selected from the group consisting of hydrogen, $COR^6$ and a linear or branched, saturated $C_1$-$C_6$ alkyl, wherein said alkyl is unsubstituted or substituted with one or more R", wherein R" is selected from the group consisting of:
  a) a linear or branched, saturated $C_1$-$C_6$ alkoxy or an aryloxy,
  b) hydroxy,
  c) $COOR^6$, and
  d) a saturated $C_3$-$C_8$ cycloalkyl, a saturated heterocycloalkyl, an aryl or a heteroaryl, wherein said cycloalkyl, heterocycloalkyl, aryl or heteroaryl is unsubstituted or substituted with one or more R', wherein R' is as defined below;

$R^5$ is selected from the group consisting of:
  a saturated linear or branched $C_1$-$C_6$ alkyl which is substituted with one or more R' or R";
  a saturated linear or branched heteroalkyl, a saturated $C_3$-$C_8$ cycloalkyl, a saturated heterocycloalkyl, an aryl or a heteroaryl, wherein each of said heteroalkyl, cycloalkyl, heterocycloalkyl, aryl or heteroaryl is unsubstituted or substituted with one or more R' or R", wherein R' and R" are as defined above;
  or one or more of $R^1$ and $R^2$, or $R^4$ and $R^5$ together with the nitrogen to which they are attached form a heterocyclic or heteroaromatic ring, wherein said heterocyclic or heteroaromatic ring is unsubstituted or substituted with one or more R' wherein R' is as defined below;

R' is independently at each occurrence selected from the group consisting of:
  a) a linear or branched, saturated $C_1$-$C_6$ alkyl,
  b) a linear or branched, saturated $C_1$-$C_6$ haloalkyl,
  c) a linear or branched, saturated $C_1$-$C_6$ alkoxy or an aryloxy,
  d) a linear or branched, saturated $C_1$-$C_6$ haloalkoxy,
  e) a linear or branched, saturated $C_1$-$C_6$ alkylsulfonyl,
  f) a linear or branched, saturated $C_1$-$C_6$ thioalkyl or a thioaryl,
  g) a saturated $C_3$-$C_8$ cycloalkyl,
  h) an aryl,
  i) a heteroaryl,
  j) a heterocyclyl,
  k) hydroxy,
  l) cyano,
  m) nitro,
  n) halogen,
  o) $COR^6$,
  p) $COOR^6$,
  q) $CONR^7R^8$,
  r) $NHCOR^9$, and
  s) $NR^{10}R^{11}$;

$R^6$, $R^7$, $R^8$ $R^9$, $R^{10}$ and $R^{11}$ are each independently selected from the group consisting of hydrogen and a linear or branched, saturated $C_1$-$C_6$ alkyl;

or a stereoisomer, pharmaceutically acceptable salt or ester thereof.

2. The compound according to claim 1, wherein $R^4$ is selected from the group consisting of hydrogen, methyl, n-propyl, cyclopropylmethyl, C(=O)CH$_3$, CH$_2$COOtBu, CH$_2$COOH and CH$_2$CH$_2$OCH$_3$.

3. The compound according to claim 1, wherein $R^4$ is selected from the group consisting of hydrogen, $COR^6$ and a linear or branched, saturated $C_1$-$C_6$ alkyl, wherein said alkyl is unsubstituted or substituted by one or more R", wherein R" is selected from the group consisting of a linear or branched, saturated $C_1$-$C_6$ alkoxy, $COOR^6$, a saturated $C_3$-$C_8$ cycloalkyl and a saturated heterocycloalkyl.

4. The compound according to claim 1, wherein $R^5$ is selected from the group consisting of a saturated linear or branched $C_1$-$C_6$ alkyl or heteroalkyl, a saturated $C_3$-$C_8$ cycloalkyl, a saturated heterocycloalkyl and an aryl, wherein each of said heteroalkyl, cycloalkyl, heterocycloalkyl, aryl or heteroaryl is unsubstituted or substituted with one or more groups selected from the group consisting of $C_3$-$C_8$ cycloalkyl, heteroaryl, heterocycloalkyl, $COOR_6$, $COR_6$, and $NR^{10}R^{11}$, and wherein said alkyl is substituted with one or more groups selected from the group consisting of $C_3$-$C_8$ cycloalkyl, heteroaryl, heterocycloalkyl, $COOR^6$, $COR^6$, and $NR^{10}R^{11}$.

5. The compound according to claim 4, wherein $R^5$ is selected from the group consisting of hydrogen, CH$_2$CH$_2$-morpholinyl, CH$_2$-benzo[1,3]dioxolanyl, cyclopropylmethyl, tetrahydrofuranylmethyl, furanylmethyl, tetrahydropyranylmethyl, 2-methoxyethylamino, 3-methoxypropylamino, pyridylmethyl, morpholinylmethyl, tetrahydropyran-4-ylmethyl, 3-dimethylamino-2,2-dimethylpropyl, adamantanyl, phenyl, 1-cyclopropyl-1-methylethyl, benzyl, carboxymethyl-cyclopropyl, and cyclopropylmethoxy.

6. The compound according to claim 1, wherein $R^4$ and $R^5$ together with the nitrogen to which they are attached form a heterocyclic or heteroaromatic ring or wherein $R^4$ and $R^5$ together with the nitrogen and carbon to which they are respectively attached form a heterocyclic or heteroaromatic ring selected from the group consisting of a morpholinyl, dihydroindolyl, quinolinyl, isoquinolinyl, pyrazolyl, imidazolyl, isoxazolyl, thiazolyl, pyrrolyl, aziridinyl, azetidinyl, pyrrolidinyl, morpholinyl, piperazinyl, piperidinyl, tetrahydropyridinyl, azepinyl, oxapinyl, azacyclooctanyl, azaoxacyclooctanyl and azathiacyclooctanyl.

7. A compound selected from the group consisting of:
  4-(2,4-dichloro-phenylamino)-N-(2-morpholin-4-yl-ethyl)-2-trifluoromethyl-benzenesulfonamide;
  N-Benzo[1,3]dioxol-5-ylmethyl-4-(2,4-dichloro-phenylamino)-2-trifluoromethyl-benzenesulfonamide;
  N-Cyclopropylmethyl-4-(2,4-dichloro-phenylamino)-2-trifluoromethyl-benzenesulfonamide;
  N-Cyclopropylmethyl-4-(3,5-dimethoxy-phenylamino)-2-trifluoromethyl-benzenesulfonamide;
  N-cyclopropylmethyl-4-(4-methoxy-phenylamino)-2-trifluoromethyl-benzenesulfonamide;
  N-Cyclopropylmethyl-4-phenylamino-2-trifluoromethyl-benzenesulfonamide;
  4-(2,4-Dichloro-phenylamino)-N-(tetrahydro-furan-2-ylmethyl)-2-trifluoromethyl-benzenesulfonamide;
  N-Butyl-4-(2,4-dichloro-phenylamino)-2-trifluoromethyl-benzenesulfonamide;

4-(2,4-Difluoro-phenylamino)-N-(tetrahydro-furan-2-yl-methyl)-2-trifluoromethyl-benzenesulfonamide;
N-Cyclopropylmethyl-4-(4,6-dimethoxy-pyrimidin-2-ylamino)-2-trifluoromethyl-benzenesulfonamide;
4-(3,5-Dimethoxy-phenylamino)-N-(3-methoxy-propyl)-2-trifluoromethyl-benzenesulfonamide;
4-(3,5-Dimethoxy-phenylamino)-N-(tetrahydro-furan-2-ylmethyl)-2-trifluoromethyl-benzenesulfonamide;
4-(3,5-Dimethoxy-phenylamino)-N-pyridin-4-ylmethyl-2-trifluoromethyl-benzenesulfonamide;
(3,5-Dimethoxy-phenyl)-[4-(morpholine-4-sulfonyl)-3-trifluoromethyl-phenyl]-amine;
4-(3,5-Dimethoxy-phenylamino)-N-(2-morpholin-4-yl-ethyl)-2-trifluoromethyl-benzenesulfonamide;
4-(Bicyclo[2.2.1]hept-2-ylamino)-N-(tetrahydro-furan-2-ylmethyl)-2-trifluoromethyl-benzenesulfonamide;
4-(3,5-Dimethoxy-phenylamino)-N-furan-2-ylmethyl-2-trifluoromethyl-benzenesulfonamide;
4-(3,5-Dimethoxy-phenylamino)-N-isoquinolin-5-yl-2-trifluoromethyl-benzenesulfonamide;
4-(2,3-Dihydro-indol-1-yl)-N-(tetrahydro-furan-2-ylmethyl)-2-trifluoromethyl-benzenesulfonamide;
4-(Cyclopropylmethyl-propyl-amino)-N-(tetrahydro-furan-2-ylmethyl)-2-trifluoromethyl-benzenesulfonamide;
[4-(2,3-Dihydro-indole-1-sulfonyl)-3-trifluoromethyl-phenyl]-(3,5-dimethoxy-phenyl)-amine;
4-(3,5-Dimethoxy-phenylamino)-N,N-bis-(2-methoxy-ethyl)-2-trifluoromethyl-benzenesulfonamide;
4-(2,4-Dichloro-phenylamino)-N-(tetrahydro-pyran-4-ylmethyl)-2-trifluoromethyl-benzenesulfonamide;
N-Cyclopropylmethyl-4-(2,4-difluoro-phenylamino)-2-trifluoromethyl-benzenesulfonamide;
4-(2,4-Difluoro-phenylamino)-N-furan-2-ylmethyl-2-trifluoromethyl-benzenesulfonamide;
4-(Bicyclo[2.2.1]hept-2-ylamino)-N-(tetrahydro-pyran-4-ylmethyl)-2-trifluoromethyl-benzenesulfonamide;
4-(Bicyclo[2.2.1]hept-2-ylamino)-N-furan-2-ylmethyl-2-trifluoromethyl-benzenesulfonamide; and
4-(2-Chloro-4-cyano-phenylamino)-N-cyclopropylmethyl-2-trifluoromethyl-benzenesulfonamide;
N-cyclopropylmethyl-4-(2,4-dimethoxy-phenylamino)-2-trifluoromethyl-benzenesulfonamide;
N-cyclopropylmethyl-4-(2,4-dimethoxy-phenylamino)-N-propyl-2-trifluoromethyl-benzenesulfonamide;
N-cyclopropylmethyl-4-(4-morpholin-4-yl-phenylamino)-2-trifluoromethyl-benzenesulfonamide;
N-cyclopropylmethyl-4-(2,3-dihydro-benzo[1,4]dioxin-6-ylamino)-2-trifluoromethyl-benzenesulfonamide;
N-Cyclopropylmethyl-4-[(6,6-dimethyl-bicyclo[3.1.1]hept-3-ylmethyl)-amino]-2-trifluoromethyl-benzenesulfonamide;
4-(2,4-Dichloro-phenylamino)-N-(3-dimethylamino-2,2-dimethyl-propyl)-2-trifluoromethyl-benzenesulfonamide;
4-(2-Chloro-pyridin-3-ylamino)-N-(tetrahydro-pyran-4-ylmethyl)-2-trifluoromethyl-benzenesulfonamide;
4-(2-Ethyl-2H-pyrazol-3-ylamino)-N-(tetrahydro-pyran-4-ylmethyl)-2-trifluoromethyl-benzenesulfonamide;
4-(Cyclopropylmethyl-propyl-amino)-N-(tetrahydro-pyran-4-ylmethyl)-2-trifluoromethyl-benzenesulfonamide;
4-(3,5-Dimethoxy-phenylamino)-N-(tetrahydro-pyran-4-ylmethyl)-2-trifluoromethyl-benzenesulfonamide;
4-(4-Dimethylamino-phenylamino)-N-(tetrahydro-pyran-4-ylmethyl)-2-trifluoromethyl-benzenesulfonamide;
4-(2-Chloro-4-cyano-phenylamino)-N-(tetrahydro-pyran-4-ylmethyl)-2-trifluoromethyl-benzenesulfonamide;
N-Cyclopropylmethyl-4-(2,4-dichloro-phenylamino)-N-methyl-2-trifluoromethyl-benzenesulfonamide;
4-(Bicyclo[2.2.1]hept-2-ylamino)-N-cyclopropylmethyl-2-trifluoromethyl-benzenesulfonamide;
4-(2,4-Dichloro-phenylamino)-2-trifluoromethyl-benzenesulfonamide;
4-(Bicyclo[2.2.1]hept-2-ylamino)-2-trifluoromethyl-benzenesulfonamide;
4-(1-Aza-bicyclo[2.2.2]oct-3-ylamino)-N-(tetrahydro-pyran-4-ylmethyl)-2-trifluoromethyl-benzenesulfonamide;
N-Adamantan-1-yl-4-(2,4-dichloro-phenylamino)-2-trifluoromethyl-benzenesulfonamide;
4-(2,4-Dichloro-phenylamino)-N-(1,1,3,3-tetramethyl-butyl)-2-trifluoromethyl-benzenesulfonamide;
4-(2,4-Dichloro-phenylamino)-N-phenyl-2-trifluoromethyl-benzenesulfonamide;
N-(1-Cyclopropyl-1-methyl-ethyl)-4-(2,4-dichloro-phenylamino)-2-trifluoromethyl-benzenesulfonamide;
N-Benzyl-4-(2,4-dichloro-phenylamino)-2-trifluoromethyl-benzenesulfonamide;
1-[4-(2,4-Dichloro-phenylamino)-2-trifluoromethyl-benzenesulfonylamino]-cyclopropanecarboxylic acid methyl ester;
N-Cyclopropylmethyl-4-(2-methyl-1,3-dioxo-2,3-dihydro-1H-isoindol-5-ylamino)-2-trifluoromethyl-benzenesulfonamide;
N-Cyclopropylmethyl-4-(2-ethyl-2H-pyrazol-3-ylamino)-2-trifluoromethyl-benzenesulfonamide;
N-Cyclopropylmethyl-4-(4-dimethylamino-phenylamino)-2-trifluoromethyl-benzenesulfonamide;
4-(2-Chloro-pyridin-3-ylamino)-N-cyclopropylmethyl-2-trifluoromethyl-benzenesulfonamide;
4-(Bicyclo[2.2.1]hept-2-ylamino)-N-(1-cyclopropyl-1-methyl-ethyl)-2-trifluoromethyl-benzenesulfonamide;
N-(1-Cyclopropyl-1-methyl-ethyl)-4-(3,5-dimethoxy-phenylamino)-2-trifluoromethyl-benzenesulfonamide;
4-(2-Chloro-pyridin-3-ylamino)-N-(1-cyclopropyl-1-methyl-ethyl)-2-trifluoromethyl-benzenesulfonamide;
N-Cyclopropylmethoxy-4-(2,4-dichloro-phenylamino)-2-trifluoromethyl-benzenesulfonamide;
3-Chloro-4-[4-(cyclopropylmethyl-sulfamoyl)-3-trifluoromethyl-phenylamino]-benzoic acid methyl ester;
3-Chloro-4-[4-(cyclopropylmethyl-sulfamoyl)-3-trifluoromethyl-phenylamino]-benzoic acid;
4-(1-Aza-bicyclo[2.2.2]oct-3-ylamino)-N-cyclopropylmethyl-2-trifluoromethyl-benzenesulfonamide;
3-Chloro-4-[4-(1-cyclopropyl-1-methyl-ethylsulfamoyl)-3-trifluoromethyl-phenylamino]-benzoic acid ethyl ester;
3-Chloro-4-[4-(1-cyclopropyl-1-methyl-ethylsulfamoyl)-3-trifluoromethyl-phenylamino]-benzoic acid;
{[4-(Bicyclo[2.2.1]hept-2-ylamino)-2-trifluoromethyl-benzenesulfonyl]-cyclopropylmethyl-amino}-acetic acid tert-butyl ester;
{[4-(Bicyclo[2.2.1]hept-2-ylamino)-2-trifluoromethyl-benzenesulfonyl]-cyclopropylmethyl-amino}-acetic acid;
4-(Bicyclo[2.2.1]hept-2-ylamino)-N-cyclopropylmethoxy-2-trifluoromethyl-benzenesulfonamide;
N-Acetyl-4-(bicyclo[2.2.1]hept-2-ylamino)-N-cyclopropylmethyl-2-trifluoromethyl-benzenesulfonamide;
4-Cycloheptylamino-N-cyclopropylmethyl-2-trifluoromethyl-benzenesulfonamide;

4-Cyclooctylamino-N-cyclopropylmethyl-2-trifluoromethyl-benzenesulfonamide;
N-Cyclopropylmethyl-4-[(tetrahydro-pyran-4-ylmethyl)-amino]-2-trifluoromethyl-benzenesulfonamide;
N-Cyclopropylmethyl-4-(piperidin-1-ylamino)-2-trifluoromethyl-benzenesulfonamide;
N-Cyclopropylmethyl-4-(cyclopropylmethyl-amino)-2-trifluoromethyl-benzenesulfonamide;
4-Cyclohexylamino-N-cyclopropylmethyl-2-trifluoromethyl-benzenesulfonamide;
4-Cyclopropylamino-N-cyclopropylmethyl-2-trifluoromethyl-benzenesulfonamide;
N-Cyclopropylmethyl-4-(cyclopropylmethyl-propyl-amino)-2-trifluoromethyl-benzenesulfonamide;
N-Cyclopropylmethyl-4-(3-methoxy-propylamino)-2-trifluoromethyl-benzenesulfonamide;
N-Cyclopropylmethyl-4-[(pyridin-2-ylmethyl)-amino]-2-trifluoromethyl-benzenesulfonamide;
N-Cyclopropylmethyl-4-[(pyridin-3-ylmethyl)-amino]-2-trifluoromethyl-benzenesulfonamide;
N-Cyclopropylmethyl-4-(morpholin-4-ylamino)-2-trifluoromethyl-benzenesulfonamide;
N-Cyclopropylmethyl-4-[(pyridin-4-ylmethyl)-amino]-2-trifluoromethyl-benzenesulfonamide;
4-(Azepan-1-ylamino)-N-cyclopropylmethyl-2-trifluoromethyl-benzenesulfonamide;
4-(Azepan-1-ylamino)-N-(1-cyclopropyl-1-methyl-ethyl)-2-trifluoromethyl-benzenesulfonamide;
N-(1-Cyclopropyl-1-methyl-ethyl)-4-(piperidin-1-ylamino)-2-trifluoromethyl-benzenesulfonamide;
4-(4-Cyano-3-trifluoromethyl-phenylamino)-N-cyclopropylmethyl-2-trifluoromethyl-benzenesulfonamide; and
N-Cyclopropylmethyl-2-trifluoromethyl-4-(1,6,6-trimethyl-bicyclo[3.1.1]hept-3-ylamino)-benzenesulfonamide.

8. A pharmaceutical composition comprising as an active ingredient an effective amount of a compound according to claim 1, and a pharmaceutically acceptable carrier or excipient.

9. The pharmaceutical composition according to claim 8, wherein the active ingredient is 4-(Bicyclo[2.2.1]hept-2-ylamino)-N-cyclopropylmethyl-2-trifluoromethyl-benzenesulfonamide and the carrier comprises a solution of ethanol, a surfactant and water.

10. The pharmaceutical composition according to claim 8, wherein the carrier is an emulsion comprising triglycerides, lecithin, glycerol, an emulsifier, and water.

11. The pharmaceutical composition according to claim 8, in a unit dosage form suitable for oral or parenteral administration.

12. The compound according to claim 1, wherein $R^1$ is selected from the group consisting of cyclopropyl, cycloheptyl, cyclooctyl, bicyclo[2.2.1]hept-2-yl (norbornanyl), 6,6-dimethyl-bicyclo[3.1.1]hept-3-ylmethyl, 1,6,6-trimethyl-bicyclo[3.1.1]hept-3-yl, and 1-aza-bicyclo[2.2.2]oct-3-yl.

13. The compound according to claim 12, wherein $R^1$ bicyclo[2.2.1]hept-2-yl (norbornanyl).

14. The compound according to claim 1, wherein $R^2$ is hydrogen.

15. The compound according to claim 1, wherein $R^2$ is propyl or cyclopropylmethyl.

16. The compound according to claim 1, wherein wherein $R^4$ is hydrogen.

17. The compound according to claim 1, wherein wherein $R^5$ is a saturated $C_1$-$C_6$ alkyl which is substituted with a $C_3$-$C_8$ cycloalkyl.

18. The compound according to claim 16, wherein $R^5$ is cyclopropylmethyl.

19. The compound according to claim 1, wherein which is 4-(Bicyclo[2.2.1]hept-2-ylamino)-N-cyclopropylmethyl-2-trifluoromethyl-benzenesulfonamide, or a stereoisomer, pharmaceutically acceptable salt or ester thereof.

20. A pharmaceutical composition comprising as an active ingredient an effective amount of a compound according to claim 19, and a pharmaceutically acceptable carrier or excipient.

21. The pharmaceutical composition according to claim 20, wherein the carrier comprises a solution of ethanol, a surfactant and water, or wherein the carrier is an emulsion comprising triglycerides, lecithin, glycerol, an emulsifier, and water.

22. The pharmaceutical composition according to claim 20, in a unit dosage form suitable for oral or parenteral administration.

23. A pharmaceutical composition comprising as an active ingredient an effective amount of a compound according to claim 7, and a pharmaceutically acceptable carrier or excipient.

* * * * *